US005843426A

United States Patent [19]
Miller et al.

[11] Patent Number: 5,843,426
[45] Date of Patent: Dec. 1, 1998

[54] SALMONELLA VACCINES

[75] Inventors: Samuel I. Miller, Seattle, Wash.; John J. Mekalanos, Cambridge, Mass.

[73] Assignees: The General Hospital Corporation, Boston; President and Fellows of Harvard College, Cambridge, both of Miss.

[21] Appl. No.: 565,861

[22] Filed: Dec. 1, 1995

Related U.S. Application Data

[63] Continuation-in-part of Ser. No. 271,354, Jul. 6, 1994, Pat. No. 5,695,983, which is a continuation-in-part of Ser. No. 90,526, Jul. 9, 1993, Pat. No. 5,599,537, which is a continuation-in-part of Ser. No. 629,602, Dec. 18, 1990, abandoned.

[51] Int. Cl.[6] ......................... A61K 39/112; C12N 15/03; C12N 1/21
[52] U.S. Cl. .................... 424/93.2; 435/172.3; 435/252.3
[58] Field of Search ............................ 435/252.3, 172.3, 435/245; 424/93.2, 172.3, 252.3

[56] References Cited

U.S. PATENT DOCUMENTS

| | | | |
|---|---|---|---|
| 4,550,081 | 10/1985 | Stocker | 435/252.3 |
| 4,735,801 | 4/1988 | Stocker | 424/235.1 |
| 4,764,370 | 8/1988 | Fields et al. | 424/258.1 |
| 4,837,151 | 6/1989 | Stocker | 424/200.1 |
| 4,888,170 | 12/1989 | Curtiss, III | 424/200.1 |
| 5,077,044 | 12/1991 | Stocker | 424/235.1 |
| 5,210,035 | 5/1993 | Stocker | 424/235.1 |
| 5,424,065 | 6/1995 | Curtiss, III et al. | 424/93.2 |

FOREIGN PATENT DOCUMENTS

| | | |
|---|---|---|
| WO 88/09669 | 12/1988 | WIPO . |
| WO 90/11687 | 10/1990 | WIPO . |
| WO 92/11361 | 7/1992 | WIPO . |
| WO 92/17785 | 10/1992 | WIPO . |

OTHER PUBLICATIONS

Hohmann et al. Evaluation of a phoP/phoQ–deleted, aroA–deleted live oral Salmonella typhi vaccine strain in human volunteers, Vaccine vol. 14 pp. 19–24, 1996.

Curtiss et al. Stabilization of recombinant avirulent vaccine strains in vivo. Res. Microbiol. vol. 141 pp. 797–805, 1990.

Alpuche–Aranda et al., "Salmonella typhimurium Activates Virulence Gene Transcription Within Acidified Macrophage Phagosomes", *Proc. Natl. Acad. Sci. USA*, 89:10079–10083 (1992).

Alpuche–Aranda et al., "Salmonella Stimulate Macrophage Macropinocytosis and Persist Within Spacious Phagosomes", *J. Exp. Med.*, 179:601–608 (1994).

Arico et al., "Sequences Required for Expression of Bordetella Pertussis Virulence Factors Share Homology with Prokaryotic Signal Transduction Proteins", *Proc. Natl. Acad. Sci. USA*, 86:6671–75 (1989).

Beattie et al., "Evidence that Modulation Requires Sequences Downstream of the Promoters of Two vir–Repressed Genes of Bordetella Pertussis", *J. Bacteriology*, 172:6997–7004 (1990).

Behlau et al., "A PhoP–Repressed Gene Promotes Salmonella typhimurium Invasion of Epithelial Cells", *J. Bacteriology*, 175:4475–84 (1993).

Bernardini et al., "The Two–Component Regulatory System OmpR–EnvZ Controls with Virulence of Shigella flexneri", *J. Bacteriology*, 172:6274–6281 (1990).

Blomfield et al., "Allelic Exchange in *Escherichia coli* Using the *Bacillus subtilis* sacB gene and a Temperature–Sensitive pSC101 Replicon", *Mol. Microbiol.*, 5(6):1447–57 (1991).

Crosa et al., "Molecular Relationships Among the Salmonelleae," *J. Bacteriology*, 115(1):307–315 (1973).

Curtiss et al., "Immunobiology of Proteins and Peptides V Vaccines", Proceedings of the Fifth Inter'l Symposium on the Immunobiology of Proteins . . . , M.Z. Atassi, ed., pp. 33–47 (1989).

Curtiss et al., "Salmonella typhimurium Deletion Mutants Lacking Adenylate Cyclase and Cyclic AMP Receptor Protein Are Avirulent and Immunogenic", *Infec. and Immunol.*, 55:3035–43 (1987).

Curtiss et al., "Selective Delivery of Antigens by Recombinant Bacteria", *Current Topics in Microbiol. and Immunology*, R.W. Compans, eds., 146:35–49 (1989).

Curtiss, "Antigen Delivery Systems for Analysing Host Immune Responses and for Vaccine Development", *Biotechnology*, 8:237–240 (1990).

Curtiss et al., "Recombinant Avirulent Salmonella Vaccine Strains With Stable Maintenance and High Level Expression of Cloned Genes In Vivo", *Immunological Invest.*, 18:583–596 (1989).

David et al., "Leuconostoc Lactis β–Galactosidase Is Encoded by Two Overlapping Genes", *J. Bacteriology*, 174:4475–81 (1992).

Donnenberg et al., "Construction of an eae Deletion Mutant of Enteropathogenic *Escherichia coli* by Using a Positive–Selection Suicide Vector", *Infect. and Immunity*, 59:4310–17 (1991).

Dougan et al., "Construction and Characterization of Vaccine Strains of Salmonella Harboring Mutations in Two Different aro Genes", *J. Infect. Diseases* 158(6):1329–35 (1988).

Edwards et al., "Construction of ΔaroA his Δpur Strains of Salmonella Typhi", *J. Bacteriology*, 170:3991–95 (1988).

Fields et al., "A Salmonella Locus That Controls Resistance to Microbicial Proteins from Phagocytic Cells", *Science*, 243:1059–1062 (1989).

(List continued on next page.)

*Primary Examiner*—John L. LeGuvader
*Assistant Examiner*—John S. Brusca
*Attorney, Agent, or Firm*—Fish & Richardson P.C.

[57] ABSTRACT

The invention features a Salmonella cell the virulence of which is attenuated by a deletion of a portion of the PhoQ gene and Salmonella cells having a deletion of the PhoQ gene and a deletion of the PhoP gene. The invention also features vaccines comprising such bacteria.

1 Claim, 20 Drawing Sheets

OTHER PUBLICATIONS

Forrest et al., "The Human Humoral Immune Response to *Salmonella Typhi* Ty21a", *J. Infect. Diseases*, 163:336–45 (1991).

Forrest, "Indirect Measurement of Intestinal Immune Responses to an Orally Administered Attenuated Bacterial Vaccine", *Infect. and Immunity*, 60:2023–29 (1992).

Forrest, "Impairment of Immunogenicity of *Salmonella typhi* Ty21a Due to Preexisting Cross–Reacting Intestinal Antibodies", *J. Infect. Diseases*, 166:210–211 (1992).

Forrest, "Identification of an Intestinal Immune Response Using Peripheral Blood Lymphocytes", *The Lancet*, 1:81–83 (1988).

Foster et al., "Adaptive Acidification Tolerance Response of *Salmonella Typhimurium*", *J. Bacteriology*, 172:771–778 (1990).

Galan, "Virulence and Vaccine Potential of phoP Mutants of *Salmonela typhimurium*", *Abstracts of 89th Ann. Meeting of the Amer. Soc'y. for Microbiol.*, E–9 (1989).

Galan et al., "Virulence and Vaccine Potentialof phoP Mutants of *Salmonella Typhimurium*", *Microbial Pathogenesis*, 6:433–43 (1989).

Galan et al., "Distribution of the invA, –B, –C and –D Genes of *Salmonella typhimurium* Among Other Salmonella Serovars: invA Mutants of *Salmonella typhi* Are Deficient for Entry into Mammalian Cells", *Infect. and Immunity*, 59:2901–2908 (1991).

Gonzalez et al., "*Salmonella typhi* Vaccine Strain CVD 908 Expressing the Circumsporozoite Protein of Plasmodium Falciparum: Strain Construction and Safety and Immunogenicity in Humans", *J. Infect. Diseases*, 169:927–31 (1994).

Groisman et al., "*Salmonella typhimurium* phoP virulence gene is a transcriptional regulator," *Proc. Natl. Acad. Sci. USA*, 86:7077–7081 (1989).

Groisman et al., "Horizontal Transfer of a Phosphatase Gene as Evidence for Mosaic Structure of the Salmonella Genome", *EMBO J.*, 11:1309–16 (1992).

Groisman et al., "Cognate Gene Clusters Govern Invasion of Host Epithelial Cells by *Salmonella typhimurium* and Shigella flexneri", *EMBO J.*, 12:3779–87 (1993).

Gulig et al., "Identification, Genetic Analysis and DNA Sequence of a 7.8–kb Virulence Region of the *Salmonella Typhimurium* Virulence Plasmid", *Mol. Microbiol.*, 6:1395–411 (1992).

Gunn et al., "Characterization of the *Salmonella typhimurium* pagC/pagD Chromosomal Region", *J. Bacteriology*, 177:5040–47 (1995).

Heffernan et al., "The *Salmonella typhimurium* Virulence Plasmid Complement Resistance Gene rck is Homologous to a Family of Virulence–Related Outer Membrane Protein Genes, Including pagC and ail", *J. Bacteriol.*, 174:84–91 (1992).

Hirschel et al., "Inefficacy of the Commerical Live Oral Ty 21a Vaccine in the Prevention of Typhoid Fever", *Eur. J. Clin. Microbiol.*, 4:295–98 (1985).

Hohmann et al., "Macrophage–inducible expression of a model antigen in *Salmonella typhimurium* Enhances Immunogenicity", *Proc. Nat'l Acad. Sci. USA*, 92:2904–908 (1995).

Hoiseth et al., "Aromatic–dependent *Salmonella typhimurium* are Non–virulent and Effective as Live Vaccines", *Nature*, 291:238–239 (1981).

Hone et al., "Evaluation in Volunteers of a Candidate Live Oral Attenuated *Salmonella typhi* Vector Vaccine", *J. Clin. Invest.*, 90:412–20 (1992).

Kantele et al., "Specific Immunoglobulin–Secreting Human Blood Cells After Peroral Vaccination Against *Salmonella typhi*", *J. Infect. Disease*, 153(6):1126–30 (1986).

Kier et al., "Resolution and Purification of Three Periplasmic Phosphatases of *Salmonella typhimurium*", *J. Bacteriology*, 130:399–410 (1977).

Kier et al., "Regulation of Nonspecific Acid Phosphatase in Salmonella: phoN and phoP Genes", *J. Bacteriology*, 138:155–61 (1979).

Kukral et al., "Genetic Analysis in *Salmonella Typhimurium* with a Small Collection of Randomly Spaced Insertions of Transposon Tn10Δ16Δ17", *J. Bacteriology*, 169:1787–93 (1987).

Lee et al., "The Ability of Salmonella to Enter Mammalian Cells is Affected by Bacterial Growth State", *Proc. Natl. Acad. Sci. USA*, 87:4304–4308 (1990).

Lee et al., "Identification of a *Salmonella typhimurium* Invasion Locus by Selection for Hyperinvasive Mutants", *Proc. Natl. Acad. Sci. USA*, 89:1847–1851 (1992).

Leroux et al., "Characterization of the virA Locus of *Agrobacterium Tumefaciens*: a Transcriptional Regulator and Host Range Determinant", *EMBO J.*, 6:849–856 (1987).

Levine et al., "Safety, Infectivity, Immunogenicity, and In Vivo Stability of Two Attenuated Auxotrophic Mutant Strains of *Salmonella typhi*, 541Ty and 543Ty, as Live Oral Vaccines in Humans", *J. Clin. Invest.*, 79:888–902 (1987).

Levine, "Typhoid Fever Vaccines", *Vaccines*, Plotkin et al., eds. W.B. Sanders: Philadelphia, 2nd ed., Ch. 21, pp. 597–633 1994.

Levine et al., "Progress in Vaccines Against Typhoid Fever", *Revs. of Infect. Diseases*, Supp. 3, 11:S552–567 (May–Jun. 1989).

Mekalanos, "Environmental Signals Controlling Expression of Virulence Determinants in Bacteria", *J. Bacteriology*, 174:1–7 (1992).

Mekalanos, "Duplication and Amplification of Toxin Genes in Vibrio Cholerae", *Cell*, 35:253–263 (1983).

Merril et al., "Gel Protein Stains: Silver Stain", *Meth. Enzymol.*, 104:441–47, Part C, (1984).

Michaelis et al., "Mutations That Alter the Signal Sequence of Alkaline Phosphatase in *Escherichia coli*", *J. Bacteriology*, 154:366–374 (1983).

Miller et al., "Salmonella Vaccines With Mutations in The PhoP Virulence Regulon," *Institut Pasteur/Elsevier, Res. Microbiol.*, 141:817–821 (1990).

Miller et al., "Constitutive Expression of the PhoP Regulon Attenuates Salmonella Virulence and Survival within Macrophages" *J. Bacteriology* 175(5):2485–90 (1990).

Miller et al., "The PhoP virulence regulon and live oral Salmonella vaccines", *Vaccine*, 11(2):122–125 (1993).

Miller et al., "An Unusual pagC: :TnphoA Mutation Leads to an Invasion–and Virulence–Defective Phenotype in Salmonellae", *Infect. and Immunity*, 60:3763–3770 (1992).

Miller et al., "PhoP/PhoQ: macrophage–specific modulators of Salmonella virulence?", *Mol. Microbiol.* 5(9):2073–2078 (1991).

Miller et al., "A Novel Suicide Vector and Its Use in Construction of Insertion Mutations: Osmoregulation of Outer Membrane Proteins and Virulence Determinants in *Vibrio cholerae* Requires toxR", *J. Bacteriology*, 170:2575–2583 (1988).

Miller et al., "A Two–component Regulatory System (phoP phoQ) Controls *Salmonella typimurium* Virulence", *Proc. Natl. Acad. Sci. USA* 86:5054–5058 (1989).

Miller et al., "Strategies for the Development of Vaccines for Typhoid Fever, Shigellosis, and Cholera", *Annals of the N.Y. Acad. Science*, 569:145–154 (1989).

Miller et al., "Characterization of Defensin Resistance Phenotypes Associated with Mutations in the phoP Virulence Regulon of *Salmonella typhimurium*," *Infect. and Immunity* 58(11):3706–10 (1990).

O'Callaghan et al., "Characterization of Aromatic– and Purine–Dependent *Salmonella typhimurium*: Attenuation, Persistance, and Ability to Induce Protective Immunity in BALB/c Mice", *Infect. and Immunity*, 56(2):419–23 (1988).

O'Farrell, "High Resolution Two–Dimensional Electrophoresis of Proteins", *J. Biol. Chem.*, 250(10)4007–4021, (1975).

Pulkkinen et al., "A *Salmonella typhimurium* Virulence Protein Is Similar to a *Yersinia enterocolitica* Invasion Protein and a Bacteriophage Lambda Outer Membrane Protein." *J. Bacteriology* 173(1):86–93 (1991).

Sanderson et al., "Linkage Map of *Salmonella Typhimurium*, Edition VII", *Microbiol. Revs.*, 52:485–532 (1988).

Schwartz et al., "The Effect of Oral and Parenteral Typhoid Vaccination on the Rate of Infection with *Salmonella Tyhpi and Salmonella paratyphi* A Among Foreigners in Nepal", *Arch. Intern. Med.*, 150:349–51 (1990).

Selsted et al., "Enteric Defensins: Antiobiotic Peptide Components of Intestinal Host Defense", *J. Cell Biol.*, 118:929–36 (1992).

Stock et al., "Protein Phosphorylation and Regulation of Adaptive Respones in Bacteria", *Microbiol. Revs.*, 53:450–90 (1989).

Stone et al., "Identification of Novel Loci Affecting Entry of *Salmonella enteritidis* into Eukaryotic Cells", *J. Bacteriology*, 174:3945–3952 (1992).

Sugino et al., "A Monoamine–Regulated Klebsiella Aerogenes Operon Containing the Monoamine Oxidase Structural Gene (maoA) and the maoC Gene", *J. Bacteriology*, 174:2485–92 (1992).

Tacket et al., "Comparison of the Safety and Immunogenicity of ΔaroC ΔaroD and Δcya Δcrp *Salmonella typhi* Strains in Adult Volunteers", *Infect. and Immunity*, 60:536–41 (1992).

Tacket et al., "Lack of Immune Response to the Vi Component of a Vi–Positive Variant of the *Salmonella Typhi* Live Oral Vaccine Strain Ty21a in Human Studies", *J. Infect. Diseases*, 163:901–904 (1991).

Tacket et al., "Clinical Acceptability and Immunogenicity of CVD 908 *Salmonella typhi* Vaccine Strain", *Vaccine*, 10:443–46 (1992).

Taylor et al., "Broad–Host–Range Vectors for Delivery of PnphoA: Use in Genetic Analysis of Secreted Virulence Determinants of Vibrio cholerae", *J. Bacteriology*, 171(4):1870–1878, (1989).

Wick et al., "The phoP Locus Influences Processing and Presentation of *Salmonella typhimurium* Antigens by Activated Macrophages", *Mol. Microbiol.*, 16(3):465–76 (1995).

Vescovi, et al., "The Role of the PhoP/PhoQ regulon in Salmonella Virulence", *Research in Microbiology*, No. 5–6, 145:473–480 (1994).

Hohmann, et al., "phOp/PhoQ–Deleted *Salmonella typhi* (Ty800) Is a Safe and Immunogenic Single–Dose Typhoid Fever Vaccine in Volunteer", *J. Infectious Diseases*, 173:1408–14 (1996).

1kb

```
GTTAACCACT CTTAATAATA ATGGGTTTTA TAGCGAAATA CACTTTTTTA TCGCGTGTTC    60

AATATTTGCG TTAGTTATTA TTTTTTTGGA ATGTAAATTC TCTCTAAACA CAGGTGATAT   120

TTATCTTGGA ATTGTGGTGT TGATTCTATT CTTATAATAT AACAAGAAAT GTTGTAACTG   180
                                            *———▶
ATAGATATAT TAAAAGATTA AATCGGAGGG GGAATAAAGC GTGCTAAGCA TCATCGTGAA   240

TATGATTACA GCGCCTGCGA TGGCATATAA CCGTATTGCG GATGGAGCGT CACGTGAGGA   300

CTGTGAAGCA CAATGCGATA TGTTCTGATT ATATGGCGAG TTTGCTTAAT GACATGTTTT   360

TAGCCGAACG GTGTCAAGTT TCTTAATGTG GTTGTGAGAT TTTCTCTTTA AATATCAAAA   420

TGTTGCATGG GTGATTTGTT GTTCTATAGT GGCTAAAGAC TTTATGGTTT CTGTTAAATA   480

TATATGCGTG AGAAAAATTA GCATTCAAAT CTATAAAAGT TAGATGACAT TGTAGAACCG   540

GTTACCTAAA TGAGCGATAG AGTGCTTCGG TAGTAAAAAT ATCTTCAGG AAGTAAACAC   ‑600

ATCAGGAGCG ATAGCGGTGA ATTATTCGTG GTTTTGTCGA TTCGGCATAG TGGCGATAAC   660

TGAATGCCGG ATCGGTACTG CAGGTGTTTA AACACACCGT AAATAATAAG TAGTATTAAG   720

GAGTTGTT                                                           728
```

```
ATG AAA AAT ATT ATT TTA TCC ACT TTA GTT ATT ACT ACA AGC GTT TTG    776
Met Lys Asn Ile Ile Leu Ser Thr Leu Val Ile Thr Thr Ser Val Leu
              5                  10                 15

GTT GTA AAT GTT GCA CAG GCC GAT ACT AAC GCC TTT TCC GTG GGG TAT    824
Val Val Asn Val Ala Gln Ala Asp Thr Asn Ala Phe Ser Val Gly Tyr
           20              25                 30

GCA CGG TAT GCA CAA AGT AAA GTT CAG GAT TTC AAA AAT ATC CGA GGG    872
Ala Arg Tyr Ala Gln Ser Lys Val Gln Asp Phe Lys Asn Ile Arg Gly
         35              40                 45

GTA AAT GTG AAA TAC CGT TAT GAG GAT GAC TCT CCG GTA AGT TTT ATT    920
Val Asn Val Lys Tyr Arg Tyr Glu Asp Asp Ser Pro Val Ser Phe Ile
       50              55                 60

TCC TCG CTA AGT TAC TTA TAT GGA GAC AGA CAG GCT TCC GGG TCT GTT    968
Ser Ser Leu Ser Tyr Leu Tyr Gly Asp Arg Gln Ala Ser Gly Ser Val
65           70                 75                 80

GAG CCT GAA GGT ATT CAT TAC CAT GAC AAG TTT GAG GTG AAG TAC GGT   1016
Glu Pro Glu Gly Ile His Tyr His Asp Lys Phe Glu Val Lys Try Gly
              85                 90                 95

TCT TTA ATG GTT GGG CCA GCC TAT CGA TTG TCT GAC AAT TTT TCG TTA   1064
Ser Leu Met Val Gly Pro Ala Tyr Arg Leu Ser Asp Asn Phe Ser Leu
           100             105                110

TAC GCG CTG GCG GGT GTC GGC ACG GTA AAG GCG ACA TTT AAA GAA CAT   1112
Tyr Ala Leu Ala Gly Val Gly Thr Val Lys Ala Thr Phe Lys Glu His
         115             120                125

TCC ACT CAG GAT GGC GAT TCT TTT TCT AAC AAA ATT TCC TCA AGG AAA   1160
Ser Thr Gln Asp Gly Asp Ser Phe Ser Asn Lys Ile Ser Ser Arg Lys
130             135                140
```

FIG. 3A

```
ACG GGA TTT GCC TGG GGC GCG GGT GTA CAG ATG AAT CCG CTG GAG AAT    1208
Thr Gly Phe Ala Trp Gly Ala Gly Val Gln Met Asn Pro Leu Glu Asn
145                 150                 155                 160

ATC GTC GTC GAT GTT GGG TAT GAA GGA AGC AAC ATC TCC TCT ACA AAA    1256
Ile Val Val Asp Val Gly Tyr Glu Gly Ser Asn Ile Ser Ser Thr Lys
                165                 170                 175

ATA AAC GGC TTC AAC GTC GGG GTT GGA TAC CGT TTC TGA AAAGC          1300
Ile Asn Gly Phe Asn Val Gly Val Gly Tyr Arg Phe
            180                 185
```

ATAAGCTATG CGGAAGGTTC GCCTTCCGCA CCGCCAGTCA ATAAAACAGG GCTTCTTTAC 1360

CAGTGACACG TACCTGCCTG TCTTTTCTCT CTTCGTCATA CTCTCTTCGT CATAGTGACG 1420

CTGTACATAA CATCTCACTA GCATAAGCAC AGATAAAGGA TTGTGGTAAG CAATCAAGGT 1480

TGCTCAGGTA GGTGATAAGC AGGAAGGAAA ATCTGGTGTA ATAACGCCA GATCTCACAA 1540

GATTCACTCT GAAAAATTTT CCTGGAATTA ATCACAATGT CATCAAGATT TTGTGACCGC 1600

CTTCGCATAT TGTACCTGCC GCTGAACGAC TACTGAAAAG TAGCAAGGTA TGTATTTTAT 1660

CCAGGAGAGC ACCTTTTTTG CGCCTGGCAG AAGTCCCCAG CCGCCACTAG CTCAGCTGGA 1720

TAGAGCATCA ACCTCCTAAG TTGATGGTGC GAGGTTCGAG GCCTCGGTGG CGGTCCAATG 1780

TGGTTATCGT ATAATGTTAT TACCTCAGTG TCAGGCTGAT GATGTGGGTT CGACTCCCAC 1840

TGACCACTTC AGTTTTGAAT AAGTATTGTC TCGCAACCCT GTTACAGAAT AATTTCATTT 1900

ATTACGTGAC AAGATAGTCA TTTATAAAAA ATGCACAAAA ATGTTATTGT CTTTTATTAC 1960

TTGTGAGTTG TAGATTTTTC TTATGCGGTG AATCCCCCTT TGCGGCGGGG CGTCCAGTCA 2020

AATAGTTAAT GTTCCTCGCG AACCATATTG ACTGTGGTAT GGTTCACCGG GAGGCACCCG 2080

GCACCGCAAT TTTTTATAAA ATGAAATTCA CACCCTATGG TTCAGAGCGG TGTCTTTTTA 2140

CATCAGGTGG GCAAGCATAA TGCAGGTTAA CTTGAAAGAT ACGATCAATA GCAGAAACCA 2200

GTGATTTCGT TTATGGCCTG GGGATTTAAC CGCGCCAGAG CGTATGCAAG ACCCTGGCGC 2260

GGTTGGCCGG TGATCGTTCA ATAGTGCGAA TATGAATGGT TACCAGCCGC CTGCGAATTC 2320

(SEQUENCE ID NO. 1)  FIG. 3B

| | | | | | | | | | | |
|---|---|---|---|---|---|---|---|---|---|---|
| 5' | GAG | CGC | ATT | ATC | AGA | TAA | ATT | GAT | TTA | TTTCTCACT |
| TTC | ATT | CTA | TTT | TCA | TCA | | | | | |
| GGA | ATC | CCT | GTG | TCC | TGT | GCG | GTA | ATC | TGC | TGCTATCGA |
| GAA | CGA | CAG | ACA | TCG | | | | | | |
| CTA | ACA | GTA | TAT | ATG | GAA | ACA | TCA | AAA | GAG | AAGACGATA |
| ACA | AGC | CCA | GGG | CCA | TAC | | | | | |
| ATA | GTT | CGA | TTA | CTT | AAC | AGC | TCA | CTG | AAC | GGCTGTGAG |
| TTT | CCA | TTG | CTG | ACA | GGC | | | | | |
| CGA | ACA | CTC | TTT | GTG | GTA | GGT | CAG | AGT | GAT | GCGCTCACT |
| GCT | TCA | GGT | CAA | CTC | CCT | | | | | |
| GAT | ATA | CCT | GCC | GAT | AGC | TTT | TTT | ATC | CCG | CTGGACCAT |
| GGC | GGA | GTA | AAT | TTT | GAA | | | | | |
| ATC | CAG | GTG | GAT | ACG | GAT | GCG | ACC | GAA | ATT | ATACTCCAT |
| GAG | CTG | AAA | GAA | GGA | AAT | | | | | |
| TCT | GAA | TCT | CGT | TCG | GTG | CAA | TTA | AAT | ACG | CCAATACAG |
| GTC | GGT | GAA | TTG | CTT | ATC | | | | | |
| CTG | ATT | CGC | CCG | GAA | AGC | GAG | CCG | TGG | GTG | CCCGAGCAG |
| CCT | GAG | AAG | TTA | GAA | ACG | | | | | |
| TCT | GCA | AAA | AAG | AAC | GAG | CCG | CGT | TTT | AAA | AACGGAATT |
| GTA | GCA | GCA | CTG | GCC | | | | | | |

FIG. 5A

```
GGG     TTT TTT ATA TTG GGA ATT GGG ACT GTG GGGACGTTA
TGG     ATA CTT AAC TCG CCG
CAG     CGG CAG GCC CGA GAG CTC GAT TCG TTA TTGGGGCAG
GAG     AAG GAG CGT TTT CAG GTG     TTG CCA GGCC 3'
```

FIG. 5B

```
       _HpaI_      ·····                    ·····
   1  GGTTAACTCTTCGTTGAATAAAAAATGTCAATGACGTTCCATAATTCAGGAGATGAACTT   60

61  CACAAGTCATTATATATAACAGGAGGTGCTATGAAACATCATGCTTTTATGCTTTGGTCA  120
                                  M  K  H  H  A  F  M  L  W  S
                          pagD    ▼
 121  TTACTTATTTTTTCATTCCATGTTTTGGCCAGTTCAGGCCATTGTTCTGGTTTACAACAG  180
       L  L  I  F  S  F  H  V  L  A  S  S  G  H  C  S  G  L  Q  Q 181  GCATCATGGGATATTTTTATCTACGATTTTGGTAGTAAAACCCCGCAACCACCTACAAAT  240
       A  S  W  D  I  F  I  Y  D  F  G  S  K  T  P  Q  P  P  T  N 241  ACTGATAAAAAGCAAGCCAGGCAGATTAGTTCACCGTCCTGCCCGACGACAAAACCCATG  300
       T  D  K  K  Q  A  R  Q  I  S  S  P  S  C  P  T  T  K  P  M 301  ATGTCCGCACCAGTCAATGACGCCAGGAAAGGGAATACTTTCTCCAGAACATAATGTTAT  360
       M  S  A  P  V  N  D  A  R  K  G  N  T  F  S  R  T  *    (SEQ ID NO:6)

361  TTATCTACAATGGTGCCGACGACTACTTTTAGCCACCCGGAAATCTTGATTGCCATCAAA  420

421  TATAGCTGGCATTATTTTTCCTGACGTGTATAGTGCGCCTCGTTATCCCCATTAAGGAAT  480

481  TTGTTTGTCTCGTAAAATGACAGGAATTGTCAAAACCTTTGATTGTAAGAGCGGTAAAGG  540

541  TCTCATCACCCCCTCCGATGACGCAAAGATGTTCAGGTCCACATTTCAGCATGTCGCCAA  600

601  CACGAAACAGAAGCGCTTATCCCCGGTATACGCGTTGAGTTTTATCGTATTAATGGCCTC  660

661  CGCGGACCTACCGCCGCCAACGTTTATCTTTCATAATTCGTCACCCGGCATTTTTCAGAA  720

721  AAATTTAGCGAGTACGTCTACCTCCGCAGCCTGCTATGAGGCTTTGCCTGAAAGGCTGCA  780

781  GAATGTTTTCAGTGGCGAAAATCTAAAAGATTTATTTTGCTAATCAGTCCTGTGACCTCT  840

841  TTTATCATATATCGGGTGCCCCCCCTTCTCACTTTGTTTAACGTGAAGAAATGTACAGCC  900

901  GTTTTTCACTGTGATAGCATCTAATATTGCAAAAGTATTTAACGCTATATACCCATTGTC  960

961  ACAGGAGTGGCTGCGTGCGAGCTGAGCTATTTAACCGAAGTATTTATGTGATCATTGGAA 1020

1021  TTATCTCTATTGCCGCTCAATGCTACGTCATATTCAGTGGGTATAAATCGCCAATATAGT 1080

1081  TGTAACGCTATTTATTTTTAGGGTAATAATTGAATGACTTTGCTTTCAGGAAAAACCACA 1140
                                   M  T  L  L  S  G  K  T  T
                          envE
1141  CTCGTTCTCTGCCTCTCCTCTATTTTATGTGGATGTACGACGAACGGCTTACCCACACCT 1200
       L  V  L  C  L  S  S  I  L  C  G  C  T  T  N  G  L  P  T  P 1201  TATAGTATTAATTTGTCGTTCCCCGTCATTACACAAAACCAGATTAATTCCGGTGGTTAT 1260
       Y  S  I  N  L  S  F  P  V  I  T  Q  N  Q  I  N  S  G  G  Y 1261  TACATAAATGACGCGAACAAATTCGGACAACTCATGGTCTCTGCCTTCATGCAGGCCCA 1320
       Y  I  N  D  A  E  Q  I  R  T  T  D  G  L  C  L  D  A  G  P 1321  GATCAACAGAATCGTTTGACGCTGCGGGAGTGTAAGCATGTGCAATCTCAGCTTTTCTCA 1380
       D  Q  Q  N  R  L  T  L  R  E  C  K  H  V  Q  S  Q  L  F  S
```

FIG. 8A

```
1381  TTTCACCGAGACAGAATCACGCAGGGTGAGAAATGTCTGGATGCCGCAGACAAGGTACAA  1440
       F  H  R  D  R  I  T  Q  G  E  K  C  L  D  A  A  D  K  V  Q

1441  AAGAAGGCACACCAATCATTCTTTATTCATGCACGGGTAATGATAACCAGCGCTGGCTCA  1500
       K  K  A  H  Q  S  F  F  I  H  A  R  V  M  I  T  S  A  G  S

1501  CTGATCATAACAAAATTAAGGGGAAACAGAGCCGAAAATGCCTGGGCACAAATAGCATTA  1560
       L  I  I  T  K  L  R  G  N  R  A  E  N  A  W  A  Q  I  A  L

1561  TTGTCAGAAAAGGCGACCCTGTTGTGTTGGCCGATTGCGATTTTAGTCGCGCCCTGGAAT  1620
       L  S  E  K  A  T  L  L  C  W  P  I  A  I  L  V  A  P  W  N

1621  TTACCATCAGGTAGCAGGACACCGCTGTGAAGAGAGTGCCGCTAACCTCTTGACACGACA  1680
       L  P  S  G  S  R  T  P  L  *   (SEQ ID NO:7)

1681  ACAGGTTAGCGACCTTTACTTCCACGTGCGATCAATTTACTTTACGTCCGCAACGTCAGG  1740

1741  ATGACAAAACGGCGGCTAAACCTTGACACCAGTTATATACCCAGCTTAAATACTGGTCAT  1800

1801  CCAACCAGTAAAAAGGAAATGGCGATGTTCGTCGAACTCGTTTATGACAAGCGAAATGTT  1860
                                M  F  V  E  L  V  Y  D  K  R  N  V
                                msgA
1861  GAAGGTTTGCCAGGCGCACGCGAAATCATCCTCAATGAACTCACAAAACGCGTACATCAA  1920
       E  G  L  P  G  A  R  E  I  I  L  N  E  L  T  K  R  V  H  Q 1921  CTTTTTCCCGATGCGCAAGTGAAAGTTAAGCCAATGCAGGCGAACGCATTAAACAGTGAC  1980
       L  F  P  D  A  Q  V  K  V  K  P  M  Q  A  N  A  L  N  S  D 1981  TGTACAAAAACCGAGAAAGAACGGCTGCACCGTATGCTGGAAGAGATGTTTGAAGAGGCT  2040
       C  T  K  T  E  K  E  R  L  H  R  M  L  E  E  M  F  E  E  A 2041  GATATGTGGCTGGTCGCCGAATAACGTCCCCTCCTGCGAAAGCCAACATGTCCGATCGAA  2100
       D  M  W  L  V  A  E  *   (SEQ ID NO:8)

2101  AACAGCGCCCTCAGGCGCTGTCTGTCACGATATAACGCAAACGCTACCACTCAGAACATG  2160

2161  TTGTTGTTGATACCTCAGACCGGTATGTGGAACCGACATTCATCGCTTCACTGGCCTGTC  2220

2221  GGTATGAGTAGCCCTTATCAACAATCAGCTGTCCGCATTCCAGCCTGAAATCTGAAAGTA  2280

2281  CGTTTCGTTTTGTTGTTTATTAAGAGCCTATCCCATTAGACTCTTTTATTCGCCAAACTG  2340

2341  GCTTTAACGATTACGCCTACTGGGATAGGTTCTAAACTTATCATCAATACGTAAAATACC  2400

2401  TATTTACGAACAAAAAGTAACAGGTAAAAATCCGAAATAAAACCAGCATAACTAAAACTT  2460

2461  ACTGCAGATATGCACACGCATTATTACTATGTTTCCAGGATAGTCTCGACCAGTCAAGAC  2520

2521  TATCTATTTTATATAAAAAGGGAAATACTTCACATGAATAAAATACATGTTACATATAAA  2580
                                     M  N  K  I  H  V  T  Y  K
                                     envF
2581  AATCTCTTACTTCCGATTACCTTCATCGCCGCAACTCTAATTAGCGCCTGTGATAACGAT  2640
       N  L  L  P  I  T  F  I  A  A  T  L [I  S  A  C] D  N  D 2641  AAAGATGCCATGGCGGAAGCTGAAAAAAATCAAGAGAAATACATGCAAAAAATCCAGCAA  2700
       K  D  A  M  A  E  A  E  K  N  Q  E  K  Y  M  Q  K  I  Q  Q
```

FIG. 8B

```
2701 AAAGAGCACCAGCAATCAATGTTCTTTTACGACAAAGCCGAAATGCAAAAAGCTATTGCC 2760
      K  E  H  Q  Q  S  M  F  F  Y  D  K  A  E  M  Q  K  A  I  A

2761 AATATCAACGCAAAAGGTGGAGCCAATCTTGCGATTATTGAAGTCCGTTTCTTCAAGGGC 2820
      N  I  N  A  K  G  G  A  N  L  A  I  I  E  V  R  F  F  K  G

2821 GGGTATTCATTCATTCGACAAAGCGTTAACACCCCTGCTAAAGTAGAGGTGTTTAAATTT 2880
      G  Y  S  F  I  R  Q  S  V  N  T  P  A  K  V  E  V  F  K  F

2881 AACAACGGCTACTGGGGGGGACCTTCGCCTGTCAATTTAACCATCTTTGGCACTATAACA 2940
      N  N  G  Y  W  G  G  P  S  P  V  N  L  T  I  F  G  T  I  T

2941 GAGGAGCAAAAACAAGAAGCACTAAAAGAGGCTTTATTCAAATTCGACTCGATCAATTTC 3000
      E  E  Q  K  Q  E  A  L  K  E  A  L  F  K  F  D  S  I  N  F

3001 AGCATTATACCAGAGCGTATTCAGGAAACAATTAAACGCGCTAACGCCAGTGGCATCATT 3060
      S  I  I  P  E  R  I  Q  E  T  I  K  R  A  N  A  S  G  I  I

3061 TCCGTTACGGAAGATAGCGATATCGTTGTACGAGCAGAGATAGCTCATAATGGCGAATTC 3120
      S  V  T  E  D  S  D  I  V  V  R  A  E  I  A  H  N  G  E  F

3121 GTCTATGACATTACCATCACTGCTAAAAATACAGCACGTGCGGTAATGACCTTAAATAAG 3180
      V  Y  D  I  T  I  T  A  K  N  T  A  R  A  V  M  T  L  N  K

3181 GATGGTTCTATTGCCGGATATGAGATCAAAGAACCTTTCGCCCCAAAAAAAGAAGCCGAA 3240
      D  G  S  I  A  G  Y  E  I  K  E  P  F  A  P  K  K  E  A  E

3241 AAAGCACAGCAACTTGTTGAACAATCGAGAAAAGACATTGAAAGTCCAGCGTAAAAAAGC 3300
      K  A  Q  Q  L  V  E  Q  S  R  K  D  I  E  S  P  A  *  (SEQ ID NO:9)

3301 AGCTCGAAAGATGAACGAAATACAGCAGACATTTAAAAATAGCAGGCGATACAAACATTG 3360

3361 ATAAAAATTATAGCGCGAAAGAGCGCGTGCCAGGTACTAAGGCACTGCTTGAAGACAGCG 3420

3421 AATCGCTATTTCATTCTCTGACACTGTAATTTTTCGTACTCAAGATGTTTATTTATTGAG 3480

3481 TCTTTTGTGGATAACCAGGTGAAGTTATGTGACGCCAGGAATCTATTCCAGCGGGCGTAC 3540

3541 TTGTTGGAGCCAGTGTGAAGCCCGGCAGCGCGCAGAAACCGGAGCGTATACGTTGTACGT 3600

3601 AAGAATTTCCAGCACTGCCCCACCTAAAAATGATGAATAAAATAGATATTTTAAAGACGT 3660

3661 AATATGAAGAATTTTTTCAAAATAATTACTGATTTCATCGCGGATATTTCCCTTGATCTA 3720

3721 TTTGCTATATTTTTATGCATGTTATTCGTATACAAAACAGGACCATCAATTGGTGTGATA 3780

3781 TCATTTTTTATTGCATTAATTATTTATATCATTCTTCATTTTTTTTTACTCATTTCTTGA 3840

3841 AAAAATCATAAAAAAAATATTCAAATAAGTATTTAAAATTATTGTTTTGTGGTACAAATT 3900

3901 CAGCGCAATAAAACAGAGCAACTAAAAAAAATTAGGCGTAGCGAAGTGGAAAAGGACTGT 3960

3961 CATGTACTGGACCGTGAGCTGGTCGGGAGAGCAATGTACGGGAAAGAGCGAAATACTGTC 4020
                                                           _ClaI_
4021 ATTGATATGAGCAGGAATATCGAT 4044 (SEQ ID NO:5)
```

FIG. 8C

```
TTTTGGTTTGCTGCNCGTTTGGGATAACTGCATAGAGAGCGGCCAAGTCGCTTGCGGTCG
         10                  30                  50

GTATCTCGAGTATATCGAAATCCATGTGGCCATTGACCTCTTCAAGCGCTCACGTTAACT
         70                  90                 110

ACCTGCTCTTTTTTGAGCACCAACATCCCAGGTTCGTCACAGTAAATCGTATCGTGATTA
        130                 150                 170

TTGCTAATCGTCAGTTTACCGCTCCGAAAGCAAACTANAAGTGAAACTGCTTACATAAAG
        190                 210                 230

ATTTTTGATGGTAACCTGCTGAGTCTGACTTTTAATTTGCTGCCGGGTATTTGTCAAAAG
        250                 270                 290

TGATTTTAATTTCTGTAAGTTATCTGCGGCAGGACGCTGATGACTATTACTTACAAAGGT
        310                 330                 350

TACATTTTCCATATTATCCCTTTGTTAACTTATTTTAATGTTCCTTACTGGTATCCTAC
        370                 390                 410

TGAAAAAATCTGAGTTGTAAATGCTCTTTATTAGCGTGTGTTGGCAATGGTCTGATTGTT
        430                 450                 470

ACACCAAAAGAACCCAAATTTGGGTAATTTATCTACAGTAGTTTAAGCCCCAATGGGGAT
        490                 510                 530

GATGGTTCTTTTAATATGTGTTGAGACGCATTATACAGAATAAATTGATTTTATTTCTCA
        550                 570                 590

CTTTTCATTCTATTTTCATCAGGAATCCCTGTGTCCTGTGCGGTAATCTGCTGCTATCGA
        610                 630                 650
                                prgH
GAACGACAGACATCGCTAACAGTATATATGGAAACATCAAAAGAGAAGACGATAACAAGC
                                M  E  T  S  K  E  K  T  I  T  S
        670                 690                 710
```

FIG. 9A

```
CCAGGGCCATACATAGTTCGATTACTTAACAGCTCACTGAACGGCTGTGAGTTTCCATTG
 P  G  P  Y  I  V  R  L  L  N  S  S  L  N  G  C  E  F  P  L
       730              750              770
CTGACAGGCCGAACACTCTTTGTGGTAGGTCAGAGTGATGCGCTCACTGCTTCAGGTCAA
 L  T  G  R  T  L  F  V  V  G  Q  S  D  A  L  T  A  S  G  Q
       790              810              830
CTCCCTGATATACCTGCCGATAGCTTTTTTATCCCGCTGGACCATGGCGGAGTAAATTTT
 L  P  D  I  P  A  D  S  F  F  I  P  L  D  H  G  G  V  N  F
       850              870              890
GAAATCCAGGTGGATACGGATGCGACCGAAATTATACTCCATGAGCTGAAAGAAGGAAAT
 E  I  Q  V  D  T  D  A  T  E  I  I  L  H  E  L  K  E  G  N
       910              930              950
TCTGAATCTCGTTCGGTGCAATTAAATACGCCAATACAGGTCGGTGAATTGCTTATCCTG
 S  E  S  R  S  V  Q  L  N  T  P  I  Q  V  G  E  L  L  I  L
       970              990             1010
ATTCGCCCGGAAAGCGAGCCGTGGGTGCCCGAGCAGCCTGAGAAGTTAGAAACGTCTGCA
 I  R  P  E  S  E  P  W  V  P  E  Q  P  E  K  L  E  T  S  A
      1030             1050             1070
AAAAAGAACGAGCCGCGTTTTAAAAACGGAATTGTAGCAGCACTGGCCGGGTTTTTTATA
 K  K  N  E  P  R  F  K  N  G  I  V  A  A  L  A  G  F  F  I
      1090             1110             1130
TTGGGAATTGGGACTGTGGGGACGTTATGGATACTTAACTCGCCGCAGCGGCAGGCCGCA
 L  G  I  G  T  V  G  T  L  W  I  L  N  S  P  Q  R  Q  A  A
      1150             1170             1190
GAGCTCGATTCGTTATTGGGGCAGGAGAAGGAGCGTTTTCAGGTGTTGCCAGGCCGGGAC
 E  L  D  S  L  L  G  Q  E  K  E  R  F  Q  V  L  P  G  R  D
      1210             1230             1250
AAAATGCTCTATGTCGCTGCGCAAAATGAAAGAGATACGTTGTGGGCTCGTCAGGTTTTA
 K  M  L  Y  V  A  A  Q  N  E  R  D  T  L  W  A  R  Q  V  L
      1270             1290             1310
GCGAGGGGCGATTATGATAAAAATGCGCGAGTGATTAACGAAAACGAAGAAAATAAGCGT
 A  R  G  D  Y  D  K  N  A  R  V  I  N  E  N  E  E  N  K  R
      1330             1350             1370
ATCTCTATCTGGCTGGATACCTATTATCCGCAGCTGGCTTATTATCGGATTCATTTCGAT
 I  S  I  W  L  D  T  Y  Y  P  Q  L  A  Y  Y  R  I  H  F  D
      1390             1410             1430
GAGCCGCGTAAACCCGTTTTCTGGCTAAGCCGCCAGCGAAACACGATGAGCAAGAAAGAG
 E  P  R  K  P  V  F  W  L  S  R  Q  R  N  T  M  S  K  K  E
      1450             1470             1490
CTCGAGGTGTTAAGTCAAAAGCTGAGAGCGCTAATGCCTTACGCGGATTCGGTTAACATC
 L  E  V  L  S  Q  K  L  R  A  L  M  P  Y  A  D  S  V  N  I
      1510             1530             1550
ACGTTGATGGACGATGTTACCGCAGCAGGCCAGGCGGAAGCGGGGCTAAAACAGCAGGCG
 T  L  M  D  D  V  T  A  A  G  Q  A  E  A  G  L  K  Q  Q  A
```

FIG. 9B

```
              1570                1590                1610
TTACCTTATTCCCGCAGGAATCATAAGGGGGGCGTAACGTTTGTTATTCAGGGGGCGCTC
 L  P  Y  S  R  R  N  H  K  G  G  V  T  F  V  I  Q  G  A  L
              1630                1650                1670

GATGATGTAGAAATACTCAGAGCCCGTCAATTTGTCGATAGCTATTACCGCACATGGGA
 D  D  V  E  I  L  R  A  R  Q  F  V  D  S  Y  Y  R  T  W  G
              1690                1710                1730

GGACGCTATGTGCAGTTTGCGATCGAATTAAAAGATGACTGGCTCAAGGGGCGCTCATTT
 G  R  Y  V  Q  F  A  I  E  L  K  D  D  W  L  K  G  R  S  F
              1750                1770                1790

CAGTACGGGGCGGAAGGTTATATCAAAATGAGCCCAGGCCATTGGTATTTCCCAAGCCCA
 Q  Y  G  A  E  G  Y  I  K  M  S  P  G  H  W  Y  F  P  S  P
              1810                1830                1850
                                              prgI
CTTTAATTTAACGTAAATAAGGAAGTCATTATGGCAACACCTTGGTCAGGCTATCTGGAT
 L  ***  (SEQ ID NO: 11)           M  A  T  P  W  S  G  Y  L  D
              1870                1890                1910

GACGTCTCAGCAAAATTTGATACGGGCGTTGATAATCTACAAACGCAGGTAACAGAGGCG
 D  V  S  A  K  F  D  T  G  V  D  N  L  Q  T  Q  V  T  E  A
              1930                1950                1970

CTGGATAAAATTAGCAGCAAAACCCTCCGATCCGGCGCTACTGGCGGCGTATCAGAGTAAG
 L  D  K  L  A  A  K  P  S  D  P  A  L  L  A  A  Y  Q  S  K
              1990                2010                2030

CTCTCGGAATATAACTTGTACCGTAACGCGCAATCGAACACGGTAAAAGTCTTTAAGGAT
 L  S  E  Y  N  L  Y  R  N  A  Q  S  N  T  V  K  V  F  K  D
              2050                2070                2090
                                                       prgJ
ATTGATGCTGCCATTATTCAGAACTTCCGTTAATCAGTTATAAGGTGGATTATGTCGATT
 I  D  A  A  I  I  Q  N  F  R  *  (SEQ ID NO:12)    M  S  I
              2110                2130                2150

GCAACTATTGTCCCTGAGAATGCCGTTATAGGGCAGGCGGTCAATATCAGGTCTATGAA
 A  T  I  V  P  E  N  A  V  I  G  Q  A  V  N  I  R  S  M  E
              2170                2190                2210

ACGGACATTGTCTCGCTGGATGACCGGCTACTCCAGGCTTTTTCTGGTTCGGCGATTGCC
 T  D  I  V  S  L  D  D  R  L  L  Q  A  F  S  G  S  A  I  A
              2230                2250                2270

ACGGCTGTGGATAAACAGACGATTACCAACAGGATTGAGGACCCTAATCTGGTGACGGAT
 T  A  V  D  K  Q  T  I  T  N  R  I  E  D  P  N  L  V  T  D
              2290                2310                2330

CCTAAAGAGCTGGCTATTTCGCAAGAGATGATTTCAGATTATAACCTGTATGTTTCTATG
 P  K  E  L  A  I  S  Q  E  M  I  S  D  Y  N  L  Y  V  S  M
              2350                2370                2390
                                                       prgK
GTCAGTACCCTTACTCGTAAAGGAGTCGGGGCTGTTGAAACGCTATTACGCTCATGATTC
 V  S  T  L  T  R  K  G  V  G  A  V  E  T  L  L  R  S  ***  (SEQ ID NO:13)
              2410                2430                2450  M  I  R
```

FIG. 9C

```
GTCGATATCTATATACTTTTCTGCTGGTAATGACCCTTGCCGGCTGTAAGGATAAGGATC
  R  Y  L  Y  T  F  L  L  V  M  T  L  A  G  C  K  D  K  D  L
    2470              2490              2510

TTTTAAAAGGACTGGACCAGGAACAGGCTAATGAGGTCATTGCCGTTCTGCAAATGCACA
  L  K  G  L  D  Q  E  Q  A  N  E  V  I  A  V  L  Q  M  H  N
    2530              2550              2570

ATATAGAGGCGAATAAAATTGATAGCGGAAAATTGGGCTATAGCATTACCGTTGCTGAGC
  I  E  A  N  K  I  D  S  G  K  L  G  Y  S  I  T  V  A  E  P
    2590              2610              2630

CTGATTTTACCGCTGCGGTGTACTGGATTAAAACTTATCAGCTTCCTCCCCGGCCACGGG
  D  F  T  A  A  V  Y  W  I  K  T  Y  Q  L  P  P  R  P  R  V
    2650              2670              2690

TGGAAATAGCGCAGATGTTCCCGGCGGATTCGCTGGTATCGTCTCCGCGAGCTGAAAAGG
  E  I  A  Q  M  F  P  A  D  S  L  V  S  S  P  R  A  E  K  A
    2710              2730              2750

CCAGGTTATATTCGGCTATTGAACAGCGACTGGAACAGTCATTACAGACGATGGAGGGCG
  R  L  Y  S  A  I  E  Q  R  L  E  Q  S  L  Q  T  M  E  G  V
    2770              2790              2810

TGCTCTCCGCCAGGGTCCATATTAGTTATGATATTGATGCTGGTGAAAATGGCCGCCCGC
  L  S  A  R  V  H  I  S  Y  D  I  D  A  G  E  N  G  R  P  P
    2830              2850              2870

CAAAACCTGTTCATCTGTCGGCATTAGCCGTATATGAACGAGGTTCGCCGCTTGCGCATC
  K  P  V  H  L  S  A  L  A  V  Y  E  R  G  S  P  L  A  H  Q
    2890              2910              2930

AGATCAGCGATATCAAGCGTTTCTTAAAGAATAGTTTTGCCGATGTGGATTATGACAACA
  I  S  D  I  K  R  F  L  K  N  S  F  A  D  V  D  Y  D  N  I
    2950              2970              2990

TTTCTGTTGTGTTGTCAGAACGTTCTGATGCCCAATTACAGGCTCCCGGCACACCAGTAA
  S  V  V  L  S  E  R  S  D  A  Q  L  Q  A  P  G  T  P  V  K
    3010              3030              3050

AACGTAATTCTTTTGCAACCAGTTGGATTGTTTTGATTATTTTGTTATCCGTGATGTCAG
  R  N  S  F  A  T  S  W  I  V  L  I  I  L  L  S  V  M  S  A
    3070              3090              3110

CAGGCTTTGGCGTCTGGTATTACAAAAACCATTATGCCCGCAATAAGAAAGGCATAACGG
  G  F  G  V  W  Y  Y  K  N  H  Y  A  R  N  K  K  G  I  T  A
    3130              3150              3170

CTGATGATAAGGCGAAATCGTCAAATGAATAGGCAGCCATTACCCATTATCTGGCAAAGA
  D  D  K  A  K  S  S  N  E  ***  (SEQ ID NO:14)
    3190              3210              3230

TCATTTTTGATCCGTTATCGTATATCCATCCTCAGCGGTTGCAGATAGCGCCGGAAATGA
    3250              3270              3290

TTGTCAGACCGCGCCACGCGAAATGAGTTAATACTGGCGGCATGGCGGCGGCTTAAGAAC
    3310              3330              3350
```

FIG. 9D

```
GGAGAAAAGGAGTGTATTCAAAACTCACTGACGCAGCTGTGGCTGCTCAGTGGCGCCGAC
     3370                3390                3410

TGCCGCAAGTAGCGTATTTACTAAACTGAGAGCCGATCTGGCAAGGCAGGGAGCCTTGCT
     3430                3450                3470

TGGCCTAGCCGGATTGGGCGAAATGAGTTAATACTGGCGGCATGGCGGCTTGCCAT    (SEQ ID NO:10)
     3490                3510                3530
```

FIG. 9E

```
CATAACAACTCCTTAATACTACTTATTATTTACGGTGTGTTTAAACACCT  50
GCAGTACCGATCCGGCATTCAGTTATCGCCACTATGCCGAATCGACAAAA 100
CCACGAATAATTCACCGCTATCGCTCCTGATGTGTTTACTTCCTGAAAGA 150
TATTTTTACTACCGAAGCACTCTATCGCTCATTTAGGTAACCGGTTCTAC 200
AATGTCATCTAACTTTTATAGATTTGAATGCTAATTTTTCTCACGCATAT 250
ATATTTAACAGAAACCATAAAGTGTTTAGCCACTATAGAACAACAAATCA 300
CCCATGCAACATTTTGATATTTAAAGAGAAAATCTCACAACCACATTAAG 350
AAACTTGACACCGTTCGGCTAAAAACATGTCATTAAGCAAACTCGCCATA 400
TAATCAGAACATATCGCATTGTGCTTCACAGTCCTCACGTGACGCTCCAT 450
CCGCAATACGGTTATATGCCATCGCAGGCGCTGTAATCATATTCACGATG 500
ATGCTTAGCACGCTTTATTCCCGCTCCGATTTAATCTTTTAATATATCTA 550
TCAGTTACAACATTTCTTGTTATATTATAAGAATAGAATCAACACCACAA 600
TTCCAACATAAATATCACCTGTGTTTAGAGAGAATTTACATTCCAAAAAA 650
ATAATAACTAACGCAAATATTGAACACGCGATAAAAAAGTCTATTTCGCT 700
ATAAAACCCATTATTATTAAGAGTGGTTAACTCTTCGTTGAATAAAAAAT 750
GTCAATGACGTTCCATAATTCAGGAGATGAACTTCACAAGTCATTATATA 800
TAACAGGAGGTGCTATG 817  (SEQ ID NO:15)
```

FIG. 15

SALMONELLA VACCINES

This application is a continuation-in-part of application Ser. No. 08/271,354, filed on Jul. 6, 1994, U.S. Pat. No. 5,695,983, which in turn is a continuation-in-part of Ser. No. 08/090,526, filed on Jul. 9, 1993, U.S. Pat. No. 5,599,537, which in turn is a continuation-in-part of application Ser. No. 07/629,602 filed on Dec. 18, 1990, now abandoned.

This invention was made with Government support under Grant No. AI30479 and Grant No. 00917 awarded by the National Institutes of Health. The Government has certain rights in the invention.

BACKGROUND OF THE INVENTION

The invention relates to vaccines.

Enteric fevers and diarrheal diseases, e.g., typhoid fever and cholera, are major causes of morbidity and mortality throughout the developing world, Hook et al., 1980, In Harrison's Principles of Internal Medicine, 9th Ed., 641–848, McGraw Hill, New York. Traditional approaches to the development of vaccines for bacterial diseases include the parenteral injection of purified components or killed organisms. These parenterally administered vaccines require technologically advanced preparation, are relatively expensive, and are often, because of dislike for needle-based injections, resisted by patients. Live oral vaccine strains have several advantages over parenteral vaccines: low cost, ease of administration, and simple preparation.

The development of live vaccines has often been limited by a lack of understanding of the pathogenesis of the disease of interest on a molecular level. Candidate live vaccine strains require nonrevertable genetic alterations that affect the virulence of the organism, but not its induction of an immune response. Work defining the mechanisms of toxigenesis of *Vibrio cholerae* has made it possible to create live vaccine strains based on deletion of the toxin genes, Mekalanos et al., 1983, Nature 306:551, Levine et al., 1988, Infect. Immun. 56:161.

Recent studies have begun to define the molecular basis of *Salmonella typhimurium* macrophage survival and virulence, Miller et al., 1989, Proc. Natl. Acad. Sci. USA 86:5054, hereby incorporated by reference. *Salmonella typhimurium* strains with mutations in the positive regulatory regulon phoP are markedly attenuated in virulence for BALB/c mice. The phoP regulon is composed of two genes present in an operon, termed phoP and phoQ. The phoP and phoQ gene products are highly similar to other members of bacterial two-component transcriptional regulators that respond to environmental stimuli and control the expression of a large number of other genes. A mutation at one of these phoP regulatory region regulated genes, pagC, confers a virulence defect. Strains with pagC, phoP, or phoQ mutations afford partial protection to subsequent challenge by wild-type *S. typhimurium*.

Salmonella species cause a spectrum of clinical disease that includes enteric fevers and acute gastroenteritis, Hook et al., 1980, supra. Infections with Salmonella species are more common in immunosuppressed persons, Celum et al., 1987, J. Infect. Dis. 156:998. *S. typhi*, the bacterium that causes typhoid fever, can only infect man, Hook et al., 1980, supra. The narrow host specificity of *S. typhi* has resulted in the extensive use of *S. enteriditis typhimurium* infection of mice as a laboratory model of typhoid fever, Carter et al., 1984 J. Exp. Med. 139:1189. *S. typhimurium* infects a wider range of hosts, causing acute gastroenteritis in man and a disease similar to typhoid fever in the mouse and cow.

Salmonella infections are acquired by oral ingestion. The organisms, after traversing the stomach, replicate in the small bowel, Hornik et al., 1970, N. Eng. J. Med. 283:686. Salmonella are capable of invasion of the intestinal mucosal cells, and *S. typhi* can pass through this mucosal barrier and spread via the Peyer's patches to the lamina propria and regional lymph nodes. Colonization of the reticuloendothelial cells of the host then occurs after bacteremia. The ability of *S. typhi* to survive and replicate within the cells of the human reticuloendothelial system is essential to its pathogenesis, Hook et al., 1980, supra, Hornick et al., 1970, supra, and Carter et al., 1984, supra.

Immunity to *Salmonella typhi* involves humoral and cell-mediated immunity, Murphy et al., 1987, J. Infect. Dis. 156:1005, and is obtainable by vaccination, Edelman et al., 1986, Rev. Inf. Dis. 8:324. Recently, human field trials demonstrated significant protective efficacy against *S. typhi* infection after intramuscular vaccination with partially purified Vi antigen, Lanata et al., 1983, Lancet 2:441. Antibody-dependent enhancement of *S. typhi* killing by T cells has been demonstrated in individuals who received a live *S. typhi* vaccine, indicating that these antibodies may be necessary for the host to generate a cell-mediated immune response, Levine et al., 1987, J. Clin. Invest. 79:888. The cell-mediated immune response is important in typhoid immunity since killed vaccines that do not induce this immune response are not protective in man, Collins et al., 1972, Infect. Immun. 41:742.

SUMMARY OF THE INVENTION

The invention features a bacterial cell having a mutation in the phoQ gene, wherein said mutation attenuates virulence. In various preferred embodiments the mutation is a deletion; the cell has a mutation in the phoP gene; and the bacterial cell is a Salmonella cell.

In even more preferred embodiments the Salmonella cell is a *Salmonella typhimurium* cell; the Salmonella cell is a *Salmonella enteriditis* cell; the Salmonella cell is a *Salmonella pylorum* cell; the Salmonella cell is a *Salmonella paratyphi* A cell; the Salmonella cell is a *Salmonella paratyphi* B cell; the Salmonella cell is a *Salmonella cholerasuis* cell; the Salmonella cell is a *Salmonella typhi* cell.

In other preferred embodiments the mutation in the phoP gene is a deletion. In another preferred embodiment the mutation in the phoP gene is a deletion of at least 5 nucleotides; is a deletion of at least 10 nucleotides; is a deletion of at least 50 nucleotides; is a deletion of at least 100 nucleotides; is a deletion of at least 750 nucleotides.

In another preferred embodiment the mutation in the phoQ gene is a deletion of at least 5 nucleotides; is a deletion of at least 10 nucleotides; is a deletion of at least 50 nucleotides; is a deletion of at least 100 nucleotides; is a deletion of at least 750 nucleotides.

In another preferred embodiment the deletion of the phoQ gene and the deletion of the phoP gene comprise a deletion of nucleotides 376 to 1332 of the phoP/phoQ locus.

In another aspect, the invention features a vaccine which includes the bacterial cell of having a mutation in the phoQ gene which mutation attenuates virulence. In a preferred embodiment the bacterial cell is Ty800.

In other preferred embodiments, the phoQ mutation is a null mutation and the phoP mutation is a null mutation.

The invention provides a Salmonella vaccine which does not cause transient bacteremia. In general, the invention features a bacterial cell, preferably a Salmonella cell, e.g., a S. typhi, S. enteritidis typhimurium, or S. cholerae-suis cell, the virulence of which is attenuated by a first mutation in a phoP regulon and a second mutation in an aromatic amino acid synthetic gene. As used herein, phoP regulon is defined as a DNA which comprises a unit of Salmonella virulence gene expression characterized by two regulatory genes, phoP and phoQ, and structural genes, the expression of which is regulated by phoP and phoQ, e.g., phoP regulatory region repressed genes (prg) or phoP regulatory region activated genes (pag). Such a bacterial cell can be used as a vaccine to immunize a mammal against salmonellosis.

The Salmonella cell may be of any serotype, e.g., S. typhimurium, S. paratyphi A, S. paratyphi B, S. paratyphi C, S. pylorum, S. dublin, S. heidelberg, S. newport, S. minnesota, S. infantis, S. virchow, or S. panama.

The first mutation may be a non-revertable null mutation in the phoP/phoQ locus. Preferably, the mutation is a deletion of at least 100 nucleotides; more preferably, the mutation is a deletion of at least 500 nucleotides; even more preferably, the mutation is a deletion of at least 750 nucleotides; and, most preferably, the mutation is a deletion of nucleotides 376 to 1332 of the phoP/phoQ regulatory locus.

The second mutation may be a non-revertable null mutation in an aroA locus or a non-revertable null mutation in an aroC/aroD locus, or another locus involved in the biosynthesis of aromatic amino acids.

To further attenuate the virulence of the bacterial cell of the invention, the cell may contain yet another mutation, e.g., a deletion, in a non-aromatic amino acid synthetic gene, e.g., a mutation which renders the cell auxotrophic for a non-aromatic amino acid, e.g., histidine. In preferred embodiments, the bacterial cell of the invention is a S. typhi cell with the genotype aroA⁻, his⁻, phoP/phoQ⁻, e.g., TyLH445.

The invention may also include a Salmonella cell, the virulence of which is attenuated by the constitutive expression of a gene under the control of a two-component regulatory system. In preferred embodiments the constitutive expression is the result of a mutation at a component of the two-component regulatory system. In preferred embodiments the bacterial cell includes a second mutation which attenuates virulence.

In yet other preferred embodiments of the vaccine the two-component regulatory system is the phoP regulatory region, and the gene under the control of the two-component system is a phoP regulatory region regulated gene, e.g., a prg gene, e.g., prgA, prgB, prgC, prgE, or prgH, or pag gene, e.g., pagC. In preferred embodiments constitutive expression is the result of a change or mutation, e.g., a deletion, (preferably a non-revertible mutation) at the promoter of the regulated gene or of the phoP regulatory region, e.g., a mutation in the phoQ or the phoP gene, e.g., the phoP$^c$ mutation.

In another aspect, the invention features a vaccine including a bacterial cell which is attenuated by decrease of expression of a virulence gene under control of a phoP regulatory region, e.g., a prg gene, e.g., prgA, prgB, prgC, prgE, or prgH.

In preferred embodiments of the vaccine the Salmonella cell includes a first mutation, e.g., a deletion, which attenuates virulence, e.g., a mutation in a phoP regulatory region gene, e.g., a mutation in the phoP or phoQ gene, e.g., phoP$^c$, or a mutation in a phoP regulatory region regulated gene, and a second mutation which attenuates virulence, e.g., a mutation in an aromatic amino acid synthetic gene, e.g., an aro gene, a mutation in a phoP regulatory region regulated gene, e.g., a mutation in a prg gene, e.g., prgA, prgB, prgC, prgE, or prgH, or pag locus, e.g., a pagC mutation.

In yet other preferred embodiments the bacterial cell includes a first mutation in a phoP regulatory region gene and a second mutation in an aromatic amino acid synthetic gene, e.g., an aro gene.

In another aspect, the invention features a vaccine, preferably a live vaccine, including a bacterial cell, the virulence of which is attenuated by a mutation, e.g., a deletion, in a gene under the control of a two-component regulatory system. In preferred embodiments the bacterial cell includes a virulence attenuating mutation in a second gene, e.g., in an aromatic amino acid synthetic gene, e.g., an aro gene.

In yet other preferred embodiments of the vaccine the bacterial cell is a Salmonella cell, the two-component regulatory system is the phoP regulatory region, and the gene under its control is a prg gene, e.g. prgA, prgB, prgC, prgE, or prgH, or a pag gene, e.g., the pagC gene.

In another aspect the invention features a vaccine, preferably a live vaccine, including a Salmonella cell e.g., a S. typhi, S. enteritidis typhimurium, or S. cholerae-suis cell, including a first virulence attenuating mutation in an aromatic amino acid biosynthetic gene, e.g., an aro gene, and a second virulence attenuating mutation in a phoP regulatory region gene, e.g., a phoP⁻ mutation.

In another aspect the invention features a bacterial cell, or a substantially purified preparation thereof, preferably a Salmonella cell, e.g., a S. typhi, S. enteritidis typhimurium, or S. cholerae-suis cell, which constitutively expresses a gene under the control of a two-component regulatory system and which includes a virulence attenuating mutation, e.g., a deletion, which does not result in constitutive expression of a gene under the control of the two-component regulatory system. In preferred embodiments the bacterial cell includes a mutation in a component of the two-component regulatory system.

In preferred embodiments the bacterial cell is a Salmonella cell which expresses a phoP regulatory region regulated gene constitutively (the constitutive expression preferably caused by a mutation, preferably a non-revertible mutation, e.g., a deletion in the phoP regulatory region, e.g., a mutation in the phoQ or phoP gene, e.g., phoP$^c$), and which includes a virulence attenuating mutation, preferably a non-revertible mutation, e.g., a deletion, preferably in an aromatic amino acid synthetic gene, e.g., an aro gene, or in a phoP regulatory region regulated gene, e.g., a prg gene, e.g., prgA, prgB, prgC, prgE, or prgH or pag gene, e.g., pagC which does not result in the constitutive expression of a gene under the control of the phoP regulatory region.

In another aspect, the invention features a bacterial cell, or a substantially purified preparation thereof, e.g., a Salmonella cell, e.g., a S. typhi cell, an S. enteritidis typhimurium or a S. cholerae-suis cell, including a virulence attenuating mutation in a gene regulated by a two-component regulatory system. In preferred embodiments the virulence attenuating mutation is in a phoP regulatory region regulated gene, e.g., a prg gene, e.g., prgA, prgB, prgC, prgE, or prgH or pag gene, e.g., pagC.

In preferred embodiments the bacterial cell includes a second mutation, e.g., in an aromatic amino acid synthetic gene, e.g., an aro gene, in a phoP regulatory region gene, e.g., the phoP or phoQ genes, or in a phoP regulating region regulated gene, e.g., a prg gene, e.g., prgA, prgB, prgC, prgE, or prgH or a pag gene, e.g., pagC, which attenuates virulence but which does not result in constitutive expression of a phoP regulatory region regulated gene.

The invention also features a live Salmonella cell, or a substantially purified preparation thereof, e.g., a *S. typhi, S. enteriditis typhimurium*, or *S. cholerae-suis* cell, in which there is inserted into a virulence gene, e.g., a gene in the phoP regulating region, or a phoP regulating region regulated gene, e.g., a prg gene, e.g., prgA, prgB, prgC, prgE, or prgH or a pag locus, e.g., pagC, a gene encoding a heterologous protein, or a regulatory element thereof.

In preferred embodiments the live Salmonella cell carries a second mutation, e.g., an aro mutation, e.g., an aroA mutation, e.g., aroA⁻ or aroADEL407, that attenuates virulence.

In preferred embodiments the DNA encoding a heterologous protein is under the control of an environmentally regulated promoter. In other preferred embodiments the live Salmonella cell further includes a DNA sequence encoding T7 polymerase under the control of an environmentally regulated promoter and a T7 transcriptionally sensitive promoter, the T7 transcriptionally sensitive promoter controlling the expression of the heterologous antigen.

The invention also features a vector capable of integrating into the chromosome of Salmonella including: a first DNA sequence encoding a heterologous protein; a second (optional) DNA sequence encoding a marker e.g., a selective marker, e.g., a gene that confers resistance for a heavy metal resistance or a gene that complements an auxotrophic mutation carried by the strain to be transformed; and a third DNA sequence, e.g., a phoP regulon encoded gene, e.g., a prg gene, e.g., prgA, prgB, prgC, prgE, or prgH or a pag locus, e.g., pagC, encoding a phoP regulatory region regulated gene product necessary for virulence, the third DNA sequence being mutationally inactivated.

In other preferred embodiments: the first DNA sequence is disposed on the vector so as to mutationally inactivate the third DNA sequence; the vector cannot replicate in a wild-type Salmonella strain; the heterologous protein is under the control of an environmentally regulated promoter; and the vector further includes a DNA sequence encoding T7 polymerase under the control of an environmentally regulated promoter and a T7 transcriptionally sensitive promoter, the T7 transcriptionally sensitive promoter controlling the expression of the heterologous antigen.

In another aspect the invention includes a method of vaccinating an animal, e.g., a mammal, e.g., a human, against a disease caused by a bacterium, e.g., Salmonella, including administering a vaccine of the invention.

The invention also includes a vector including DNA which encodes the pagC gene product; a cell transformed with the vector; a method of producing the pagC gene product including culturing the transformed cell and purifying the pagC gene product from the cell or culture medium; and a purified preparation of the pagC gene product.

In another aspect the invention includes a method of detecting the presence of Salmonella in a sample including contacting the sample with pagC encoding DNA and detecting the hybridization of the pagC encoding DNA to nucleic acid in the sample.

The invention also includes a vector including DNA which encodes the prgH gene product; a cell transformed with the vector; a method of producing the prgH gene product including culturing the transformed cell and purifying the prgH gene product from the cell or culture medium; and a purified preparation of the prgH gene product.

In another aspect the invention includes a method of detecting the presence of Salmonella in a sample including contacting the sample with prgH encoding DNA and detecting the hybridization of the prgH encoding DNA to nucleic acid in the sample.

In another aspect the invention features a method of attenuating the virulence of a bacterium, the bacterium including a two-component regulatory system, including causing a gene under the control of the two-component system to be expressed constitutively. In preferred embodiments the bacterium is Salmonella, e.g., *S. typhi, S. enteritidis typhimurium*, or *S. cholerae-suis*, and the two-component system is the phoP regulatory region.

In yet another aspect, the invention features a substantially pure DNA which includes the sequence given in SEQ ID NO:5 or a fragment thereof.

The invention also includes a substantially pure DNA which includes a sequence encoding pagD, e.g., nucleotides 91 to 354 of SEQ ID NO:5 (pagD open reading frame (ORF)) and degenerate variants thereof that encode a product with essentially the amino acid sequence given in SEQ ID NO:6, as well as the pagD ORF and its 5' non-coding region, nucleotides 4 to 814 of SEQ ID NO:15) which contains the pagD promoter. DNA in the region between the pagC ORF and the pagD ORF (nucleotides 4 to 814 of SEQ ID NO:15), DNA which includes the pagC promoter (nucleotides 562 to 814 of SEQ ID NO:15), and DNA which includes the pagD promoter alone (nucleotides 4 to 776 of SEQ ID NO:15) are also within the claimed invention.

The invention also includes a substantially pure DNA which includes a sequence encoding envE, e.g., nucleotides 1114 to 1650 of SEQ ID NO:5 (envE ORF) and degenerate variants thereof that encode a product with essentially the amino acid sequence given in SEQ ID NO:7.

Another aspect of the invention features a substantially pure DNA which includes a sequence encoding msgA, e.g., nucleotides 1825 to 2064 of SEQ ID NO:5 (msgA ORF) and degenerate variants thereof which encode a product with essentially the amino acid sequence given in SEQ ID NO:8, as well as the msgA ORF with its 5' non-coding region, nucleotides 1510 to 1824 of SEQ ID NO:5 which contains the msgA promoter. Also within the invention is a substantially pure DNA comprising the msgA promoter alone (nucleotides 1510 to 1760 of SEQ ID NO:5).

In yet another aspect, the invention features a substantially pure DNA which includes a sequence encoding envF, e.g., nucleotides 2554 to 3294 of SEQ ID NO:5 (envF ORF) and degenerate variants thereof which encode a product with essentially the amino acid sequence given in SEQ ID NO:9, as well as the envF ORF with its 5' non-coding region, nucleotides 2304 to 2553 of SEQ ID NO:5 containing the envF promoter.

Also within the invention is a substantially pure DNA which includes the sequence given in SEQ ID NO:10 or a fragment thereof.

The invention also includes a substantially pure DNA which includes a sequence encoding PrgH, e.g., nucleotides 688 to 1866 of SEQ ID NO:10 (prgH ORF) and degenerate variants thereof which encode a product with essentially the amino acid sequence given in SEQ ID NO:11, as well as the prgH ORF with its promoter region (nucleotides 1 to 689 of SEQ ID NO:10).

The invention also includes a substantially pure DNA which includes a sequence encoding PrgI, e.g., nucleotides 1891 to 2133 of SEQ ID NO:10 (prgI ORF) and degenerate variants thereof which encode a product with essentially the amino acid sequence given in SEQ ID NO:12, as well as the prgI ORF with its promoter region (nucleotides 1 to 689 of SEQ ID NO:10.

In another aspect, the invention features a substantially pure DNA which includes a sequence encoding PrgJ, e.g., nucleotides 2152 to 2457 of SEQ ID NO:10 (prgJ ORF) and degenerate variants thereof which encode a product with essentially the amino acid sequence given in SEQ ID NO:13, as well as the prgJ ORF and its promoter region (nucleotides 1 to 689 of SEQ ID NO:10.

In yet another aspect, the invention features a substantially pure DNA which includes a sequence encoding PrgK, e.g., nucleotides 2456 to 3212 of SEQ ID NO:10 (prgK ORF) and degenerate variants thereof which encode a product with essentially the amino acid sequence given in SEQ ID NO:14, as well as the prgK ORF with its promoter region (nucleotides 1 to 689 of SEQ ID NO:10.

The invention also encompasses a bacterial cell the virulence of which is attenuated by a mutation, e.g., a deletion, in one or more genes selected from the group consisting of pagD, pagE, pagF, pagG, pagH, pagI, pagJ, pagK, pagL, pagM, pagN, pagP, envE, and envF. Also included is a bacterial cell which is attenuated by a mutation, e.g., a deletion, in one or more genes selected from the group consisting of pagC, pagD, pagJ, pagE, pagM, and msgA. A bacterial cell, the virulence of which is attenuated by a mutation, e.g., a deletion, in one or more genes selected from the group consisting of prgH, prgI, prgJ, and prgK is also within the claimed invention.

Two-component regulatory system, as used herein, refers to a bacterial regulatory system that controls the expression of multiple proteins in response to environmental signals. The two-components referred to in the term are a sensor, which may, e.g., sense an environmental parameter and in response thereto promote the activation, e.g. by promoting the phosphorylation, of the second component, the activator. The activator affects the expression of genes under the control of the two-component system. A two-component system can include, e.g., a histidine protein kinase and a phosphorylated response regulator, as is seen in both gram positive and gram negative bacteria. In *E. coli*, e.g., 10 kinases and 11 response regulators have been identified. They control chemotaxis, nitrogen regulation, phosphate regulation, osmoregulation, sporulation, and many other cellular functions, Stock et al., 1989 Microbiol. Rev. 53:450–490, hereby incorporated by reference. A two-component system also controls the virulence of *Agrobacterium tumefasciens* plant tumor formation, Leroux et al. EMBO J 6:849–856, hereby incorporated by reference). Similar virulence regulators are involved in the virulence of *Bordetella pertussis* Arico et al., 1989, Proc. Natl. Acad. Sci. USA 86:6671–6675, hereby incorporated by reference, and *Shigella flexneri*, Bernardini et al., 1990, J. Bact. 172:6274–6281, hereby incorporated by reference.

Environmentally regulated, as used herein refers to a pattern of expression wherein the expression of a gene in a cell depends on the levels of some characteristic or component of the environment in which the cell resides. Examples include promoters in biosynthetic pathways which are turned on or off by the level of a specific component or components, e.g., iron, temperature responsive promoters, or promoters which are expressed more actively in specific cellular compartments, e.g., in macrophages or vacuoles.

A vaccine, as used herein, is a preparation including materials that evoke a desired biological response, e.g., an immune response, in combination with a suitable carrier. The vaccine may include live organism, in which case it is usually administered orally, or killed organisms or components thereof, in which case it is usually administered parenterally. The cells used for the vaccine of the invention are preferably alive and thus capable of colonizing the intestines of the inoculated animal.

A mutation, as used herein, is any change (in comparison with the appropriate parental strain) in the DNA sequence of an organism. These changes can arise e.g., spontaneously, by chemical, energy e.g., X-ray, or other forms of mutagenesis, by genetic engineering, or as a result of mating or other forms of exchange of genetic information. Mutations include e.g., base changes, deletions, insertions, inversions, translocations or duplications.

A mutation attenuates virulence if, as a result of the mutation, the level of virulence of the mutant cell is decreased in comparison with the level in a cell of the parental strain, as measured by (a) a significant (e.g., at least 50%) decrease in virulence in the mutant strain compared to the parental strain, or (b) a significant (e.g., at least 50%) decrease in the amount of the polypeptide identified as the virulence factor in the mutant strain compared to the parental strain.

A non-revertible mutation, as used herein, is a mutation which cannot revert by a single base pair change, e.g., deletion or insertion mutations and mutations that include more than one lesion, e.g., a mutation composed of two separate point mutations.

The phoP regulatory region, as used herein, is a two-component regulatory system that controls the expression of pag and prg genes. It includes the phoP locus and the phoQ locus.

phoP regulatory region regulated genes, as used herein, refer to genes such as pag and prg genes.

pag, as used herein, refers to a gene which is positively regulated by the phoP regulatory region.

prg, as used herein, refers to a gene which is negatively regulated by the phoP regulatory region.

An aromatic amino acid synthetic gene, as used herein, is a gene which encodes an enzyme which catalyzes a step in the synthesis of an aromatic amino acid. aroA, aroC, and aroD are examples of such genes in Salmonella. Mutations in these genes can attenuate virulence without the total loss of immunogenicity.

Abnormal expressions, as used herein, means expression which is higher or lower than that seen in wild type.

Heterologous protein, as used herein, is a protein that in wild type, is not expressed or is expressed from a different chromosomal site, e.g., a heterologous protein is one encoded by a gene that has been inserted into a second gene.

Virulence gene, as used herein, is a gene the inactivation of which results in a Salmonella cell with less virulence than that of a similar Salmonella cell in which the gene is not inactivated. Examples include the phoP, pagC, prgH genes.

A marker, as used herein, is gene product the presence of which is easily determined, e.g., a gene product that confers resistance to a heavy metal or a gene product which allows or inhibits growth under a given set of conditions.

Purified preparation, as used herein, is a preparation, e.g., of a protein, which is purified from the proteins, lipids, and other material with which it is associated. The preparation is preferably at least 2–10 fold purified.

Constitutive expression, as used herein, refers to gene expression which is modulated or regulated to a lesser extent than the expression of the same gene in an appropriate control strain, e.g., a parental or in wild-type strain. For example, if a gene is normally repressed under a first set of conditions and derepressed under a second set of conditions constitutive expression would be expression at the same level, e.g., the repressed level, the derepressed level, or an intermediate level, regardless of conditions. Partial constitutive expression is included within the definition of constitutive expression and occurs when the difference between two levels of expression is reduced in comparison in what is seen in an appropriate control strain, e.g., a wild-type or parental strain.

A substantially purified preparation of a bacterial cell is a preparation of cells wherein contaminating cells without the desired mutant genotype constitute less than 10%, preferably less than 1%, and more preferably less than 0.1% of the total number of cells in the preparation.

The invention allows for the attenuation of virulence of bacteria and of vaccines that include bacteria, especially vaccines that include live bacteria, by mutations in two-component regulatory systems and/or in genes regulated by these systems. The vaccines of the invention are highly attenuated for virulence but retain immunogenicity, thus they are both safe and effective.

The vectors of the invention allow the rapid construction of strains containing DNA encoding heterologous proteins, e.g., antigens. The heterologous protein encoding DNA is chromosomally integrated, and thus stable, unlike plasmid systems which are dependent on antibiotic resistance or other selection pressure for stability. Live Salmonella cells of the invention in which the expression of heterologous protein is under the control of an environmentally responsive promoter do not express the heterologous protein at times when such expression would be undesirable e.g., during culture, vaccine preparation, or storage, contributing to the viability of the cells, but when administered to humans or animals, express large amounts of the protein. This is desirable because high expression of many heterologous proteins in Salmonella can be associated with toxicity to the bacterium. The use of only a single integrated copy of the DNA encoding the heterologous protein also contributes to minimal expression of the heterologous protein at times when expression is not desired. In embodiments where a virulence gene, e.g., the pagC gene or the prgH gene, contains the site of integration for the DNA encoding the heterologous protein the virulence of the organism is attenuated.

A substantially pure DNA, as used herein, refers to a nucleic acid sequence, segment, or fragment, which has been purified from the sequences which flank it in a naturally occurring state, e.g., a DNA which has been removed from the sequences which are normally adjacent to the fragment, e.g., the sequences adjacent to the fragment in the genome in which it naturally occurs. The term also applies to DNA which has been substantially purified from other components which naturally accompany the DNA, e.g., DNA which has been purified from proteins which naturally accompany it in a cell.

Other features and advantages of the invention will be apparent from the following description of the preferred embodiments and from the claims.

DESCRIPTION OF THE PREFERRED EMBODIMENTS

The drawings will first be described.
Drawings
FIG. 1 is a graph of the survival of Salmonella strains within macrophages.
FIG. 2 is a map of the restriction endonuclease sites of the pagC locus.

FIGS. 3A–3B depict a map of the DNA sequence of the pagC region (SEQ ID NO:1).

FIG. 4 is a map of the location of prgH within the hil locus. The arrows indicate the direction of orientation of the neomycin promoter of Tn5B50 insertions within the hil locus and the direction of transcription of the PrgH1::TnphoA fusion protein. Restriction endonuclease sites are represented by B, BamH1; H, HindIII; X, XhoI; S, SacI; V, EcoRV.

FIGS. 5A–5B depict a DNA sequence from the prgH gene (plasmid pIB01) (SEQ ID NO:3).

FIG. 6 is a bar graph showing a comparison of the sensitivity of wild type (ATCC 14028), phoP-null mutant (CS015), and pag::TnphoA mutant strains to NP-1 defensin. The y-axis represents the Defensin Killing Index (DKI) which is a measure of bacteria killed on exposure to NP-1. The DKI is defined as the logarithmic function of the ratio of control bacteria to surviving bacteria incubated with NP-1 [DKI=log (CFU without NP-1/CFU with NP-1)]. The individual bars represent the mean and standard error of five separate experiments. The x-axis indicates the allele mutated. The mean DKI for each of the pag::TnphoA strains tested was determined not be different from that of wild type Salmonella. ($P<0.05$). In contrast, the phoP mutant was significantly different ($P<0.0001$).

FIG. 7 is a diagram showing a partial physical map of the restriction endonuclease sites of the pagC chromosomal region. The mouse 50% lethal doses ($LD_{50}$) for strains with transposon insertions in pagD, envE, msgA, and pagC are shown above each gene. Horizontal arrows demonstrate the direction of transcription. Vertical arrows denote TnphoA insertions and the hollow triangle denotes a MudJ insertion. Below the chromosomal map is a representation of the DNA insert in plasmid pCAA9, which was mutagenized with TnphoA and MudJ. Letter designations: A, AccI; C, ClaI; E, EcoRI; H, HpaI; P, PstI; and V, EcoRV.

FIGS. 8A–8C depict a DNA sequence of the region upstream of pagC and the translation of each ORF. The HpaI and ClaI sites at the beginning and end of the region are indicated. Shine-Delgarno regions are underlined and stem loop structures (potential Rho-independent terminators) are indicated with a line below and above the sequence. Arrow heads denote the location of the representative transposon insertion within each gene. Horizontal arrows in the pagD and msgA promoter regions mark the transcriptional start sites, and asterisks mark the −10 and −35 sequences. The consensus lipid attachment site in EnvF is enclosed in brackets. The pagD ORF begins at nucleotide 91 and ends at nucleotide 354 of SEQ ID NO:5; the envE ORF begins at nucleotide 1114 and ends at nucleotide 1650 of SEQ ID NO:5; the msgA ORF begins at nucleotid 1825 and ends at nucleotide 2064 of SEQ ID NO:5; and the envF ORF begins at nucleotide 2554 and ends at nucleotide 3294 of SEQ ID NO:5.

FIGS. 9A–9E depict a DNA sequence containing the prgH, prgI, prgJ, and prgK genes. The start codon (ATG) of each gene is underlined, and the stop codon is indicated with an asterisk. The prgH ORF begins at nucleotide 688 and ends at 1866 of SEQ ID NO:10; the prgI ORF begins at nucleotide 1891 and ends at nucleotide 2133 of SEQ ID NO:10; the prgJ ORF begins at nucleotide 2152 and ends at nucleotide 2457 of SEQ ID NO:10; and the prgK ORF begins at nucleotide 2454 and ends at 3212 of SEQ ID NO:10.

Figure 1:
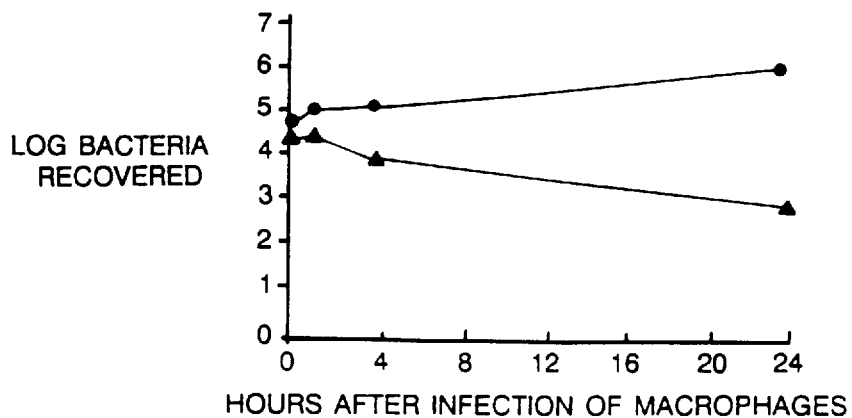

FIG. 15 is a DNA sequence containing the pagC-pagD intergenic region. pagC translational start site (ATG on the opposite DNA strand) is underlined (nucleotides 1–3 of SEQ ID NO:15). The pagC transcriptional start (nucleotide 562) is indicated with an arrow pointing left. The pagD translational start (ATG) is underlined (nucleotides 815–817 of SEQ ID NO:15). The pagD transcriptional start is indicated with an arrow pointing right (nucleotide 776).

Strain Deposit

Under the terms of the Budapest Treaty on the International Recognition of the Deposit of Microorganisms for the Purpose of Patent Procedure, deposit of the following materials has been made with the American Type Culture Collection (ATCC) of Rockville, Md., USA.

Applicant's assignee, Massachusetts General Hospital, represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 U.S.C. §122. The deposited material will be maintained with all the care necessary to keep it viable and uncontaminated for a period of at least five years after the most recent request for the furnishing of a sample of the deposited plasmid, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

Phop$^c$ strain CS022 (described below) has been deposited with the American Type Culture Collection (Rockville, Md.) and has received ATCC designation 55130.

The plasmid, pIB01, containing the prgH gene has been deposited on Jul. 9, 1993 with the American Type Culture Collection (Rockville, Md.) and has received ATCC designation ATCC 75496.

Vaccine Having a phoP/phoQ Deletion

The phoP/phoQ virulence regulatory genes of Salmonella typhimurium were deleted in Salmonella typhi Ty2 and the resultant strain (Ty800) was tested as a live, attenuated typhoid fever vaccine in human volunteers. Groups of 2–3 volunteers received single oral doses of $10^7$, $10^8$, $10^9$, or $10^{10}$ colony forming units. Two volunteers receiving the largest dose had self-limited side effects; significantly, no bacteremias were detected. Ten of 11 volunteers had evidence of intestinal immune responses to the vaccine as measured by increases in *S. typhi* lipopolysaccharide-specifc IgA-secreting cells detected in peripheral blood samples. Humoral immune responses were measured and compared to control vaccinees who received 4 oral doses of *S. typhi* Ty21a. In the most sensitive assays, 9/11 volunteers and 5/8 Ty21a control vaccinees had evidence of IgG directed against *S. typhi* antigens. These experiments demonstrate that Ty800 is safe and single oral doses are highly immunogenic in human volunteers.

A major advantage of Ty800 appears to be the large doses which may be delivered orally without development of bacteremias, suggesting that this strain may be particularly well suited for engineering as a live vector for delivery of heterologous antigens to the gastrointestinal lymphoid tissue.

Typhoid fever remains a worldwide health problem [1]. Ty21a is an FDA-approved, live attenuated oral typhoid fever which confers approximately 60–70% protective efficacy in endemic areas (for review see Levine, Typhoid Fever Vaccines, in Vaccines, Plotkin et al., eds. W. B. Sanders: Philadelphia. p. 597–633). At least 3 doses of Ty21a are required to achieve such rates of efficacy (Levine, supra), and protection may be lower in naive populations (Hirschell et al., Eur. J. Clin. Microbiol. 4:925, 1986; Schwartz et al., Arch. Intern. Med. 150:349, 1990). Development of a live attenuated, single dose, oral typhoid fever vaccine could significantly improve public health.

Creation of a defined genetic deletion of the phoP/phoQ genes in the aromatic amino acid auxotrophic *S. typhi* 514Ty (Ty2 DaroA) resulted in strain TyLH445. This candidate vaccine strain was non-reactogenic in human volunteers receiving 2 oral doses of $5\times10^{10}$ colony forming units (cfu) but poorly immunogenic, as only 2/14 volunteers receiving 2 maximal doses developed significant serological responses to *S. typhi* antigens. An *S. typhi* Ty2 strain deleted only for the phoP/phoQ genes (Ty800) was constructed in an attempt to provide a more effective vaccine.

Construction of Ty800

*S. typhi* Ty2 was used as the parent strain for construction of Ty800. A defined chromosomal deletion of 956 base pairs in the contiguous phoP and phoQ genes was created as previously described above (nucleotides 376–1332 of the published sequence: Miller et al., *Proc. Nat'l Acad. Sci.* 86:5054, 1989). Briefly, a 2.2 kb fragment of *S. typhimurium* DNA internally deleted for 956 base pairs (phoP/phoQ D956) was cloned into the suicide vector pCVD442 (Blofield et al., *Mol. Micro.* 5:1447, 1991; Donnenberg et al., *Infect. Immun.* 59:4310, 1991) and maintained in the permissive host *E. coli* SM10 l pir. The resultant suicide vector was mobilized via conjugal transfer to the chromosome of Ty2, using plasmid-encoded ampicillin resistance and the leucine, threonine, and thiamine auxotrophies of *E. coli* SM10 l pir for selection. Subsequently, selection against the vector-encoded sacB gene on sucrose agar plates was used as previously described (Donnenberg, supra) to identify *S. typhi* clones which had eliminated plasmid sequences via a second homologous recombination event, reconstituting either a wild type or deleted phoP/phoQ locus. Clones containing the phoP/phoQ D956 locus were easily recognized as white colonies on indicator plates containing the phosphatase substrate 5-bromo-4-choloro-3-indolyl phosphate, or BCIP (the nonspecific acid phosphatase of Salmonellae, encoded by the phoN gene, is regulated by the phoP/phoQ loci and is responsible for most of the blue coloration of *S. typhi* Ty2 on this indicator plate; Kier et al., *J. Bacteriol.*138:155, 1979). Several white clones were characterized by Southern blotting of chromosomal DNA to demonstrate the anticipated chromosomal deletion in the phoP/phoQ genes and one was designated Ty800.

Preparation of vaccine inocula Stock cultures of Ty800 were stored at −70° C. in 20% glycerol and thawed for growth of Luria broth agar plates for indentification and confirmation of species (by agglutination with antisera) and phenotype on BCIP plates prior to growth inocula. Multiple colonies identified as correct were subsequently inoculated into Luria broth and growth for 16 hours at 37° C. on a rotary shaker. This culture was then suspended in 0.9% saline, standarized spectophotometrically, and diluted as needed in saline to attain the appropriate number of viable colony forming units (cfu) in 35 ml. A sample of each inoculum was diluted and plated for determination of the exact cfu delivered at each log dose.

Human volunteers and study protocol

Healthy adult men and women ages 18–49 with no prior history of typhoid fever vaccination were screened for health status with a complete medical history and physical exam. Laboratory screening tests included complete blood counts, chemistry panel, HIV, hepatitis and syphilis serologies, urinalysis, chest radiography and stool culture and ova and parasite exam. Volunteers were admitted to the General Clinical Research Center at Massachusetts General Hospital between April and September of 1995. Volunteers received a single oral inoculum on the day of admission (study day 0) and were followed in hospital for 14 subsequent days. Volunteers were examined daily by a physician and vital signs were taken every 6 hours. Blood was drawn for serologies at the screening visit and study days 0, 7, 14, 21, and 28. Blood was drawn routinely for peripheral blood mononuclear cell (PBMC) isolations on study days 0 and 7, and on days 4 and 10 for some individuals. Twelve volunteers enrolled in the study and received vaccine. A fourth volunteer in the highest dose group was excluded from further study when *Salmonella brandenberg* was isolated from two stool samples shortly after receiving the experimental vaccine. This organism had not been detected in a stool culture obtained at pre-study screening visit 10 days prior to admission, nor on the first 5 daily inpatient stool cultures. This volunteer was formally excluded from the study thereafter, as evidence of active enteric infection was an exclusion criterion. This individual completed the inpatient observation period, felt completely well, but did not return for serology collections. This volunteer denied recent gastrointestinal illness but was presumably asymptomatically infected with *S. Brandenburg* at some point in the past and intermittently excreting this organism at very low levels. Ty21a vaccinees were a group of microbiology laboratory workers. This group received 4 Ty21a capsules (Swiss Serum and Vaccine Institute, Berne, Switzerland) on alternate days (1–6×10$^9$ cfu viable organisms and 5–50×10$^9$ non viable bacterial cells per capsule) as directed by the manufacturer.

Bacteriology

Bacteriology specimens were processed in the Clinical Microbiology Laboratory of Massachusetts General Hospital. A single daily stool culture was obtained from each volunteer. Stools were planted both as primary cultures and after overnight enrichment in selenite-F broth on Hektoen enteric agar and MacConkey agar plates. Quantitative stool cultures were performed on some volunteers by dissolution and serial dilution of 0.5–1.0 g of stool in phosphate buffered saline and plating on selective media. On study days 2, 4, 6, 8, and 10, two sets of blood cultures were collected from each volunteer and inoculated into Bactec (Becton Dickinson, Sparks, Md.) aerobic and anaerobic blood culture bottles (5 ml inoculum per bottle). Blood cultures were held for 7 days.

Immunological assays

ELISPOT analysis: Sterile ELISA plates with nitrocellulose membrane bottoms (Millititer HA, Millipore) were used in assays designed to enumerate the number of peripheral blood IgA antibody-secreting cells (ASC) (Forrest et al., *Lancet* 1:81, 1988; Kantele et al., J. Infect. Dis. 153:1126, 1986) directed against *S. typhi* lipopolysaccharide (LPS). Membranes were incubated overnight with either 50 mM sodium carbonate buffer (pH 10) alone, or buffer with LPS from *S. typhi* or *Vibrio cholerae*, the latter as a control LPS antigen (both at 20 ug/ml, Sigma, St. Louis, Mo.). Plates were then blocked with phosphate buffered saline (PBS) containing 2% bovine serum albumin (BSA) overnight and subsequently rinsed 3 times with PBS. Peripheral blood mononuclear cells (PBMC) were isolated from 16 ml of citrated blood utilizing Vacutainer Cell Preparation Tubes (Becton-Dickinson, Franklin Lakes, N.J.) as directed by the manufacuturer; 1–2×10$^7$ PBMC were consistently obtained per draw. PBMC were washed three times with PBS, counted, and suspended at known concentrations in RPMI tissue culture medium (Mediatech, Herndon, Va.) containing 10% fetal calf serum and 1% penicillin/streptomycin solution (Sigma). Duplicate aliquots of 1×10$^6$ PBMC and serial 5-fold dilutions of these aliquots were applied to membrane bottom wells treated with the various antigens and incubated for 4 hours in a tissue culture incubator. Non-adherent cells were removed by washing wells with PBS (3 times) and PBS containing 0.05% Tween 20 (Sigma) (3 times). Goat anti-human IgA conjugated to peroxidase (Kirkegaard and Perry Laboratories, Gaithersburg, Md.) was applied at a dilution of 1:2500 in PBS-2% BSA, incubated overnight at 4° C., and plates were subsequently washed with PBS/0.05% Tween 20 (5 times) and then with PBS (three times). Membranes were developed for 15 minutes with 3-amino-9-ethyl-carbazole substrate (AEC, Sigma) in 0.1M acetate buffer at pH 5 as directed by the manufacturer. Dry membranes were then punched out of the ELISA wells using a cork borer and brown/red spots representing IgA-bearing cells specifically bound to antigen-coated membranes were counted at the most appropriate dilution under 20×magnification. Numbers reported represent the mean value for duplicate wells at an appropriate dilution for counting.

Serological analyses

ELISAs were used to measure increases in serum IgG directed against either whole Ty800 vaccine organisms or *S. typhi* O antigen (DIFCO, Detroit, Mich.). The same protocol was used to measure increases in serum IgA directed against *S. typhi* LPS (coating solution 5 µg/ml LPS) and serum IgG directed against purified Vi antigen (gift of Dr. Tim Barnett, CDC, Atlanta, Ga.; coating solution 2 ug/ml). In each of these assays, a standard serum dilution of 1:80 was used, and each diluted serum sample was applied in parallel to wells containing either buffer alone or buffer containing antigen. Affinity purified, alkaline phosphatase-labelled goat antihuman IgG or antihuman IgA secondary antibodies (Kirkegaard and Perry Laboratories) were used. Specific optical density (OD) was determined for each serum sample by subtracting the OD value of the buffer well from the antigen well. Increases in specific OD from preimmune to peak values were obtained by subtracting the preimmune value from values on subsequent days. Significant optical density increases were those which exceed a statisitically derived significant OD threshold (0.22 OD units for the whole cell IgG assay, 0.13 OD units for the O antigen IgG assay, and 0.07 OD units for the LPS IgA assay). These threshold values were determined by testing pre- and post-immune paired sera from 15 volunteers receiving a live attenuated cholera vaccine and are equal to the mean net increase in OD plus 3 standard deviations of these paired sera. To provide another measurement of serological response, endpoint dilution studies were performed using S. typhi LPS. In these studies, 5 μg/ml S. typhi LPS was used for coating antigen wells, and sera were serially diluted 2-fold in PBS/2% BSA in a microtiter plate beginning at 1:40. The endpoint titer was defined as the highest serum dilution at which specific optical density exceeded 0.15 OD units, and more than a four fold increase in titer from preimmune to peak was deemed significant. The Widal tube test using H antigen was performed as directed by the manufacturer (DIFCO). Fishers exact T-test was used to generate p values for comparison between Ty800 and Ty21a vaccinees.

In vitro characterization of Ty800

Chromosomal DNA of Ty800 was demonstrated by restriction endonuclease digestion and Southern blotting to contain the anticipated chromosomal deletion in the phoP and phoQ genes. Ty800 had a growth rate in Luria broth identical to that of the Ty2 parent strain as measured by serial determinations of $OD_{600}$ values for cultures in logarithmic growth phase. Ty800 was more sensitive to rabbit defensin NP-1 than Ty2, a phenotype of other PhoP/PhoQ null Salmonella strains (Miller et al., Infect. Immunol. 58:3706–3710, 1990).

Clinical response and side effects

Following vaccination 9/11 volunteers remained completely well and had no temperature elevations or other adverse effects. Two volunteers receiving the highest dose of $4 \times 10^{10}$ had transient side effects. Volunteer number 9 had a single temperature elevation of 37.9° C. approximately 20 hours after receiving the vaccine, associated with one loose stool and myalgias. He felt completely well within another 12 hours and had no other adverse effects for the duration of the study. Volunteer number 10 had a single temperature elevation to 38° C. also at 20 hours after vaccination, and also had an acute gastroenteritis-like picture with 10 loose to liquid stoods (grade 3–4) during the time period of 12–36 hours following vaccination. Loose stools were associated with cramping; there was no vomiting or bloody stools. This syndrome resolved without therapy within 48 hours after vaccination and the volunteer felt well for the remainder of the study. The excluded volunteer with nontyphoidal felt completely well throughout the hospital stay.

Bacteriology

No volunteer had blood cultures positive for the vaccine organism at any time in the study (10 sets/volunteer). Limiting dilution studies using strain Ty800 and sterile human blood demonstrated that the blood culture system utilized was very sensitive. Blood culture bottles consistently turned positive within 48 hours after introduction of experimental inocula calculated to deliver 1 organism as measured by parallel plating on Luria broth agar plates.

The vaccine organism was detected in stool cultures in 10/11 volunteers. Volunteer number 2 (1 of 2 receiving the lowest dose) had no positive stool cultures. The duration of positive stool cultures ranged from 1–3 days after vaccination in 9 volunteers. Volunteer number 3 who received a dose of $6 \times 10^8$ cfu had positive cultures on days 1, 2, and 3 and then intermittently positive stool cultures only after selenite enrichment until day 15 of the study. This volunteer was completely asymptomatic during this time and received a 7 day course of oral ciprofloxacin to eradicate the vaccine organism, which was documented as successful by multiple negative followup stool cultures over the ensuing month. Quantitative stool cultures performed only on volunteers receiving the highest 2 doses showed that vaccine organism burdens ranged from $10^2$–$10^5$ cfu/gram of stool ($8 \times 10^9$ cfu cohort) to $10^2$–$10^7$ cfu/gram ($4 \times 10^{10}$ cfu cohort). The largest detectable numbers of vaccine organisms occurred on days 1 and 2 after vaccination and decreased rapidly thereafter. Vaccine organisms recovered from volunteers retained their PhoP null phenotype on BCIP plates (see above).

Immunological analyses

All volunteers, except number 1, who received the lowest dose, had significant numbers of IgA-bearing cells directed against S. typhi LPS detected in their peripheral blood on day 7 after vaccination (Table 1A). Control studies performed on day 0 and control wells containing buffer alone or V. cholerae LPS on days 0 and 7 were negative in all cases (<2 spots per well with the highest inoculum of cells). Additional ELISPOT studies performed on days 4 and 10 for the 2 lower dose groups showed that IgA secreting cell numbers were maximal on day 7 (data not shown), as previously demonstrated for Ty21a (Kantele et al., J. Infect. Dis. 153:1126, 1986). The excluded volunteer excluded with complicating non-typhoidal salmonellosis had 9 IgA secreting cells detected on day 0 and 1,325 on day 7 after vaccination.

Several serological studies were performed to examine humoral immune responses to different preparations of S. typhi antigens. ELISAs using standard 1:80 dilutions of serum samples to measure increases in serum IgG against O antigen or whole vaccine organisms were positive in 9/11 volunteers over the entire range of doses in each assay. ELISA results for a control group that received 4 doses of Ty21a were positive in 3/8 or 5/8 vaccinees, respectively in these assays. (Two control vaccinees, numbers 13 and 14, had high background OD values in these assays—one had been vaccinated with a parenteral typhoid fever vaccine more than 30 year ago). Peak IgG responses in these assays occurred on study days 14 or 21 days for both Ty800 and Ty21 vaccinees.

Five of 11 volunteers had evidence of seroconversion by four-fold or greater increases in endpoint titers utilizing S. typhi LPS as an antigen, and 6/11 seroconverted by four-fold or greater increases in the Widal tube agglutination test using H antigen. Considering seroconversion to either of these antigens evidence of a systemic immune response, 7/11 volunteers over the wide dose range given seroconverted after single dose vaccinations. In comparison, only 3/8 volunteers receiving 4 oral doses of Ty21a seroconverted by IgG endpoint titer vs. LPS (vs. Ty800, p=0.65), and none had positive Widal tube agglutination tests (vs. Ty800 , p=0.018).

Serum IgA directed against S. typhi LPS has been demonstrated to increase significantly in some individuals after vaccination with live attenuated S. typhi vaccines (Forrest et al., J. Infect. Dis. 163:336, 1991; Tackett et al., Vaccine 10:443, 1992). As IgA-ELISPOT studies were not performed for the Ty21a group, we measured serum IgA by ELISA to provide another measure of comparison between these 2 groups. Eight of 11 experimental vaccinees and 4/8 Ty21a vaccines had significant increases in OD values reflecting serum IgA directed against S. typhi LPS (Table 1A; p=0.38).

Three of 11 volunteers (numbers 6, 10, and 11) also had measurable increases in serum IgG directed against purified Vi antigen. In this assay, Ty21a vaccinees were used as a control population, as Ty21 does not express the Vi antigen. Volunteers 6, 8, and 10 had peak specific OD increases of 0.56, 0.26 and 0.34 OD units respectively at a 1:80 dilution of sera, while the mean net increase ±3 SD for Ty21a vaccinees from day 0 to day 21 was 0.02±0.04 OD units.

The studies described above demonstrates that Ty800, a genetically defined phoP/phoQ-deleted *S. typhi* Ty2, is markedly attenuated in human volunteers and is a very promising candidate vaccine and vector strain. Importantly, no volunteer developed serious side effects, or bacteremias even at very high doses. A dose level which induced some toxicity was reached, but only one volunteer had a self-limited gastroenteritis-like adverse event, and lower doses were clearly still immunogenic. One volunteer appeared to have become colonized with the vaccine organism; others shed the organism only transiently after vaccination. Unfortunately, quantitative stool cultures were not performed on the volunteer with prolonged shedding, and because this volunteer received antibiotics to eliminate the recombinant organism, the true duration of colonization could not be assessed. This volunteer received only $10^8$ cfu and volunteers receiving much larger doses did not have prolonged shedding, suggesting that colonization patterns may be more dependent upon host factors than vaccine-specific factors. It has been previously suggested that the presence or absence of secreted ABH carbohydrate determinants may modulate adherence of *S. typhi* to epithelial cells.

After vaccination with Ty21a, IgA production by PBMC in vitro is a very sensitive measure of immunological response which correlates more highly with intestinal IgA production than serum measurement of IgG or IgA (Forrest et al., *Infect. Immunol* 60:2023, 1992). Ten of 11 (91%) volunteers receiving any single dose of Ty800 had evidence of intestinal immune responses as measured by significant numbers *S. typhi* LPS-specific IgA-bearing peripheral blood mononuclear cells on day 7 after vaccination. In previous studies, 3 doses of Ty21a have resulted in detection of IgA-bearing cells by ELISPOT in 56% (Tacket et al., *J. Infect. Dis.* 163:901, 1991) to 80% (Kantele et al., *J. Infect. Dis.* 153:1126, 1986) of individuals. *S. typhi*-specific IgA production by PBMC in vitro was detected in 93%–100% of volunteers after vaccination with Ty21a (Forrest et al., *Lancet* 1:81, 1988; Forrest, *Infect. Immunol.* 60:2023, 1992). CVD908, a single dose, aromatic amino auxotrophic vaccine strain of *S. typhi*, induced *S. typhi*-specific antibody secreting cells (ASC) or in vitro IgA production by PBMC in 100% of volunteers (Gonzales et al., *J. Infect. Dis.* 169:927, 1994; Tacket et al, *Vaccine:*443, 1992) at doses that resulted in bacteremias in some individuals. In our study and those of other detection of ASC cells appears to be an extremely sensitive measure of immunological response to oral attenuated *S. typhi* vaccines. Ty800 induced more than 1000 ASC/$10^6$ PBMC in 6/11 volunteers and more than 2000 ASC/$10^6$ PBMC in those receiving the highest dose, larger numbers than previously reported in studies of attenuated live typhoid vaccines in which ASC numbers were specifically reported (Gonzales et al., supra; Kantele et al.,*J. Infect. Dis.* 153:1126, 1986). By the studies performed here, a single oral dose of Ty800 appeared to induce comparable, if not superior increases in markers of intestinal immune responses to multiple oral doses of Ty21a. These results suggest that Ty800 may be a particularly promising vector strain for antigens relevant to the gastrointestinal tract, or where secretory IgA at other sites is important. Direct measurement of intestinal IgA and IgA at other mucosal sites would be useful in future studies of Ty800.

The relative importance of intestinal and systemic serological responses in typhoid fever is debated (Levine et al., *Rev. Inf. Dis.* 11S3:S552, 1989). Systemic seroconversion has correlated with protection in endemic areas (Levine et al., supra), and parenteral vaccines which do not generate intestinal immunity have been shown to have some protective efficacy in both endemic areas (Levine et al., supra) and presumed naive vaccinees Schwartz et al., *Arch. Intern. Med.* 150:349, 1994). Additionally, generation of systemic humoral immune responses is relevant to other antigens potentially engineered into a multivalent vector strain (e.g. tetanus or pertussis toxin fragments). Systemic humoral immune responses measured by a variety of techniques after single doses of Ty800 were equal, and in some studies performed here, superior to those generated by 4 doses of Ty21a. 6/11 volunteers seroconverted by the Widal test, compared with 0/8 Ty21a vaccinees. Lack of seroconversion in the Widal test has been reported in previous study of Ty21a (Tacket et al., *J. Infect. Dis.* 163:901, 1991) and approximately 50% serconversion by Widal was seen in a recent study of volunteers receiving two oral doses of CVD908 expressing a malarial circumsporozoite antigen (Gonzales et al., supra).

We found that the most sensitive assays for detecting increases in serum IgG were ELISAs against whole vaccine organisms or *S. typhi* O antigen. We used this technique because it had successfully documented serological responses to attenuated *S. typhi* strains at the Center for Vaccine Development (Gonzales et al., supra; Tacket et al., Infect. Immun. 60:536, 1992; Tacket et al., Vaccine:443, 1992). Using these ELISAs, we found that even controls and volunteers with high baseline OD values in an endpoint dilution study (volunteers 6 and 8, and controls 13 and 14) mounted increases in specific OD units which exceeded by 3 standard deviations the mean net increase of the control cholera-vaccinated population. For example, volunteer 8, who had large increases in IgA-secreting cells but endpoint titers falling short of formally seroconverting had relatively large increases in optical densities ELISAs (0.6–0.8 OD units). This individual did not meet criteria for seroconversion by the less sensitive but presumably more specific endpoint dilution titer tests against *S. typhi* LPS (Table 1A); nevertheless it is likely that this volunteer had a true serological response to *S. typhi*. Similarly, controls 13 and 14 had high baseline titers in the LPS endpoint dilution study, and no increase after vaccination; these 2 control vaccinees did exceed the statistically significant threshold in the ELISA studies. We presume that these 4 individuals with high baseline titers or OD values may have unknowningly had prior typhoid fever vaccines or exposure to cross-reacting bacterial antigens. Most likely, nontyphoidal salmonellosis, which has been demonstrated to impair response to Ty21a (Forrest et al., *J. Infect. Dis.* 166:210, 1992) may be responsible for the high baseline values in serological tests and relatively poor serological responses in these individuals.

In both groups there were individuals with very low baseline serology results in all assays (volunteers 1 and 7 and controls 15 and 19) who were apparent serological nonresponders, presumably as a result of other unknown host factors. Volunteer 7 had no evidence of serological response in any assay, but still generated significant numbers of specific IgA-secreting cells, confirming that this is a very sensitive measure of immunological response to enteric vaccines. The results of the excluded volunteer with coexisting *S. brandenburg* infection are more difficult to interpret. Presumably the low level positive ELISPOT study on day 0 represent cells generated by the nontyphoidal infection which cross reacted with *S. typhi* LPS. It is not possible to say what proportion of day 7 ELISPOT cells are attributable to the experimental vaccine.

An unexpected finding in our study was the apparent systemic immune response to orally administered Vi antigen. There was no seroconversion to Vi antigen in a previous trial of 9 volunteers who received 3 oral doses of 5×10⁹ cfu of Ty21a engineered to express this antigen, despite expected rates of seroconversion to other antigens (Tacket et al., *J. Infect. Dis.* 163:901, 1991). Serological studies of Vi antigen responses have not been consistently reported in studies of other attenuated *S. typhi* vaccines, but occasional unquantified responses have been noted (Tacket et al., *Infect. Immun.* 60:536, 1992), suggesting that the more immunogenic live oral vaccines may also engender responses to Vi. Two of the volunteers (numbers 6 and 10) in our study who responded to this antigen were not those with the most vigorous serological responses in other assays, suggesting that host factors may direct responses to individual antigens. In summary, we have demonstrated that Ty800 is a promising new single-dose oral typhoid vaccine candidate which appears safe and is highly immunogenic. Although this study tested small numbers of volunteers at each dose, several important features of this vaccine strain are apparent. Large doses were well-tolerated and lower doses were immunogenic. There were no bacteremias in this study, making this vaccine strain more widely applicable to large populations than less attenuated strains. Very large numbers of vaccine specific IgA-secreting cells were generated, suggesting that this strain may be particularly useful in generating mucosal immune responses. phoP⁻ activated genes, which will be transcriptionally repressed in Ty800, have been demonstrated in vitro in *S. typhimurium* to inhibit antigen processing within murine macrophages (Wick et al., *Mol. Micro.* 16:465, 1995). We conclude that Ty800 may be a particularly useful vaccine strain for both development of a single oral dose typhoid fever vaccine and for engineering an *S. typhi* vector capable of delivering heterologous antigens to the gastrointestinal immune system.

Constitutive Expression of the phoP Regulon Attenuates Salmonella Virulence and Survival within Macrophages The phoP constitutive allele (phoP$^c$), pho-24, results in derepression of pag loci. Using diethyl sulfate mutagenesis of *S. typhimurium* LT-2, Ames and co-workers isolated strain TA2367 pho-24 (all strains, materials, and methods referred to in this section are described below), which contained a phoP locus mutation that resulted in constitutive production of acid phosphatase in rich media, Kier et al., 1979, J. Bacteriol. 138:155, hereby incorporated by reference. This phoP-regulated acid phosphatase is encoded by the phoN gene, a pag locus, Kier et al., 1979, supra, Miller et al., 1989, supra. To analyze whether the pho-24 allele increased the expression of other pag loci the effect of the pho-24 allele on the expression of other pag loci recently identified as transcriptional (e.g., pagA and pagB) and translational (e.g., pagC) fusion proteins that required phoP and phoQ for expression, Miller et al., 1989, supra, was determined. pag gene fusion strains, isogenic except for the pho-24 allele, were constructed and assayed for fusion protein activity. phoP$^c$ derivatives of the pagA::Mu dJ and pagB::Mu dJ strains produced 480 and 980 U, respectively, of β-galactosidase in rich medium, an increase of 9- to 10-fold over values for the fusion strains with a wild-type phoP locus, see Table 1.

TABLE 1

Bacterial strains and properties

| Strain | Genotype | Enzyme activity (U)[a] | Reference or source |
|---|---|---|---|
| 10428 | Wild type | 180 (A) | ATCC; Miller et al., 1989, supra |
| TA2367 | pho-24 | 1,925 (A) | Kier et al., 1974, supra |
| CS003 | ΔphoP ΔpurB | <10 (A) | Miller et al., 1989, supra |
| CS022 | pho-24 | 1,750 (A) | This work |
| CS023 | pho-24 phoN2 zxx::6251Tn10d-Cam | 25 (A) | This work |
| CS012 | pagA1::MU dJ | 45 (B) | Miller et al., 1989, supra |
| CS013 | pagB1::MU dJ | 120 (B) | Miller et al., 1989, supra |
| CS119 | pagC1::TnphoA phoN2 zxx::6251Tn10d-Cam | 85 (C) | Miller et al., 1989, supra |
| SC024 | pagA1::Mu dJ pho-24 | 450 (B) | This work |
| SC025 | pagB1::Mu dJ pho-24 | 980 (B) | This work |
| SC026 | pagC1::TnphoApho-24phoN2 zxx::6251Tn10d-Cam | 385 (B) | This work |
| CS015 | phoP102::Tn10d-Cam | <10 (A) | Miller et al., 1989, supra |
| TT13208 | phoP105::Tn10d | <10 (A) | —[b] |

[a]A. Acid phosphatase; B, β-galactosidase; C, alkaline phosphatase (AP).
[b]Gift of Ning Zhu and John Roth.

The pagC::TnphoA gene fusion produced 350 U of AP, an increase of three- to fourfold over that produced in strain CS119, which is isogenic except for the pho-24 mutation, Miller et al., 1989, supra. These results compare with a ninefold increase in the acid phosphatase activity in strain CS022 on introduction of the pho-24 allele. Therefore, these available assays for pag gene expression document that the pho-24 mutation causes constitutive expression of pag loci other than phoN.

Identifications of protein species that are repressed as well as activated in the phoP$^c$ mutant strain Whole-cell proteins of strain CS022 were analyzed to estimate the number of protein species that could be potentially regulated by the phoP regulon. Remarkably, analysis by one-dimensional polyacrylamide gel electrophoresis of the proteins produced by strains with the phoP$^c$ phenotype indicated that some protein species were decreased in expression when many presumptive pag gene products were fully induced by the pho-24 mutation. The proteins decreased in the PhoP$^c$ strain might represent products of genes that are repressed by the phoP regulator. Genes encoding proteins decreased by the pho-24 allele are designated prg loci, for phoP-repressed genes. Comparison of wild-type, PhoP⁻, and phoP$^c$ mutant strain proteins shows that growth in LB medium at 37° C. represents repressing conditions for pag gene products and derepressing conditions for prg gene products.

To estimate the total number of potentially PhoP⁻ regulated gene products, the total cell proteins of wild-type and phoP$^c$ mutant strains grown in LB were analyzed by two-dimensional gel electrophoresis. At least 40 species underwent major fluctuation in expression in response to the pho-24 mutation.

TABLE 2

Virulence and protective efficacy of PhoP$^c$ and PhoP$^-$ Salmonella strains

| Immunizing dose | No. of initial survivors/ total | No. of survivors/total after wild-type challenge dose of: | | | |
|---|---|---|---|---|---|
| | | $5 \times 10^7$ | $5 \times 10^5$ | $5 \times 10^4$ | $5 \times 10^3$ |
| PhoP$^c$ organisms | | | | | |
| 15 | 13/13 | | 5/5 | 4/5 | |
| 50 | 4/4 | | | | 4/4 |
| $1.5 \times 10^2$ | 11/11 | | 4/4 | 3/3 | |
| $5 \times 10^2$ | 16/16 | | | 4/4 | |
| $1.5 \times 10^3$ | 5/5 | | 3/3 | 2/2 | |
| $5 \times 10^3$ | 4/4 | | | | 4/4 |
| $1.5 \times 10^4$ | 5/5 | | 3/3 | 2/2 | |
| $5 \times 10^4$ | 19/23 | | | | 4/4 |
| $1.5 \times 10^5$ | 5/5 | | 3/3 | 2/2 | |
| $5 \times 10^5$ | 1/4 | | | | 1/1 |
| $5 \times 10^6$ | 0/6 | | | | |
| $3 \times 10^9$(*) | 5/5 | 5/5 | | | |
| $3 \times 10^{10}$(*) | 5/5 | 5/5 | | | |
| $1.5 \times 10^{11}$(*) | 5/5 | 5/5 | | | |
| PhoP$^-$ organisms | | | | | |
| $6 \times 10^3$ | 36/36 | | 0/12 | 0/12 | 0/12 |
| $6 \times 10^4$ | 36/36 | | 0/12 | 0/12 | 3/12 |
| $6 \times 10^5$ | 19/36 | | 0/6 | 0/6 | 4/7 |
| $5 \times 10^{10}$(*) | 7/7 | 3/7 | | | |

(*) Organisms were administered by the oral route. In all other experiments, organisms were administered by i.p. challenge.

Virulence defects of the PhoP$^c$ strain

Remarkably, strains with the single pho-24 mutation were markedly attenuated for virulence in mice (Table 2). The number of PhoP$^c$ organisms ($2 \times 10^5$) that killed 50% of BALB/c mice challenged (LD$_{50}$) by the intraperitoneal (i.p.) route was near that ($6 \times 10^5$) of PhoP$^-$ bacteria, Miller et al., 1989, supra. The PhoP$^c$ strains had growth comparable to wild-type organisms in rich and minimal media. The phoP$^c$ mutants were also tested for alterations in lipopolysaccharide, which could explain the virulence defect observed. Strain CS022 had normal sensitivity to phage P22, normal group B reactivity to antibody to O antigen, and a lipopolysaccharide profile identical to that of the parent strain, as determined by polyacrylamide gel electrophoresis and staining.

Since the TA2367 pho-24 strain was constructed by chemical mutagenesis and could have another linked mutation responsible for its virulence defect revertants of the phoP$^c$ were isolated to determine whether the pho-24 allele was responsible for the attenuation of virulence observed. Phenotype PhoP$^c$ revertants, identified by the normal levels of acid phosphatase in rich medium, were isolated among the bacteria recovered from the livers of mice infected with strain CS022. Six separate phenotypic revertants, designated CS122 to CS128, were found to be fully virulent (LD$_{50}$ of less than 20 organisms for BALB/c mice). The locus responsible for the reversion phenotype was mapped in all six revertants tested for virulence by bacteriophage P22 cotransduction and had linkage characteristics consistent with the phoP locus (greater than 90% linkage to purB). These data indicate that these reversion mutations are not extragenic suppressors but are intragenic suppressors or true revertants of the pho-24 mutation. Thus, the virulence defect of phoP$^c$ mutants is probably the result of a single revertible mutation in the phoP locus and not the result of a second unrelated mutation acquired during mutagenesis.

Reversion frequency of the PhoP$^c$ phenotype

The reversion frequency of the PhoP$^c$ mutation in vivo in mice was investigated to assess whether reversion could reduce the LD$_{50}$ of this strain. The presence of the revertants of strain CS022 was tested for by administering $10^6$, $10^4$, and $10^2$ challenge organisms to each of eight animals by i.p. injection. On day 7, three animals died that received $10^6$ phoP$^c$ organisms. On that day, the livers and spleens of all animals were harvested and homogenized in saline. After appropriate dilution, 10% of the tissue was plated on LB plates containing the chromogenic phosphatase substrate XP. Revertants were identified by their lighter blue colonies compared with PhoP$^c$ bacteria and were confirmed by quantitative acid phosphatase assays. An estimated $10^7$, $10^5$, and $10^3$ organisms per organ were recovered from animals at each of the three respective challenge doses. Revertants were identified only at the highest dose and comprised 0.5 to 1%, or $10^5$ organisms per organ, at the time of death. It is likely that revertants are able to compete more effectively for growth in these macrophage-containing organs, since strain CS022 is deficient in survival within macrophages (see below). However, revertants were not identified if fewer than $10^5$ organisms were administered in the challenge dose, suggesting that the reversion frequency must be approximately $10^{-5}$. The reversion rate of the phoP$^c$ phenotype for CS022 bacteria grown in LB is in fact $6 \times 10^{-4}$ when scored by the same colony phenotypes. The percentage of revertants recovered from animals near death suggests that pressure is applied in vivo that selects for revertants of the phoP$^c$ phenotype and implies that the virulence defect observed could be much greater quantitatively for a strain with a nonrevertible phoP$^c$ mutation.

The PhoP$^c$ strain is deficient in survival within macrophages

Because of the importance of survival within macrophages to Salmonella virulence Fields et al., 1986, Proc. Natl. Acad. Sci. USA 83:5189, hereby incorporated by reference, PhoP$^c$ bacteria were tested for this property. Strain CS022 was defective in the ability to grow and persist in macrophages as compared with wild-type organisms (FIG. 1). In FIG. 1 the survival of strain CS022 (PhoP$^c$) (triangles) in cultured macrophages is compared with that of wild-type S. typhimurium ATCC 10428 (circles). The experiment shown is a representative one. The difference between the two strains at 4 and 24 hours is significant (P<0.05). PhoP$^-$ bacteria seemed to have a macrophage survival defect qualitatively similar to that of PhoP$^c$ bacteria but survived consistently better by two- to threefold in side-by-side experiments. The increased recovery of organisms that reverted to PhoP$^-$ phenotype in mouse organs rich in macrophage content is consistent with the reduced macrophage survival of phoP$^c$ mutants in vitro.

Use of the PhoP$^c$ strain as a live vaccine

It has been previously reported that PhoP$^-$ strains are useful as live vaccines in protecting against mouse typhoid, Miller et al., 1989, supra. The immunogenicity of PhoP$^c$ when used as live attenuated vaccines in mice was compared with the of PhoP$^-$. This was done by simultaneous determination of survival, after graded challenge doses with the wild-type strain ATCC 10428, in mice previously immunized with graded doses of the two live vaccine strains. CS015 phoP::Tn10d-Cam and CS022 pho-24, as well as a saline control. The results obtained (Table 2) suggest the following conclusions: (i) small i.p. doses of the PhoP$^c$ strain (e.g., 15 organisms) effectively protect mice from challenge doses as large as $5 \times 10^5$ bacteria (a challenge dose that represents greater than $10^4$ i.p. LD$_{50}$s), (ii) large doses of PhoP$^c$ organisms given orally completely protect mice from an oral challenge consisting of $5 \times 10^7$ wild-type bacteria (over 200 oral wild-type LD$_{50}$s) and (iii) by comparison, a large dose of PhoP⁻ organisms (5×10⁵) does not provide similar protection. The reversion of the PhoP$^c$ mutation in vivo somewhat complicates the analysis of the use of these strains as vaccines, since revertants of the CS022 strain (i.e., wild-type cells) could increase immunogenicity). However, we were unable to identify revertants by examining 10% of the available spleen and liver tissue from those mice that received $10^4$ or fewer organisms.

Strains, Materials and Methods

The strains, materials, and methods used in the phoP regulon work described above are as follows.

American Type Culture Collection (ATCC) strain 14028, a smooth virulent strain of *S. typhimurium*, was the parent strain for all virulence studies. Strain TT13208 was a gift from Nang Zhu and John Roth. Strain TA2367 was a generous gift of Gigi Stortz and Bruce Ames, Kier et al., 1979, supra. Bacteriophage P22HT int was used in transductional crosses to construct strains isogenic except for phoP locus mutations, Davis et al., 1980, Advanced Bacterial Genetics, p. 78, 87. Cold Spring Harbor Laboratory, Cold Spring Harbor, N.Y., hereby incorporated by reference. Luria broth was used as rich medium, and minimal medium was M9, Davis et al., 1980, supra. The chromogenic phosphatase substrate 5-bromo-4-chloro-3indolyl phosphate (XP) was used to qualitatively access acid and AP production in solid media.

Derivatives of *S. typhimurium* ATCC 10428 with the pho-24 mutation were constructed by use of strain TA2367 as a donor of the purB gene in a P22 transductional cross with strain CS003 ΔphoP ΔpurB, Miller et al., 1989, supra. Colonies were then selected for the ability to grow on minimal medium. A transductant designated CS022 (phenotype PhoP$^c$) that synthesized 1,750 U of acid phosphatase in rich medium (a ninefold increase over the wild-type level in rich medium) was used in further studies.

Derivatives of strains CS022 and CS023 pho-24 phoN2 zxx::6251Tn10d-Cam, and acid phosphatase-negative derivative of CS022, containing pag gene fusions were constructed by bacteriophage P22 transductional crosses, using selection of TnphoA- or Mu dJ-encoded kanamycin resistance. Strains were checked for the intact pag gene fusion by demonstration of appropriate loss of fusion protein activity on introduction of a phoP105::Tn10d or phoP102::Tn10d-Cam allele.

Assays of acid phosphatase, AP, and β-galactosidase were performed as previously described, Miller et al., 1989, supra and are reported in units as defined in Miller, 1972, Experiments in molecular genetics, p. 352–355, Cold Spring Harbor Laboratory, Cold Spring Harbor, N.Y., hereby incorporated by reference.

In the mouse virulence and vaccination studies bacteria grown overnight in Luria broth were washed and diluted in normal saline. The wild-type parent strain of CS022 (ATCC 10428) was used for all live vaccine challenge studies. This strain has a 50% lethal dose (LD$_{50}$) for naive adult BALB/c mice of less than 20 organisms when administered by intraperitoneal (i.p.) injection and 5×10⁴ when administered orally in NaHCO₃. Mice were purchased from Charles River Breeding Laboratories, Inc. (Wilmington, Mass.) and were 5 to 6 weeks of age at initial challenge. All i.p. inoculations were performed as previously described, Miller et al., 1989, supra. Oral challenge experiments were performed with bacteria grown in LB broth and concentrated by centrifugation. The bacteria were resuspended in 0.1M NaHCO₃ to neutralize stomach acid, and administered as a 0.5-ml bolus to animals under ether anesthesia. Colony counts were performed to accurately access the number of organisms administered. All challenge experiments were performed 1 month after i.p. inoculation and 6 weeks after oral challenge. Challenge inocula were administered by the same route as vaccinations. The care of all animals was under institutional guidelines as set by the animal are committees at the Massachusetts General Hospital and Harvard Medical School.

Protein electrophoresis was performed as follows. One-dimensional protein gel electrophoresis was performed by the method of Laemmli, 1970, Nature 227:680, hereby incorporated by reference, on whole-cell protein extracts of stationary-phase cells grown overnight in Luria broth. The gels were fixed and stained with Coomassie brilliant blue R250 in 10% acetic acid-10% methanol. Two-dimensional protein gel electrophoresis was performed by method of O'Farrell, 1975, J. Biol. Chem. 250:4007, hereby incorporated by reference, on the same whole-cell extracts. Isoelectric focusing using 1.5% pH 3.5 to 10 ampholines (LKB Instruments, Baltimore, Md.) was carried out for 9,600 V h (700 V for 13 h 45 min). The final tube gel pH gradient extended from pH 4.1 to pH 8.1 as measured by a surface pH electrode (BioRad Laboratories, Richmond, Calif.) and colored acetylated cytochrome pI markers (Calbiochem-Behring, La Jolla, Calif.) run in an adjacent tube. The slab gels were silver stained, Merril et al., 1984, Methods Enzymol. 104:441, hereby incorporated by reference.

In the macrophage survival assays experiments were performed as previously described, Miller et al., 1989, supra, by the method of Buchmeier et al., 1989, Infect. Immun. 57:1, hereby incorporated by reference, as modified from the method of Lissner et al, 1983, J. Immunol. 131:3006, hereby incorporated by reference. Stationary-phase cells were opsonized for 30 min in normal mouse serum before exposure to the cultured bone marrow-derived macrophages harvested from BALB/c mice. One hour after infection, gentamicin sulfate (8 µg/ml) was added to kill extracellular bacteria. All time points were done in triplicate and repeated on three separate occasions.

phoP$^c$ Mutant Strains Are More Effective as Live Vaccines phoP$^c$ mutant *S. typhimurium* are very effective when used as a live vaccine against mouse typhoid fever and are superior to PhoP⁻ bacteria. As few a 15 phoP$^c$ bacteria protect mice against $10^5$ LD$_{50}$ (lethal doses 50%) of wild type organisms by the intraperitoneal route (Table 3). This suggests that pag gene products are important antigens for protective immunity against mouse typhoid. Preliminary results have documented that antigens recognized by serum of chronic typhoid carriers recognizes some phoP-regulated gene products of *S. typhi*. If protective antigens are only expressed within the host, then dead vaccines only grown in rich media may not induce an immune response against these proteins.

The use of different *S. typhimurium* dead vaccine preparations containing different mutations in the phoP regulon was evaluated. As can be seen in Table 3 no dead cell preparations (even those containing mixtures of PhoP⁻ and phoP$^c$ bacteria) are as effective vaccines as are live bacteria. This suggests that there are other properties of live vaccines that increase immunogenicity or that important non-PhoP-regulated antigens are not in these preparations. The only protection observed in any animals studied was at the lowest challenge dose for those immunized with PhoP$^c$ bacteria. This further suggests that phoP activated genes are important protective antigens.

TABLE 3

Salmonella with phoP regulon mutations used as a dead vaccine

| Vaccination | | Challenge dose of wild type organisms | |
|---|---|---|---|
| Strain | phenotype | $6 \times 10^3$ | $6 \times 10^5$ |
| None | | (3) | (5) |
| ATCC10428 | wild type | (8) | (9) |
| CS015 | PhoP⁻ | (10) | (13) |
| CS022 | PhoPᶜ | 2/7(*) | (14) |
| CS022/CS015 | PhoP⁻/PhoPᶜ | (8) | (13) |

CS015 = phoP102::Tn10d-Cam
CS022 = pho-24
BALB/c mice were immunized twice, 7 days apart, with $5 \times 10^8$ formalin-killed bacteria. Three weeks after the second vaccination, mice were challenged with wild-type organisms at the two doses indicated. The numbers in parentheses indicate no survivors after challenge and mean number of days until death (*) Ratio of survivors to number challenged.
phoPᶜ indicates the constitutive unregulated expression of phoP-activated genes and lack of expression of phoP repressed genes.
phoP indicates a lack of expression of phoP-activated genes and expression of phoP repressed genes.

aroA phoP Regulon Double Mutant Strains

Recent efforts by Stocker, Levine, and colleagues have focused on the use of strains with auxotrophic mutations in aromatic amino acid and purine pathways as live vaccines, Hoseith et al., 1981, Nature 291:238, hereby incorporated by reference, Stocker, 1988, Vaccine 6:141, hereby incorporated by reference, and Levine et al., 1987, J. Clin. Invest. 79:888, hereby incorporated by reference. Purine mutations were found to be too attenuating for immunogenicity, likely because purines are not available to the organism within the mammalian host, Sigwart et al., 1989, Infect. Immun. 57:1858, hereby incorporated by reference. Because auxotrophic mutations may be complemented by homologous recombination events with wild type copies donated from environmental organisms or by acquiring the needed metabolite within the host, it would seem prudent for live vaccines to contain a second attenuating mutation in a different virulence mechanism, (i.e., not just a second mutation in the same metabolic pathway). Additionally, in mice the aroA mutants have some residual virulence. Various strains with aroA mutations combined with phoP regulon mutations were investigated for virulence attenuation and immunogenicity. Table 4 demonstrates that a phoP⁻ or phoPᶜ mutation further attenuates aroA mutant *S. typhimurium* by at least 100-fold and that, at least at high levels of vaccinating organisms, immunogenicity is retained. Strains with both a PagC⁻ and PhoPᶜ phenotype are also further attenuated than either mutation alone. Therefore, phoP regulon mutations may increase the safety of aroA live vaccine preparations.

TABLE 4A

Additional attenuation of aroA mutants by phop regulon mutations

| | | Survivors of varying numbers of Salmonella mutant organisms (*) | | | | |
|---|---|---|---|---|---|---|
| Strain | Phenotype | $10^6$ | $10^7$ | $10^8$ | $10^9$ | $10^{10}$(**) |
| CS004 | AroA⁻ | 6/6 | 1/6 | 0/6 | 0/6 | 6/6 |
| SL3261 | AroAdel His⁻ | 6/6 | 1/6 | 0/6 | 0/6 | 6/6 |
| CS322 | AroA⁻ PhoPᶜ | 6/6 | 6/6 | 6/6 | 1/6 | 6/6 |
| CS323 | SL3261 PhoPᶜ | 6/6 | 6/6 | 6/6 | 2/6 | 6/6 |
| CS315 | aroA⁻ PhoP⁻ | 6/6 | 6/6 | 6/6 | 2/6 | 6/6 |
| CS316 | SL3261 PhoP⁻ | 6/6 | 6/6 | 6/6 | 1/6 | 6/6 |
| CS026 | PagC⁻ PhoPᶜ | 6/6 | 4/6 | 0/6 | 0/6 | 6/6 |

Table 4B

Protective efficacy of Salmonella with aroA/phoP regulon mutations
Survivors of challenge doses of wild type organisms (*)

| Strain | Phenotype | Inoculum | $5 \times 10^5$ | $5 \times 10^7$ |
|---|---|---|---|---|
| CS004 | AroA⁻ | $10^6$ | 4/4 | 5/5 |
| SL3261 | AroAdel His⁻ | $10^6$ | 4/4 | 4/5 |
| CS322 | AroA⁻ PhoPᶜ | $10^6$ | 5/5 | |
| CS323 | SL3261 PhoPᶜ | $10^6$ | 5/5 | |
| CS322 | AroA⁻ PhoPᶜ | $10^7$ | 5/5 | |
| CS323 | SL3261 PhoPᶜ | $10^7$ | 5/5 | |
| CS322 | AroA⁻ PhoPᶜ | $10^8$ | | 5/5 |
| CS323 | SL3261 PhoPᶜ | $10^8$ | | 5/5 |
| CS315 | AroA⁻ PhoP⁻ | | 5/5 | |
| CS316 | 5L3261 PhoP⁻ | $10^8$ | 5/5 | |

(*) Ratio of survivors to number of mice challenged.
(**) Indicates oral inoculation all other experiments were intraperitoneal inoculation.
CS004 = aroA554::rn10.
SL3261 = aroADEL407 hisG46.
CS322 = aroA554::Tn10 pho-24.
CS323 = aroADEL407 pho-24.
CS315 = aroA554::Tn10 phoP102::Tn10d-Cam.
CS316 = aroADEL407 hisG46 phoP102::Tn10d-Cam.
CS026 = pagC1::TnphoA pho-24 phoN2 zxx::6251TN10d-Cam.

*Salmonella typhi* phoP Regulon Mutations

The phoP regulon is at least partially conserved in *S. typhi* DNA hybridization studies as well as P22 bacteriophage transductional crosses have documented that the phoP, phoQ, and pagC genes appear highly conserved between *S. typhi* and *S. typhimurium* mutations in these genes in *S. typhi* have been made.

Salmonella Live Vaccines as Delivery Systems for Heterologous Antigens

The vector used in the vaccine delivery system is a derivative of pJM703.1 described in Miller et al., 1988, J. Bact. 170:2575, hereby incorporated by reference. This vector is an R6K derivative with a deletion in the pir gene. R6K derivatives require the protein product of the pir gene to replicate. *E. coli* that contain the pir gene present as a lambda bacteriophage prophage can support the replication of this vector. Cells that do not contain the pir gene will not support the replication of the vector as a plasmid. This vector also contains the mob region of RP4 which will allow mobilization into other gram negative bacteria by mating from *E. coli* strains such as SM10lambda pir, which can provide the mobilization function in trans.

Figure 2:
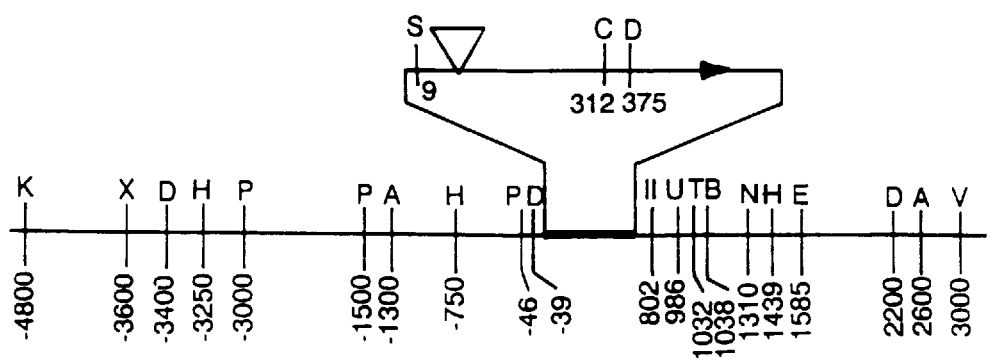

The pagC region is shown in FIGS. 2 and 3. FIG. 2 shows the restriction endonuclease sites of the pagC locus. The heavy bar indicates pagC coding sequence. The TnphoA insertion is indicated by a inverted triangle. The direction of transcription is indicated by the arrow and is left to right. The numbers indicate the location of endonuclease sites, in number of base pairs, relative to the start codon of predicted pagC translation with positive numbers indicating location downstream of the start codon and negative numbers indicating location upstream of the start codon. A is AccI, B is BglI, C is ClaI, D is DraI, E is EcoRI, H is HpaI, N is NruI, P is PstI, S is SspI, T is StuI, U is PvuII, V is EcoRV, and II is BglII. FIG. 3 shows the DNA sequence (Sequence I.D. No. 1) and translation of pagC::TnphoA. The heavy underlined sequence indicates a potential ribosomal binding site. The single and double light underlines indicate sequences in which primers were constructed complementary to these nucleotides for primer extension of RNA analysis. The asterisk indicates the approximate start of transcription. The arrow indicates the direction of transcription. The boxed sequences indicate a region that may function in polymerase binding and recognition. The inverted triangle is the site of the sequenced TnphoA insertion junction. The arrow indicates a potential site for single sequence cleavage.

3 kilobases of DNA containing the pagC gene (from the PstI restriction endonuclease site 1500 nucleotides 5' to the start of pagC translation to the EcoRI restriction endonuclease site 1585 nucleotides downstream of pagC translation termination) were inserted into the pJM703.1 derivative discussed above. The pagC sequence from the ClaI restriction endonuclease site was deleted (490 nucleotides) and replaced with a synthetic oligonucleotide polylinker that creates unique restriction endonuclease sites. DNA encoding one or more heterologous proteins, e.g., an antigen, can be inserted into this site. This creates a vector which allows the insertion of multiple foreign genes into the DNA surrounding pagC.

The vector can be mobilized into Salmonella by mating or any other delivery system, e.g., heat shock, bacteriophage transduction or electroporation. Since it can not replicate, the vector can only insert into Salmonella by site specific recombination with the homologous DNA on both sides of the pagC gene. This will disrupt and inactivate the native pagC locus and replace it with the disrupted pagC DNA carried on the vector.

Such recombination events can be identified by marker exchange and selective media if the foreign DNA inserted into the pagC locus confers a growth advantage. The insertion of antibiotic resistance genes for selection is less desirable as this could allow an increase in antibiotic resistance in the natural population of bacteria. Genes which confer resistance to substances other than antibiotics e.g., to heavy metals or arsenic (for mercury resistance, see Nucifora et al., 1989, J. Bact., 171:4241–4247, hereby incorporated by reference), can be used to identify transformants. Alternatively, selection can be performed using a Salmonella recipient strain that carries an auxotrophic mutation in a metabolic pathway and a vector that carries DNA that complements the auxotrophic mutation. Many Salmonella live vaccine prototypes contain mutations in histidine or purine pathways thus complementation of these metabolic auxotrophies can be used to select for integrants. (Purine mutations specifically have been shown to be too attenuated for use in man.) Further proof of marker exchange can be documented by loss of the ampicillin resistance (carried on the plasmid backbone) or by blot hybridization analysis.

A gene useful for selection can be cloned by complementation of a vaccine strain with a metabolic auxotrophy. Specific examples include the cloning of the DNA encoding both purB and phoP by complementation of a strain deleted for function of both these genes. Salmonella gene libraries have been constructed in a pLAFR cosmid vector (Frindberg et al., 1984, Anal. Biochem. 137:266–267, hereby incorporated by reference) by methods known to those skilled in the art. pLAFR cosmids are broad host range plasmids which can be mobilized into Salmonella from $E.$ $coli$. An entire bank of such strains can be mobilized into Salmonella vaccine strains and selected for complementation of an auxotrophic defect (e.g., in the case of purB growth on media without adenine). The DNA able to complement this defect is then identified and can be cloned into the antigen delivery vector.

As discussed above heterologous genes can be inserted into the polylinker that is inserted into the pagC sequence of the vector. The heterologous genes can be under the control of any of numerous environmentally regulated promotor systems which can be expressed in the host and shut off in the laboratory. Because the expression of foreign proteins, especially membrane proteins (as are most important antigens), is frequently toxic to the bacterium, the use of environmentally regulated promoters that would be expressed in mammalian tissues at high levels but which could be grown in the laboratory without expression of heterologous antigens would be very desirable. Additionally, high expression of antigens in host tissues may result in increased attenuation of the organism by diverting the metabolic fuel of the organism to the synthesis of heterologous proteins. If foreign antigens are specifically expressed in host phagocytic cells this may increase the immune response to these proteins as these are the cells responsible for processing antigens.

The promoter systems likely to be useful include those nutritionally regulated promoter systems for which it has been demonstrated that a specific nutrient is not available to bacteria in mammalian hosts. Purines, Sigwart et al., 1989, Infect. Immun., 57:1858 and iron, Finklestein et al., 1983, Rev. Infect. Dis. 5:S759, e.g., are not available within the host. Promoters that are iron regulated, such as the aerobactin gene promoter, as well as promoters for biosynthetic genes in purine pathways, are thus excellent candidates for testing as promoters that can be shut down by growth in high concentrations of these nutrients. Other useful environmentally regulated Salmonella promoters include promoters for genes which encode proteins which are specifically expressed within macrophages, e.g., the DnaK and GroEL proteins, which are increased by growth at high temperature, as well as some phoP activated gene products, Buchmeier et al., 1990, Science 248:730, hereby incorporated by reference. Therefore, promoters such as the pagC 5' controlling sequences and the better characterized promoters for heat shock genes, e.g., GroEL and DnaK, will be expected to be activated specifically within the macrophage. The macrophage is the site of antigen processing and the expression of heat shock genes in macrophages and the wide conservation of heat shock genes in nature may explain the immunodominance of these proteins. A consensus heat shock promoter sequence is known and can be used in the vectors (Cowling et al., 1985, Proc. Natl. Acad. Sci. USA 82:2679, hereby incorporated by reference).

The vectors can include an environmentally regulated T7 polymerase amplification system to express heterologous proteins. For example, the T7 polymerase gene (cloned by Stan Tabor and Charles Richardson, See Current Protocols in Molecular Biology ed. Ausubel et al., 1989, (page 3.5.1.2) John Wiley and Sons, hereby incorporated by reference) under control of an iron regulated promoter, can be included on the vectors described above. We have inserted the aerobactin gene promoter of $E.$ $coli$ with the sequence C A T T T C T C A T T G ATA A T G A G A A T C AT-TATTGACATAATTGTTATTATTTTACG (SEQ ID NO:2), Delorenzo et al. J. Bact. 169:2624, hereby incorporated by reference, in front of the T7 polymerase gene and demonstrated iron regulation of the gene product. This version of the vector will also include one or more heterologous antigens under the control of T7 polymerase promoters. It is well known that RNA can be synthesized from synthetic oligonucleotide T7 promoters and purified T7 in vitro. When the organism encounters low iron T7 polymerase will be synthesized and high expression of genes with T7 promoters will be facilitated.

PaqC-fusion proteins in *S. typhimurium*

Expression of heterologous antigens within macrophages under the control of phoP regulated promoters can be used as an effective method of both attenuating Salmonellae and enhancing immunogenicity of foreign antigens. As discussed above, the expression of pagC is induced in antigen processing cell, i.e., a macrophage.

Thus, expression of a heterologous antigen under the control of the pagC promoter is also likely to be inducible in macrophages.

To evaluate the immune response to a heterologous antigen expressed under the control of inducible pag promoters, mice were inoculated with bacteria which expressed the antigen, AP, under the control of the pagC or pagD regulatory sequences. Pag-AP fusion proteins were produced in these bacteria from a single chromosomal copy of the gene encoding AP. The bacteria were generated utilizing two methods: TnphoA mutagenesis, and genetic engineering techniques using a suicide vector, both of which are described above.

As a control, mice were innoculated with bacteria which expressed an AP fusion protein under the control of constitutive promoters. The constitutive promoter was completely independent of regulation by genes in the phoP regulon. Two such strains of bacteria, Strain 610 and Strain 617, were constructed using methods described above. AP expression in Strain 610 was moderate, whereas AP expression in Strain 617 was high (see FIG. 14C).

These strains were injected intraperitoneally into BABL/C mice. Serum samples were taken three weeks after inoculation. Normal mouse serum (MNS) was used as a control. Standard ELISA assays were used to test the sera for the presence of AP-specific antibodies. Sera was also tested for LPS-specific antibodies using *S. typhimurium* LPS. Antibodies directed to LPS were detected in all the murine sera tested, but only those strains in which AP was expressed as a Pag fusion protein from a single chromosomal gene copy engendered an immune response against the model heterologous antigen, AP (see FIGS. 14A and FIG. 14B).

Despite approximately 10-fold higher constitutive expression of the AP fusion in strain 617, only a minimal immune response to this antigen was noted after immunization with strain 617. In contrast, a strong response was observed in mice inoculated with strains which expressed the Pag-AP fusion protein. These data indicate that phoP- regulation which results in in vivo induction of protein expression within macrophages increases the immunogenicity of heterologous antigens expressed under the control of the pag promoters. Any promoter which directs cell-specific, inducible expression of a protein in macrophages or other antigen presenting cells, e.g., pag described herein, can be used to increase the immunogencity of an antigen expressed in Salmonella.

The pagC gene and pagC Gene Product Strains, materials, and methods

The following strains, materials, and methods were used in the cloning of pagC and in the analysis of the gene and its gene product.

Rich media was Luria broth (LB) and minimal media was M9, Davis et al., 1980, supra. The construction of *S. typhimurium* strain CS119 pagC1::TnphoA phoN2 zxx::6251 Tn10d-Cam was previously described, Miller et al., 1989, supra. American Type Culture Collection (ATCC) *S. typhimurium* strain 10428 included CS018 which is isogenic to CS119 except for phoP105::Tn10d, Miller et al., 1989, supra, CS022 pho-24, Miller et al., 1990, J. Bacteriol. 172:2485– 2490, hereby incorporated by reference, and CS015 phoP102::Tn10d-cam, Miller et al., 1989, supra. Other wild type strains used for preparation of chromosomal DNA included *S. typhimurium* LT2 (ATCC 15277), *S. typhimurium* Q1 and *S. drypool* (Dr. J. Peterson U. Texas Medical Branch, Galveston), and *Salmonella typhi* Ty2 (Dr. Caroline Hardegree, Food and Drug Administration). pLAFR cosmids were mobilized from *E. coli* to *S. typhimurium* using the *E. coli* strain MM294 containing pRK2013, Friedman et al., 1982, Gene 18:289–296, hereby incorporated by reference. AP activity was screened on solid media using the chromogenic phosphatase substrate 5-bromo-4-chloro-3-indolyl phosphate (XP). AP assays were performed as previously described, Brickman et al., 1975, J. Mol. Biol. 96:307–316, hereby incorporated by reference, and are reported in units as defined by Miller, 1972, supra, pp. 352–355.

One dimensional protein gel electrophoresis was performed by the method of Laemmli, 1970, Nature, 227:680–685, hereby incorporated by reference, and blot hybridization using antibody to AP was performed as previously described, Peterson et al., 1988, Infect. Immun. 56:2822–2829, hereby incorporated by reference. Whole cell protein extracts were prepared, from saturated cultures grown in LB at 37° C. with aeration, by boiling the cells in SDS-pagE sample buffer, Laemmli, 1970, supra. Two dimensional gel electrophoresis was performed by the method of O'Farrell, 1975, J. Biol. Chem. 250:4007, hereby incorporated by reference. Proteins in the 10% polyacrylamide slab gels were visualized by silver staining, Merril et al., 1984, Methods in Enzymology, 104:441, hereby incorporated by reference.

Chromosomal DNA was prepared by the method of Mekalanos, 1983, Cell, 35:253–263, hereby incorporated by reference. DNA, size fractionated in agarose gels, was transferred to nitrocellulose (for blot hybridization) by the method of Southern, 1975, J. Mol. Biol. 98:503–517, hereby incorporated by reference. DNA probes for Southern hybridization analysis were radiolabeled by the random primer method, Frinberg et al., 1984, supra. Plasmid DNA was transformed into *E. coli* and Salmonella by calcium chloride and heart shock, Mekalanos, 1983, supra, or by electroporation using a Genepulser apparatus (BioRad, Richmond, Calif.) as recommended by the manufacturer, Dower et al., 1988, Nucl. Acids Res. 16:6127–6145, hereby incorporated by reference. DNA sequencing was performed by the dideoxy chain termination method of Sanger et al., 1977, Proc. Natl. Acad. Sci. USA, 74:5463–5467, hereby incorporated by reference, as modified for use with SEQUENASE® (U.S. Biochemical, Cleveland, Ohio). Oligonucleotides were synthesized on an Applied Biosystems Machine and used as primers for sequencing reactions and primer extension of RNA. Specific primers unique to the two ends of TnphoA, one of which corresponds to the AP coding sequence and the other to the right IS50 sequence, were used to sequence the junctions of the transposon insertion.

Construction of a *S. typhimurium* cosmid gene bank in pLAFR3 and screening for clones containing the wild type pagC DNA was performed as follows. DNA from *S. typhimurium* strain ATCC 10428 was partially digested using the restriction endonuclease Sau3A and then size selected on 10–40% sucrose density gradient. T4 DNA ligase was used to ligate chromosomal DNA of size 20–30 kilobases into the cosmid vector pLAFR3, a derivative of pLAFR1, Friedman et al., 1982, Gene 18:289–296, hereby incorporated by reference, that was digested with the restriction endonuclease BamHI. Cosmid DNA was packaged and transfected into *E. coli* strain DH5-α using extracts purchased from Stratagene, La Jolla, Calif. Colonies were screened by blot hybridization analysis.

The analysis of proteins produced from cloned DNA by in vitro transcription/translation assays was analyzed as follows. These assays were performed with cell free extracts, (Amersham, Arlington Heights, Ill.), and were performed using conditions as described by the manufacturer. The resultant radiolabeled proteins were analyzed by SDS-pagE.

RNA was purified from early log and stationary phase Salmonella cultures by the hot phenol method, Case et al., 1988, Gene 72:219–236, hereby incorporated by reference, and run in agarose-formaldehyde gels for blot hybridization analysis, Thomas, 1980, Proc. Natl. Acad. Sci. USA 77:5201, hereby incorporated by reference. Primer extension analysis of RNA was performed as previously described, Miller et al., 1986, Nuc. Acids. Res. 14:7341–7360, hereby incorporated by reference, using AMV reverse transcriptase (Promega, Madison, Wis.) and synthesized oligonucleotide primers complementary to nucleotides 335–350 and 550–565 of the pagC locus.

Identification of an 18 kDa protein missing in a pagC mutant of *S. typhimurium* pagC mutant strain CS119 was analyzed by two dimensional protein electrophoresis to detect protein species that might be absent as a result of the TnphoA insertion. Only a single missing protein species, of approximately 18 kD and pI–8.0, was observed when strains, isogenic except for their transposon insertions, were subjected to this analysis. This 18 kDa species was also missing in similar analysis of Salmonella strains with mutations phoP and phoQ. Though two-dimensional protein gel analysis might not detect subtle changes of protein expression in strain CS119, this suggested that a single major protein species was absent as a result of the pagC::TnphoA insertion.

Additional examination of the 2-dimensional gel analysis revealed a new protein species of about 45 kDa that is likely the PagC-Ap fusion protein. The PagC-AP fusion protein was also analyzed by Western blot analysis using antisera to AP and found to be similar in size to native AP (45 kDa) and not expressed in PhoP-*S. typhimurium*.

Cloning of the pagC::TnphoA insertion

Chromosomal DNA was prepared from *S. typhimurium* strain CS119 and a rough physical map of the restriction endonuclease sites in the region of the pagC::TnphoA fusion was determined by using a DNA fragment of TnphoA as a probe in blot hybridization analysis. This work indicated that digestion with the restriction endonuclease ecoRV yielded a single DNA fragment that included the pagC::TnphoA insertion in addition to several kilobases of flanking DNA. Chromosomal DNA from strain CS119 was digested with EcoRV (blunt end) and ligated into the bacterial plasmid vector pUC19 (New England Biolabs) that had been digested with the restriction endonuclease SmaI (blunt end). This DNA was electroporated into the *E. coli* strain DH5-α (BRL) and colonies were plated onto LB agar containing the antibiotics kanamycin (TnphoA encoded and ampicillin (pUC19 encoded). A single ampicillin and kanamycin resistant clone containing a plasmid designated pSM100 was selected for further study.

A radiolabeled DNA probe from pSM100 was constructed and used in Southern hybridization analysis of strain CS119 and its wild type parent ATCC 10428 to prove that the pagC::TnphoA fusion had been cloned. The probe contained sequences immediately adjacent to the transposon at the opposite end of the AP gene [HpaI endonuclease generated DNA fragment that included 186 bases of the right IS50 of the transposon and 1278 bases of Salmonella DNA (FIG. 2). As expected, the pSM100 derived probe hybridized to an 11–12 kb AccI endonuclease digested DNA fragment from the strain containing the transposon insertion, CS119. This was approximately 7.7 kb (size of TnphoA) larger than the 3.9 kB AccI fragment present in the wild type strain that hybridizes to the probe. In addition, a derivative of plasmid pSM100, pSM101 (which did not allow expression of the pagC-phoA gene fusion off the lac promoter), was transformed into phoP- (strain Cs015) and phoN- (strain CS019) Salmonella strains and the cloned AP activity was found to be dependent on phoP for expression. Therefore we concluded that the cloned DNA contained the pagC::TnphoA fusion.

The presence of the pagC gene was also demonstrated in other strains of *S. typhimurium*, as well as in *S. typhi*, and *S. drypool*. All Salmonella strains examined demonstrated similar strong hybridization to an 8.0 kb EcoRV and a 3.9 kb AccI restriction endonuclease fragment suggesting that pagC is a virulence gene common to Salmonella species.

The pagC gene probe from nucleotides –46 (with 1 as the first base of the methionine to 802 (PstI site to the BglII site) failed to cross hybridize to DNA from *Citrobacter freundii*, *Shigella flexneri*, *Shigella sonnei*, *Shigella dysenterial*, *Escherichia coli*, *Vibrio cholerae*, *Vibrio vulnificus*, *Yersenia entero colitica*, and *Klebsiella pneumonia*.

Cloning of the wild type pagC locus DNA and its complementation of the virulence defect of a *S. typhimurium* pagC mutant The same restriction endonuclease fragment described above was used to screen a cosmid gene bank of wild type strain ATCC 10428. A single clone, designated pWP061, contained 18 kilobases of *S. typhimurium* DNA and hybridized strongly to the pagC DNA probe. pWP061 was found to contain Salmonella DNA identical to that of pSM100 when analyzed by restriction endonuclease analysis and DNA blot hybridization studies. Probes derived from pWP061 were also used in blot hybridization analysis with DNA from wild type and CS119 *S. typhimurium*. Identical hybridization patterns were observed to those seen with pSM100. pWP061 was also mobilized into strain CS119, a pagC mutant strain. The resulting strain had wild type virulence for BALB/c mice (a $LD_{50}$ less than 20 organisms when administered by IP injection). Therefore the cloned DNA complements the virulence defect of a pagC mutant strain.

Since, a wild type cosmid containing pagC locus DNA was found to complement the virulence defect of a pagC mutant *S. typhimurium* strain, it was concluded that the pagC protein is an 188 amino acid (18 kDa) membrane (see below) protein essential for survival within macrophages and virulence of *S. typhimurium*.

Physical mapping of restriction endonuclease sites, DNA sequencing, and determination of the pagC gene product Restriction endonuclease analysis of plasmid pSM100 and pWP061 was performed to obtain a physical map of the pagC locus, and, in the case of PSM100, to determine the direction of transcription (FIG. 2). DNA subclones were generated and the TnphoA fusion junctions were sequenced, as well as the Salmonella DNA extending from the HpaI site, 828 nucleotides 5' to the phoA fusion junction, to the EcoRI site 1032 nucleotides 3' to the TnphoA insertion (FIG. 2 and 3). The correct reading frame of the DNA sequence was deduced from that required to synthesize an active AP gene fusion. The deduced amino acid sequence of this open reading frame was predicted to encode a 188 amino acid protein with a predicted pI+8.2. This data were consistent with the 2-D polyacrylamide gel analysis of strain CS119 in which an 18 kDa protein of approximate pI+8.0 was absent. No other open reading frames, predicted to encode peptides larger than 30 amino acids, were found.

The deduced amino acid sequence of the 188 amino acid open reading frame contains a methionine start codon 33 amino acids from the fusion of pagC and AP (FIG. 3). This 33 amino acid pagC contribution to the fusion protein was consistent with the size observed in Western blot analysis and contains a hydrophobic N-terminal region, identified by the method of Kyle et al., 1982, J. Mol. Biol. 157:105–132, hereby incorporated by reference, that is a typical bacterial signal sequence, Von Heinje, 1985, J. Mol. Biol. 184:99–105, hereby incorporated by reference. Specifically, amino acid 2 is a positively charged lysine, followed by a hydrophobic domain and amino acid 24 is a negatively charged aspartate residue. A consensus cleavage site for this leader peptide is predicted to be at an alanine residue at amino acid 23, Von Heinje, 1984, J. Mol. Biol. 173:243–251, hereby incorporated by reference. The DNA sequence also revealed a typical ribosomal binding site, Shine et al., 1974, Proc. Natl. Acad. Sci. USA 71:1342–1346, hereby incorporated by reference, at 6–2 nucleotides 5' to the predicted start of translation (FIG. 3) nucleotides 717–723). This suggested that the open reading frame was, in fact, translated and further supported the assumption that this was the deduced amino acid sequence of the PagC protein interrupted by the TnphoA insertion (FIG. 3).

In vitro synthesis of proteins by the cloned pagC locus

To detect if other proteins were encoded by pagC and to determine the approximate size of the pagC gene product, an in vitro coupled transcription/translation analysis was performed. A 5.3 kilobase EcoRI fragment of pWP061 was inserted into pUC19 so that the pagC gene would not be expressed off the lac promotor. This plasmid was used in an in vitro coupled transcription-translation assay. A single protein of approximately 22 kilodaltons was synthesized by the cell free system. The size was compatible with this being the precursor of the PagC protein containing its leader peptide. These data further support the conclusion the single and the single pagC gene product had been identified.

Identification of the pagC encoded RNA

An approximately 1100 nucleotide RNA is encoded by pagC. The pagC gene is highly expressed by cells with a phoP constitutive phenotype of pag activation, as compared to wild type and phoP constitutive phenotype of pag activation, as compared to wild type and phoP⁻ bacteria. In these blot hybridization experiments pagC is only detected in wild type cells grown in rich media during stationary growth. This result, coupled with previous work, Miller et al., 1989, supra, Miller et al., 1990, supra, demonstrates that pagC is transcriptionally regulated by the phoP gene products and is only expressed during early logarithmic phase growth in rich media by cells with a phoP constitutive phenotype.

The size of the pagC transcript is approximately 500 nucleotides greater than that necessary to encode the 188 amino acid protein. Primer extension analysis of Salmonella RNA using oligonucleotide primers specific for pagC sequence was performed to determine the approximate start site of transcription and to determine whether these nucleotides might be transcribed 5' or 3' to the 188 amino acid pagC gene product. Primer extension analysis with an oligonucleotide predicted to be complementary to nucleotides 550–565 of pagC, 150 nucleotides 5' to the predicted start codon, resulted in an approximately 300 nucleotide primer extension product. Therefore a primer further upstream was constructed complementary to nucleotides 335–350 of pagC and used in a similar analysis. A primer extension product of 180 nucleotides was observed to be primer specific. This is consistent with transcription starting at nucleotide 170 (FIG. 3). Upstream of the predicted transcriptional start, at nucleotides 153–160, a classic RNA polymerase binding site was observed with the sequence TATAAT at −12 nucleotides as well as the sequence TAATAT at −10 nucleotides. No complete matches were observed for the consensus RNA polymerase recognition site (TTGACA) 15–21 nucleotides upstream from the −10 region. AT −39 (126–131) nucleotides (TTGGAA), −38 (127–132) nucleotides (TTGTGG), and −25 (135–140) nucleotides (TTGATT) are sequences that have matches with the most frequently conserved nucleotides of this sequence.

Based on the above results transcription was predicted to terminate near the translational stop codon of the 188 amino acid protein (nucleotide 1295, FIG. 3). Indeed, a stem loop configuration was found at nucleotides 1309–1330 that may function as a transcription terminator. This was consistent with the lack of evidence of open reading frames downstream of the 188 amino acid protein and the lack of synthesis of other transcription/translation using the cloned pagC DNA. This further suggests that the pagC::TnphoA insertion inactivated the synthesis of only a single protein.

Similarity of PagC to Ail and Lom

A computer analysis of protein similarity using the National Biomedical Research Foundation/Protein Identification Resource, George et al., 1986, Nucleic Acids Res. 14:11–15, hereby incorporated by reference, protein sequence base was conducted to identify other proteins that had similarity to PagC in an attempt to find clues to the molecular function of this protein. Remarkably, PagC was found to be similar to a bacteriophage lambda protein, Lom, that has been localized to the outer membrane in minicell analysis, Court et al., 1983, Lambda II, Hendrix, R. W. et al. ed. Cold Spring Harbor Laboratory (Cold Spring Harbor N.Y.), pp. 251–277, hereby incorporated by reference, and demonstrated to be expressed by lambda lysogens of E. coli, Barondess, et al., 1990, Nature 346:871–874, hereby incorporated by reference. Recently, the deduced amino acid sequence of the cloned ail gene product of Y. enterocolitica was determined and found to also be similar to Lom, Miller et al., 1990b, J. Bacteriol. 172:1062–1069. Therefore, a protein family sequence alignment was performed using a computer algorithm that establishes protein sequence families and consensus sequences, Smith et al., 1990, Proc. Natl. Acad. Sci. 87:118–122, hereby incorporated by reference. The formation of this family is indicated by the internal data base values of similarity between these proteins : PagC and Lom (107.8), PagC and Ail (104.7), and Ail and Lom (89.8). These same proteins were searched against 314 control sequences in the data base and mean values and ranges were 39.3 (7.3–52.9) PagC, 37.4 (7.3–52.9) Ail, and 42.1 (7.0–61.9) Lom. The similarity values for this protein family are all greater than 3.5 standard deviations above the highest score obtained for similarity to the 314 random sequences. No other similarities or other family members were found in the database. Regions of similarity are located not only in the leader peptide transmembrane domains but throughout the protein.

pag Mutant Strains Are Attenuated For Virulence

*Salmonella typhimurium* strains of the invention with a pagC mutation were attenuated for virulence by least 1,000-fold.

In addition pagC, other pag genes described herein may be useful in the development of live Salmonella vaccines. Mutations in phoP-activated genes could be used to construct attenuated, live Salmonella vaccines. In constructing multivalent Salmonella vectored vaccines, PhoP-activated promoters could increase immunogenecity by targeting foreign protein expression to antigen presenting macrophages. Identification of novel phoP-activated genes.

To further analyze the role of phoP-activated genes in bacterial virulence, a bank of strains with active phoA gene fusions was generated by TnphoA mutagenesis. Strain CS019 was the parent strain for TnphoA mutagenesis because it has wild-type bacterial virulence and carries the phoN2 allele, which results in minimal background phosphatase activity. Strains with active phoA gene fusions were identified by blue colony phenotype after growth in agar containing XP. Such strains were then screened for decreased fusion protein activity on acquisition of the phoP12 allelle that results in a PhoP-null phenotype.

Two thousand and sixty-four AP expressing strains were isolated and colony purified from two hundred and forty independent matings. Strains with AP activity were isolated at a frequency of 0.8% from the total pool of kanamycin resistant (TnphoA containing) bacteria. A total of fifty-four candidate pag::TnphoA insertions were isolated from the AP expressing strain bank, and forty-nine of these were determined to have greater than six-fold reduction in AP activity in the absence of functional phoP/phoQ. Therefore, approximately 2% of the colonies expressing AP were identified as pag-phoA gene fusions.

Identification of thirteen unique pag loci

Three methods were used to determine whether the forty-nine TnphoA insertions defined unique pag loci. First, physical maps of the EcoRI and HindIII restriction endonuclease sites 5' to the TnphoA insertions were defined. Second, linkage analysis to transposon insertions highly linked to known pag loci was performed. Third, strains determined to be unique by the above methods were screened for linkage to a bank of strains with transposon insertions of known chromosomal location.

Blot hybridization analysis demonstrated that thirteen of the forty-nine strains had unique restriction endonuclease sites 5' to the TnphoA insertion. The numbers of strains with similar physical maps 5' to the TnphoA insertion ranged from 1–7. One of the thirteen physical maps was similar to that expected for an insertion in pagC and was noted in seven of the strains isolated as containing candidate pag::TnphoA insertions. Analysis of these seven strains indicated that only three of these were pagC::TnphoA insertions, since blot hybridization analysis with a fragment of pagC as a probe and linkage analysis to transposon insertions highly linked to pagC indicated that four of these insertions were not in pagC. Another of the pag::phoA fusions, denoted pagP, had the physical 5' restriction-endonuclease map that would be expected for phoN. However, this insertion was determined not to be within phoN by linkage analysis and blot hybridization. A

TABLE 12

Bacterial strains.

| Strain | Genotype | Source |
|---|---|---|
| *S. typhimurium* | | |
| 14082s | Wild type | ATCC |
| CS019 | phoN2 zxx::6251Tn10d-Cm | 25 |
| CS015 | phoP-102::Tn10d-Cm | 25 |
| AD154 | phoP12 purB1744::Tn10 | 3 |
| TT13208 | phoP105::Tn10d | 26 |
| CS585 | pagD1::TnphoA phoN2 zxx::6215Tn10d-Cm | This study |
| CS586 | pagD1::TnphoA phoP105::Tn10d phoN2 zxx::6215Tn10d-Cm | This study |
| CS619 | pagE1::TnphoA phoN2 zxx::6215Tn10d-Cm | This study |
| CS620 | pagE1::TnphoA phoP105::Tn10d phoN2 zxx::6215Tn10d-Cm | This study |
| CS1599 | pagF1::TnphoA phoN2 zxx::6215Tn10d-Cm | This study |
| CS1600 | pagF1::TnphpoA phoP105::Tn10d phoN2 zxx::6215Tn10d-Cm | This study |
| CS334 | pagG1::TnphoA phoN2 zxx::6215Tn10d-Cm | This study |
| CS335 | pagG1::TnphoA phoP105::Tn10d phoN2 zxx::6215Tn10d-Cm | This study |
| CS1488 | pagH1::TnphoA phoN2 zxx::6215Tn10d-Cm | This study |
| CS1489 | pagH1::TnphoA phoP105::Tn10d phoN2 zxx::6215Tn10d-Cm | This study |
| CS2054 | pagI1::TnphoA phoN2 zxx::6215Tn10d-Cm | This study |
| CS2055 | pagI1::TnphoA phoP105::Tn10d phoN2 zxx::6215Tn10d-Cm | This study |
| CS1074 | pagJ1::TnphoA phoN2 zxx::6215Tn10d-Cm | This study |
| CS1075 | pagJ1::TnphoA phoP105::Tn10d phoN2 zxx::6215Tn10d-Cm | This study |
| CS767 | pagK1::TnphoA phoN2 zxx::6215Tn10d-Cm | This study |
| CS768 | pagK1::TnphoA phoP105::Tn10d phoN2 zxx:6215Tn10d-Cm | This study |
| CS993 | pagL1::TnphoA phoN2 zxx::6215Tn10d-Cm | This study |
| CS994 | pagL1::TnphoA phoP105::Tn10d phoN2 zxx::6215Tn10d-Cm | This study |
| CS1845 | pagM1::TnphoA phoN2 zxx::6215Tn10d-Cm | This study |
| CS1846 | pagM1::TnphoA phoP105::Tn10d phoN2 zxx::6215Tn10d-Cm | This study |
| CS728 | pagN1::TnphoA phoN2 zxx::6215Tn10d-Cm | This study |
| CS729 | pagN1::TnphoA phoP105::Tn10d phoN2 zxx::6215Tn10d-Cm | This study |
| CS1194 | pagO1::TnphoA phoN2 zxx::6215Tn10d-Cm | This study |
| CS1195 | pagO1::TnphoA phoP105::Tn10d phoN2 zxx::6215Tn10d-Cm | This study |
| CS1247 | pagP1::TnphoA phoN2 zxx::6215Tn10d-Cm | This study |
| CS1248 | pagP1::TnphoA phoP105::Tn10d phoN2 zxx::6215Tn10d-Cm | This study |
| AK3011-3314 | Collection of Randomly spaced Tn10 Δ16Δ17 insertions | 18 |
| *E. coli* | | |

TABLE 12-continued

Bacterial strains.

| Strain | Genotype | Source |
|---|---|---|
| SM10(pRT291) | Contains plasmid pRT291 (TnphoA) derived from pRK290 selecting for Tet[r] and Km[r] | 37 |
| MM294(pPHIJI) | Contains Gm[r] plasmid pPHIJI, which is in incompatible with pRK290 | 37 |

3 Behlau et al., 1993, J. Bacteriol., 175:4475–84
18 Lehrer et al., 1991, Cell, 64:229–30
25 Miller et al., 1989, Proc. Natl. Acad. Sci. USA, 86:5054–58
26 Miller et al., 1990, J. Bacteriol., 172:2485–90
Taylor et al., 1989, J. Bacteriol., 171:1870–78 transductional cross was performed between wild type bacteria and strain CS1247 containing pagP::TnphoA and zxx::6215Tn10d-cam. These transductants were selected on kanamycin, insuring the inheritance of the pagP::TnphoA which encodes kanamycin resistance. These colonies were then screened for choramphenicol resistance which would indicate linkage of zxx:6215Tn10d-cam to pagP. No linkage was found indicating that pagP was not linked to phoN. Blot hybridization using a portion of phoN as a probe was also performed on CS1247 and indicated that this strain contained a wild type phoN locus. Thirteen pag loci were defined and designated pagD-P.

To further define the phoP regulation of the 13 Pag::TnphoA fusion proteins, AP activity was assayed in strains isogenic except for the phoP locus. AP activity was assayed during bacterial growth in rich medium in logarithmic and stationary growth phase (Table 13). The dependence of an intact phoP locus for full expression remained constant for the different stages of growth; however, the relative amount of AP expression increased as growth was limited. The difference in expression of pag gene fusions varied from six to forty-eight fold when isogenic strains with a wild type and null phoP locus were compared.

Of the five previously identified pag loci, only phoN, pagC, and pagA have known chromosomal locations. Linkage analysis of the 13 newly identified pag loci was performed using strains containing transposon insertions linked to pagC (AK3233 and AK3140), and to pagA (AK3255). Three pag::TnphoA insertions were found to be linked to AK3140 which is in a region near pagC at 24–25 minutes on the chromosome. These were designated pagD, pagE, and pagF. PagD::TnphoA was similarly linked to the transposon insertion of AK3233 (83%) and AK3140 (33%) as was previously reported for pagC. The TnphoA insertion of this strain has been further defined and is divergently transcribed from pagC. pagE and pagF exhibited different linkage to the insertions of AK3233 and AK3140 than pagC and pagD suggesting a significantly different chromosomal location. The pagE::TnphoA insertion is 39% linked to the transposon insertion of AK3233 and 99.1% linked to that of AK3140, while pagF::TnphoA is 31% linked to the insertion of AK3140 but not to that of AK3233. These different linkages in addition to the physical maps of the restriction endonuclease sites 5' to the TnphoA insertion indicated that these were new pag loci. Therefore, three new pag loci were found in the region of 25 minutes, one of which is highly linked to the previously defined pagC.

Linkage analysis was then performed using a group of defined random Tn10Δ16Δ17 insertions on the ten strains with TnphoA insertions of no known location. Of these ten pag::TnphoA alleles only two demonstrated linkage to the bank of Tn1Δ16Δ17 insertions. The pagG::TnphoA insertion was demonstrated to have 97% linkage to the transposon insertion of AK3258 located at approximately 30 minutes. The pag::TnphoA insertion, designated pagH, exhibited 23% linkage to the insertion of AK3091. The linkage to the transposon insertion of AK3091 was similar to linkage previously demonstrated for prgE (26%). Therefore, this chromosomal region contains both phoP-activated and repressed genes. This TnΔ16Δ17 insertion was analyzed using pulse field gradient electrophoresis of chomosomal DNA from AK3091 digested with the restriction endonuclease XbaI and BlnI. These data indicate that the transposon insertion of AK3091 was located in the region of 20–25 minutes and that pagH and prgE are located in this region of the chromosome.

Comparison of pag::phoA activity in strains with wild type and null phoP[-] loci.

| | Activity (Units of AP)[a] | | | | |
|---|---|---|---|---|---|
| | Logarithmic growth | | Stationary growth | | Fold |
| Allele | PhoP[+] | PhoP[-] | PhoP[+] | PhoP[-] | Reduction[b] |
| pagD1::TnphoA | 32 | 2 | 79 | 9 | 16 |
| pagE1::TnphoA | 96 | 2 | 108 | 3 | 48 |
| pagF1::TnphoA | 89 | 4 | 276 | 10 | 22 |
| pagG1::TnphoA | 35 | 1 | 65 | 6 | 35 |
| pagH1::TnphoA | 35 | 5 | 38 | 6 | 7 |
| pagI1::TnphoA | 12 | 2 | 24 | 8 | 6 |
| pagJ1::TnphoA | 123 | 8 | 944 | 88 | 15 |
| pagK1::TnphoA | 30 | 3 | 123 | 26 | 10 |
| pagL1::TnphoA | 7 | 1 | 35 | 4 | 7 |
| pagM1::TnphoA | 92 | 11 | 439 | 130 | 8 |
| pagN1::TnphoA | 23 | 1 | 58 | 2 | 23 |
| pagO1::TnphoA | 31 | 2 | 54 | 12 | 16 |
| pagP1::TnphoA | 33 | 1 | 27 | 3 | 38 |

Strains with pag:TnphoA insertions have wild type sensitivity to the rabbit NP-1 defensin

Figure 6:
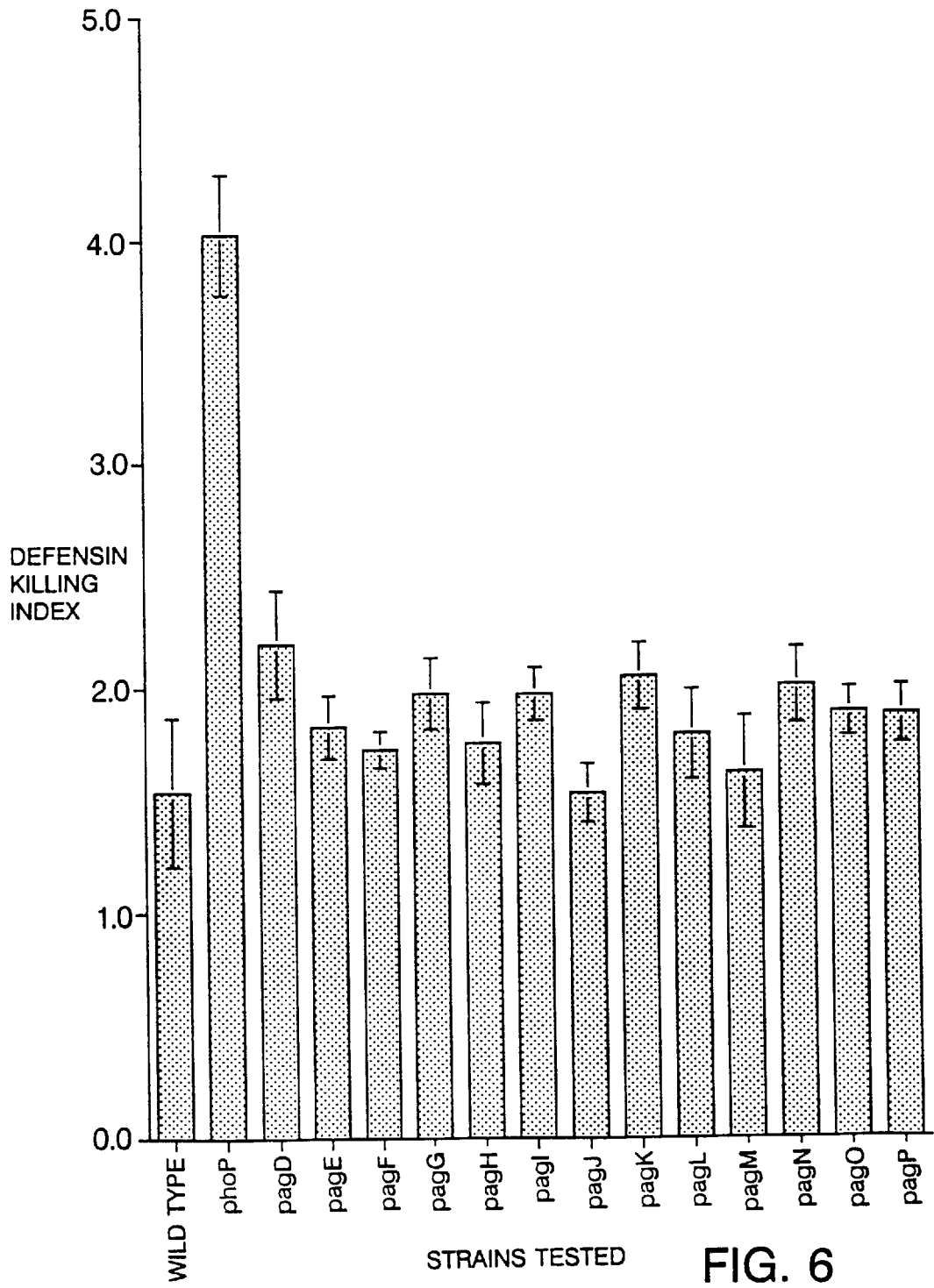

*S. Typhimurium* strains with null mutations in the phoP operon have increased sensitivity to a variety of cationic antimicrobial peptides including defensins, magainins, and protamine. The defensins are a family of mammalian peptides present in the granules of neutrophils, lung macrophages, and intestinal Paneth cells. Resistance to these peptides may contribute to bacterial virulence and the ability to colonize mucosal surfaces. Strains with pag::TnphoA insertions were tested for sensitivity to the highly active rabbit defensin NP-1. None of the strains with single pag::TnphoA insertions demonstrated increased sensitivity to NP-1 defensin (see FIG. 6). Thus despite the demonstrated sensitivity of phoP-null mutants to rabbit defensin NP-1, no defined mutations in pag loci were associated with sensitivity to defensins.

Four strains with pag::TnphoA insertions demonstrate marked attenuation for mouse virulence To further define whether these new pag loci contributed to mouse virulence, the 13 strains with pag transposon insertions were screened in vivo. Mice were injected intraperitoneally with approximately 100 organisms. Four strains with transposon insertions in pagD, pagJ, pagK, and pagM demonstrated attenuated virulence. Mice injected with these strains all survived and showed no signs of systemic infections, such as hepatosplenomegaly and scruffiness (piloerection due to fever). These four strains were subjected to further virulence testing by intraperitoneal injection of multiple doses of organisms in a total of ten mice on two separate occasions. The mean $LD_{50}$ was determined from these subsequent injections and is listed in Table 14. One of these strains, containing the pagD::TnphoA insertion, has a $LD_{50}$ 10,000 fold greater than wild-type S. typhimurium. The other three strains were also markedly attenuated for mouse virulence with $LD_{50}$ values greater than 1000–10,000 times that of wild type organisms. These data indicated that the phoP-regulated loci, pagD, pagJ, pagK, and pagM, when mutated, result in attenuation of bacterial virulence.

pag::TnphoA strains attenuated for mouse virulence have reduced survival within macrophages.

Since phoP mutant Salmonella are deficient in survival within macrophages, strains containing mutations in pag genes that had attenuated mouse virulence were tested for reduced viability within macrophages. As shown Table 14, all strains with pag mutations demonstrated significantly reduced survival within macrophages. Decreased intracellular survival of pag mutants was not observed until a time when pag are predicted to be maximally expressed.

Four strains with mutations in the pagC, pagD, pagJ, pagK and pagM loci were found to be attenuated for mouse virulence and survival within macrophages. Strains with mutations in these five pag all had varying degrees of virulence attenuation. Strains with a mutation in pagJ had a virulence defect comparable to that observed for pagC mutants (greater than 1000× the $LD_{50}$ of wild type organisms). The pagD::TnphoA insertion resulted in the greatest attenuation of virulence, comparable to that of a phoP null mutation (greater than 10,000× the $LD_{50}$ of wild type organisms). pagK and pagM mutants had virulence attenuation that was intermediate between the pagJ and pagD mutants. The cumulative effect of deletion of pagC, pagD, pagJ, pagK, and pagM, if additive and similar to the attenuation observed with TnphoA insertions, may be much greater than that observed by deletion of phoP alone. The observation that many of these genes are somewhat expressed in stationary phase in the absence of phoP suggests that functional Pag proteins could be produced in vivo in the absence of phoP. One virulence gene pagM is significantly expressed in the absence of phoP, though it may still require phoP/phoQ for induction within macrophage phagosomes. This data suggests that deletion of pag gene products could lead to greater virulence attenuation than deletion of the regulatory proteins.

Salmonella envelope proteins as virulence factors: Defensin sensitivity

Based on the methods used to identify pag loci, i.e., translational gene fusions to phoA, and the observation that the pagC gene fusions produce AP, it has now been discovered that many pag encode bacterial envelope proteins. No strains have been found with single pag mutations that confer sensitivity to defensins or other cationic peptides. The data suggest that an alteration of the bacterial envelope as a result of the change in synthesis of the entire aggregate of envelope proteins mediated by PhoP/PhoQ may be important to S. typhimurium virulence.

Defensins are small amphipathic cationic peptides of approximately 30–35 amino acids in length whose antimicrobial action involves penetration and disruption of membranes, possibly by forming selective anionic channels. Though defensins are largely found in neutrophils and Paneth cells these or other related molecules likely contribute to non-oxidative killing of phagocytosed bacteria by macrophages. Though it remains possible that a single unidentified pag encodes a protein responsible for defensin resistance, it seems more likely that a cumulative effect of expression of several pag encoded envelope proteins could result in resistance to defensins. An aggregate change in a large number of bacterial envelope proteins could alter the membrane charge, electrical potential, or lipid content such that defensin interaction with bacterial membranes could be changed.

Identification of transcriptional units linked to pagC

Figure 7:
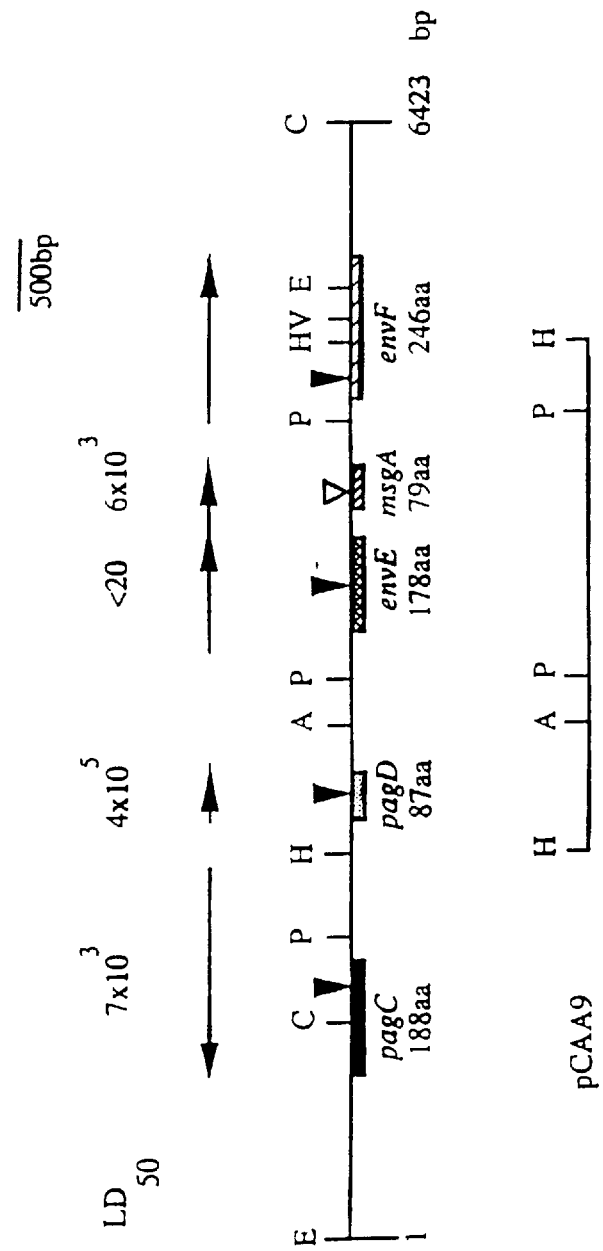

To identify genes upstream of pagC, E. coli carrying plasmid pWPL17 containing 2.8 kb of DNA 5' to pagC (Table 15 and FIG. 7) was mutagenized with the transposons MudJ and TnphoA, and strains with AP or β-galactosidase activity were identified on chromogenic substrates. In addition, as part of an effort to identify additional phoP-activated genes, random mutagenesis of the Salmonella chromosome with TnphoA was performed, and strains with AP activity were screened for TnphoA insertions linked to the Tn10Δ16Δ17 of strain AK3233, which is 75% linked to pagC. Several strains that contained plasmids with active MudJ or TnphoA generated gene fusions were identified. In addition, two strains were identified that contained active chromosomal TnphoA insertions closely linked to pagC. Physical maps of the restriction endonuclease sites surrounding the transposon insertions in strains with active plasmid or chromosomal lacZ and phoA gene fusions were performed to determine the relationship of the transposon insertions to pagC. This analysis revealed that several regions of the DNA were transcribed oppositely to pagC (FIG. 7). Several TnphoA insertions that resulted in active phoA gene fusions were identified. These data indicated that pagC-linked genes encoded membrane or secreted proteins.

The effects of pag::phoA gene fusions on Salmonella mouse virulence.

| Strain | Genotype | $LD_{50}$[a] | MSI[b] | Reference |
|---|---|---|---|---|
| 14028s | Wild type | <20 | 6.13 | 25 |
| CS015 | phoP102::Tn10-Cam | $7.0 \times 10^5$ | 0.40 | 25 |
| CS585 | pagD1::TnphoA | $4.0 \times 10^5$ | 0.01 | 15 |
| CS1074 | pagJ1::TnphoA | $4.0 \times 10^3$ | 0.56 | This study |
| CS767 | pagK1::TnphoA | $9.0 \times 10^4$ | 0.04 | This study |
| CS1845 | pagM1::TnphoA | $3.0 \times 10^4$ | 0.09 | This study |

[a]The 50% lethal dose was determined by intraperitoneal injection of ten mice per dilution using the method of Reed and Muench (31).
[b]The Macrophage Survival Index (MSI) was determined by dividing the mean Salmonella CFU recovered from macrophage cultures (performed in triplicate) 24 hours after the addition of gentamicin by the mean Salmonella CFU recovered from macrophages 1 hour after gentamicin was added.
16 Kier et al., 1979, J. Bacteriol., 138:155–61
25 Miller et al., 1989, Proc. Natl. Acad. Sci. USA, 86:5054–58

TABLE 15

Plasmids, strains and relevent properties

| S. typhimurium strains | Relevent genotypes/information | MSI[a] | Source[b] |
|---|---|---|---|
| ATCC14028 | Wild type | 3.90 | ATCC |
| CS019 | phoN2 zxx::6251Tn10d-Cm | | (31) |
| CS585 | CS019,pagD::TnphoA | 0.002 | (4) |
| CS586 | CS585:phoP105::Tn10d-Tet | | (4) |
| JSG205 | ATCC14028, msgA::MudJ | 0.01 | This work |
| JSG225 | JSG205,phoP105::Tn10d-Tet | | This work |
| CS811 | CS019, envE::TnphoA | | This work |
| CS812 | CS811,phoP105::Tn10d-Tet | | This work |
| CS100 | ATCC14028, phoP105::Tn10d-Tet | 0.01 | derivitive of TT13208 |
| JSG232 | JSG205,envF::pGPP2 | | This work |
| JSG244 | CS019,envF::pGPP2 | | This work |
| JSG235 | JSG234,phoP105::Tn10d-Tet | | This work |
| JSG244 | JSG205,phoP105::Tn10d-Tet | | This work |
| CS099 | ATCC14028;zxx3024::Tn10Δ16Δ17pol-2(Whitfield polA amber) | | This work |
| Other salmonellae | | | |
| Ty2 | Vi positive | | FDA |
| Salmonella paratyphi A | ATCC 9150 | | ATCC |
| Salmonella paratyphi C | ATCC 13428 | | ATCC |
| Salmonella enteriditis | Clinical isolate | | VRI |
| E. coli Strains | | | |
| SM10λpir | thi-1 thr-1 leuB6 supE44 tonA211 lacY1recA::RP4-2-Tc::Mu | | |
| DH5α | F-Ø80dlacZΔM15Δ(lacZYA-argF)U169endA1recA1hsdR17deoRthi-1supE44λ-gyrA96relA1 | | |
| Other Enterobacteriaceae | | | |
| Yersinia enterocolitica | Clinical isolate | | MGH bacteriology lab |
| Vibrio cholerae | Clinical isolate | | Peruvian epidermic |
| Campylobacter fetus | Clinical isolate | | MGH bacteriolog lab |
| Citrobater freudii | Clinical isolate | | MGH bacteriology lab |
| Klebsiella pneumoniae | Clinical isolate | | MGH bacteriolagy lab |
| Shigella flexneri | Clinical isolate | | MGH bacteriology lab |
| Shigella sonnei | Clinical isolate | | MGH bacteriology lab |
| Morganella morganii | Clinical isolate | | MGH bacteriology lab |
| Providencia stuartii | Clinical isolate | | MGH bacteriology lab |
| Plasmids | | | |
| pWPL17 | pBR322 containing a 2.8 Kb HpaI fragment from pWP061 | | This work |
| pCAA9 | pWPL17 containing a TnphoA insertion in envF | | This work |
| pGP704 | pir-dependent suicide vector | | (34) |
| pGPP2 | pGP704 containing the cloned envF::phoA gene fusion | | This work |
| pWP061 | Cosmid clone containing the pagC region | | (36) |

[a]MSI (macrophage survival index) is calculated by dividing the number of surviving organisms at 24 hours post-infection by the number of cell asscociated organisms present after the 30 minute infection.
[b]MGH, Massachusetts General Hospital, ATCC, American Type Culture Collection, FDA, Food and Drug Administration; VRI, Virus Research Institute
4 Belden et al., 1989, Infect. Immun., 57:1–7
31 Miller et al., 1989, Proc. Natl. Acad. Sci. USA, 86:5054–58
34 Miller et al., 1988, J. Bacteriol., 170:2575–83
36 Pulkkinen et al., 1991, J. Bacteriol., 173:86–93

Genes linked to pagC encode four novel proteins

To further analyze the genes defined by transposon insertions, the DNA sequence of this region was determined (FIG. 8). DNA containing this region was cloned; 4 kb of DNA between the HpaI site 737 bp upstream of the start codon of pagC to a ClaI site far upstream was sequenced. The DNA sequence of the fusion junctions of all TnphoA and MudJ gene fusions was also determined. Based on these data, the correct reading frame of each gene was determined. The DNA sequence data revealed four ORFs predicted to be transcribed and translated based on the data derived from the TnphoA and MudJ insertions. All ORFs revealed typical ribosome binding sites 6 to 11 bases from the predicted start of translation. The translation of the ORF immediately upstream and oppositely transcribed to pagC, pagD, indicates that a short envelope protein of 87 amino acids (unprocessed) is encoded. It is followed by a second ORF (envE) which encodes an envelope protein of 178 amino acids (unprocessed). This ORF is followed by a structure that could function as a Rho-independent transcriptional terminator (see FIG. 8). The third ORF, msgA (macrophage survival gene), encodes a small protein similar in size to that of the first gene product (79 amino acids) and is also followed by a structure that could function as a Rho-independent transcriptional terminator (see FIG. 8). The DNA sequence predicts that this protein is composed of several charged residues with a large number of negatively charged amino acids residing at the carboxy terminus. The predicted protein product does not contain a structure resembling a signal sequence at its amino terminus nor any hydrophobic stretches; therefore, the third ORF is unlikely to encode an envelope protein. The final ORF (envF) encodes an envelope protein of 278 amino acids (unprocessed). A computer search of known protein motifs revealed that EnvF contains a consensus prokaryotic membrane lipid attachment site and, therefore, is likely to be a lipoprotein (see FIG. 8 for consensus site location).

The predicted proteins produced by pagD, envE, and envF contain a typical bacterial signal sequence structure. In addition, hydrophobic profiles confirmed the hydrophobic nature of the amino-termini of these proteins. The EnvE and EnvF proteins also contain hydrophobic stretches that could function as membrane spanning domains. The G+C content of the genes in this region are: pagC, 43.4%; pagD, 42.1%; envE, 45.9%; msgA, 46.8%; and envF, 40.5%, which is considerably lower than the average G+C content of *S. typhimurium* (52%). A complete search of the database with the predicted protein sequences of these four ORFs showed no significant similarities. Strains containing three distinct TnphoA insertions and one MudJ insertion, each located in one of the four genes, were chosen for further characterization.

A gene pagD, oppositely transcribed to pagC, is positively regulated by phoP/phoQ Representative strains with transposon insertions were examined to evaluate whether genes transcribed oppositely to pagC were increased in synthesis in the presence of PhoP. To accurately determine if these genes were PhoP regulated, it was necessary to recombine plasmid insertions onto the Salmonella chromosome. Upon replacement of the wildtype gene with the gene containing the transposon insertion, P22HTint lysates made on these strains were transduced into a phoP deleted (PhoP$^-$) strain and AP or β-galactosidase levels were monitored. One of these transposon generated gene fusions demonstrated a significant increase in activity between phoP$^-$ and WT backgrounds, while the other insertions showed no phoP regulation (Table 16).

| Alkaline phosphatase and β-galactosidase gene fusion activity | | |
|---|---|---|
| Strain | Relevent Genotype | gene fusion activity$^a$ |
| JSG205 | msgA:MudJ | 461(B) |
| JSG244 | phoP105::Tn10d-Tet msgA:MudJ | 415(B) |
| JSG226 | envE::TnphoA | 50(A) |
| JSG229 | phoP105::Tn10d-Tet envE::TnphoA | 60(A) |
| JSG204 | pagD::TnphoA | 76(A) |
| JSG225 | phoP105::Tn10d-Tet pagD::TnphoA | 9(A) |
| JSG234 | envF::pGPP2 | 16(A) |
| JSG225 | phoP105::Tn10d-Tet envF::pGPP2 | 19(A) |
| JSG232 | msgA::MudJ envF::pGPP2 | 10(A) |

$^a$(A) AP (alkaline phosphatase) or (B) β-gal (β-galactosidase)

The pagD gene is adjacent to and divergently transcribed from pagC.

The representative transposon insertion in envF was unable to be recombined onto the chromosome, likely due to an insufficient amount of homologous DNA downstream of the transposon. In order to examine the possibility of phoP regulation of the envF gene, a region upstream of this gene through and including the phoA gene of the TnphoA transposon was cloned as a 3-kb PvuI (blunt-ended)-XhoI fragment into the EcoRV-SalI sites of the suicide vector pGP704. This clone was mated into Salmonella strain CS019, and ampicillin-resistant recombinants were selected (creating a strain designated envF::pGPP2). A phoP105::Tn10d-Tet mutation was transduced into this strain to create an isogenic pair differing only in the ability to produce a functional PhoP protein. As shown in Table 16, the introduction of the phoP105::Tn10d-Tet had no effect on the AP levels of these two strains, demonstrating that envF is not a phoP-activated gene.

Transposon insertions in pagC-linked genes attenuate virulence and cause reduced survival within macrophages Since transposon insertions in pagC significantly increase the LD$_{50}$ of *S. typhimurium* in BALB/c mice, strains containing transposon insertions linked to pagC were evaluated for attenuation of mouse virulence. As shown in FIG. 7, while the transposon insertion in envE had no affect on strain virulence, a TnphoA insertion in pagD and the MudJ insertion 1.8 kb downstream in msgA attenuate *S. typhimurium* virulence by greater than 300 fold as compared to wild-type organisms (LD$_{50}$<20 organisms). These data suggested that these two loci are essential to virulence.

To examine the survival capabilities of those strains having a virulence defect, *S. typhimurium* containing insertions in either pagD or msgA were used to infect bone marrow-derived macrophages. The results, shown in Table 15, demonstrate a macrophage survival defect for these two strains. The survival defect is greater for the pagD insertion (MSI=0.002) compared with the msgA insertion (MSI=0.01), and both defects are equal to or greater than that of the PhoP$^-$strain (MSI=0.01).

Transposon insertions in this gene could not be recombined onto the chromosome. Thus, it was necessary to demonstrate that the virulence and macrophage survival defects of msgA was not due to a polar effect of the MudJ insertion on envF transcription. Therefore, pGPP2 was recombined into the msgA::MudJ strain and AP activity of this strain was compared to that of CS019 containing the recombinant pGPP2. This data (shown in Table 16) demonstrates that the transcription of the envF gene is unaffected by the msgA::MudJ insertion and is transcribed from its own promoter. However, it is possible that under different environmental conditions, other promoters may be activated that could place msgA and envF on the same transcript.

Determination of the msgA and pagD transcriptional start sites

The 5' regions of these genes were examined to define the transcriptional start sites of msgA and pagD. Oliogonucleotides complimentary to the 5' end of each ORF or upstream region were used in a primer extension analysis. The results of this analysis revealed that the pagD transcript begins 39 bases upstream of the translational start. The predicted −10 (TTCCAT) and −35 (TTGAAT) regions were found to be similar to the known consensus sequences for *E. coli* promoters. The pagD transcript was detected only in phoP$^c$ Salmonella RNA and not in RNA from phoP$^-$ Salmonella. The msgA transcriptional start was found to begin 58 bases upstream of the translational start and contain predicted −10 (CAAAAC) and −35 (TTACGT) sequences. These regions do not conform well to consensus −10 and −35 sequences; however, the cDNA from this transcript was easily detected using various primers in primer extensions of both phoP$^c$ and phoP$^-$ RNA and appears to produce an abundant RNA. Distribution of pagD and msgA genes in the Enterobacteriaceae and in two G+C content organisms The G+C content of the pagC chromosomal region is much lower than the average G+C content of Salmonella. The gene encoding the phoP-regulated acid phosphatase of *S. typhimurium* (phoN) also has a low G+C content (39%), and DNA homologous to phoN was found only in two low G+C organisms of several genera tested. The DNAs of several members of the Enterobacteriaceae and two low G+C organisms were examined for similarity to pagD and msgA by blot hybridization. PCR fragments highly specific to each ORF were labeled and used as probes. This analysis demonstrated hybridization at high stringency to all Salmonella species examined as well as *Shigella sonnei, Shigella*

*flexneri, Klebsiella pneumoniae* and *Citrobacter freundii*. No hybridization was seen to the low G+C organisms *Morganella morganii* or *Providencia stuartii*. Identical hybridization patterns were seen with probes specific for both genes indicating that these genes are also linked in organisms other than Salmonella.

A virulence gene cluster required for *Salmonells typhimurium* survival within macrophage macrophages Four genes upstream and oppositely transcribed to the pagC gene of *Salmonella typhimurium* have now been identified. Three genes (pagD, envE and envF) are predicted to be envelope proteins based on the isolation of active TnphoA insertions in these loci and the presence of a typical signal sequence at the amino-terminus of each protein. None of the four proteins possess significant homology to any protein in the database.

Only the gene immediately upstream of pagC and oppositely transcribed (pagD) was determined to be phoP regulated. Transposon insertions in this gene greatly attenuate virulence and the ability of the organism to survive within murine macrophages. The transcription of several pag (including pagC) has been shown to be induced when Salmonella are within macrophage phagosome. In addition, analysis of proteins produced by Salmonella after infection of macrophage-derived cell lines indicate that pag products are induced and that PagC may be among the most abundant gene products induced upon macrophage infection. Since pagD is required for macrophage survival, it is likely that the transcription of this gene also will be induced within macrophage phagosomes. The PagD protein is small (87 amino acids, unprocessed) and has no strong hydrophobic domains; therefore, it is likely that it is a periplasmic or secreted protein.

Transposon insertions in the msgA gene were found to have an effect on mouse virulence and macrophage survival. It is likely that this gene may also be induced within acidified macrophage phagosomes as are other genes necessary for macrophage survival. If this gene is induced by the macrophage environment, its expression (as well as other genes necessary for macrophage survival) may be controlled by a regulatory system separate from the phoP/phoQ system.

These pagC-linked genes do not appear to form an operon. Because none of the genes downstream of pagD are phoP regulated, they appear not be transcribed from the pagD promoter. The presence of a potential transcriptional terminator at the end of the envE gene makes it unlikely that msgA is co-transcribed with envE. The data suggest that the msgA::MudJ insertion is not polar on envF, which suggests that envF has its own promoter. Additionally, a potential transcriptional terminator following msgA as well as a 493 bp intergenic region makes it unlikely that these genes are co-transcribed. Primer extension analysis of these genes confirms that all four genes are transcribed from their own promoter.

The other two genes identified in this region, envE and envF, appear to produce membrane proteins that contain characteristic membrane spanning regions. The envF gene product is likely to be a lipoprotein based on the presence of a consensus lipid attachment site, and is likely to play a role in *Salmonella virulence*.

The low G+C content of the genes in the pagC region suggests that they may have been acquired by horizontal transmission. Southern blot analysis of low G+C organisms probed with the msgA or pagD genes showed no homology, but this does not eliminate the possibility that they were acquired from another low G+C content organism. The possibility also exists that these genes reside on a mobile genetic element acquired from another source. The msgA and pagD probes hybridized in identical patterns to some members of the Enterobacteriaceae other than Salmonella. However, the pagC gene has been shown to be unique to Salmonella species. This may indicate that the products of the genes upstream of pagC do not form a complex with PagC or that their functions do not require PagC interaction. Alternatively, because proteins that have homology to PagC exist in other Enterobacteriaceae (in the absence of any DNA homology), a PagC homolog may be linked to msgA and pagD in other species which was not detected by the DNA hybridization experiments.

pagC/pagD promoter region: expression of heterologous proteins pagC and pagD are divergently transcribed and are both PhoP activated. Other divergently transcribed, regulated genes are known in the art (Beck et al., 1988, Microbiol. Rev. 52:318–326), e.g., the *Klebsiella pneumoniae* pulA-malX region (Chapon et al., 1985, J. Bacteriol. 164:639–645). Transcription of most of such genes require accessory proteins, such as CAP, in addition to the regulator to activate transcription. These two genes are divergently transcribed, and their promoters are arranged back-to-back. A region of 134 bp exists between transcriptional start sites of these genes, which is similar to the intergenic region between pagC and pagD. The pulA-malK promoter region is predicted to contain two MalT (the regulatory protein of this system) binding sites, one for each gene. Other MalT-activated genes require the CAP protein for expression, but the pulA and malX genes do not, possibly because of the high local concentration of the MalT regulator. Since the region between the transcriptional start sites of pagC and pagD (the predicted −35 sequences) is only 137 bp (nucleotides 562 to 776 of SEQ ID NO:15), it is likely that only PhoP binding sites exist in the intergenic region, and that binding of one or more phosphorylated PhoP molecules positively regulates both genes. This pagC/pagD intergenic region which contains the divergent promoters can be used to construct vectors to express two heterologous proteins, one in each direction.

prg genes

As discussed above, phoP/phoQ constitutive mutations (phenotype PhoP$^c$ ) increase the expression of pag and repress the synthesis of approximately 20 proteins encoded by phoP-repressed genes (prg). phoP$^c$ bacteria are attenuated for mouse virulence suggesting that prg are virulence genes.

By use of the transposon, TnphoA, five unlinked prg loci were identified. In general, media conditions (starvation) that activate pag expression repress prg expression. One prg locus, prgH, was demonstrated to contribute to mouse virulence by both the oral and the intraperitoneal route. Both prgH as well as phoP$^c$ mutant *S. typhimurium* were found to be defective in induction of endocytosis by epithelial cells. Identification and mutation of such virulence genes will be useful in vaccine development.

Nucleotide sequence of the prg H, prgI, prgJ, and prgK genes

SEQ ID NO:10 represents the nucleotide sequence of a 5100-bp HindIII fragment that contains the hyperinvasive hil locus. Four ORFS encoding four prg genes are located within this DNA (see FIG. 9). The ATG start codon is underlined; the asteriks indicate the positions of the prgH, prgI, prgJ, and prgK stop codons. These prg loci are required for bacterial invasion of epithelial cells, full mouse virulence, and transepithelial neutrophil migration. A bacteria attenuated by a mutation in one or more of these loci can be used to vaccinate individuals against infection by the wild type pathogen.

Strains, materials and methods

All bacterial strains used in the characterization of prg genes are listed in Table 5.

TABLE 5

| Strain | genotype or description | Relevant Reference or source |
|---|---|---|
| *S. typhimurium* | | |
| 14028s derivatives | | |
| 14028s | Wild type | ATCC |
| CS002 | phoP12 | This work |
| CS003 | ΔphoP ΔpurB | This work |
| CS012 | pagA1::Mu dJ | This work |
| CS013 | pagB1::Mu dJ | This work |
| CS119 | pagC1::TnphoA phoN2 zxx::6251 Tn10d-Cm | This work |
| CS015 | phoP-102 ::Tn10 d-Cm | This work |
| CS019 | phoN2 zxx::6251Tn10d-Cm | This work |
| CS022 | pho-24 | This work |
| CS023 | pho-24 phoN2 zxx::6251Tn10d-Cm | This work |
| CS030 | phoN2 zxx::6251Tn10d-Cm phoP12 | This work |
| AD154 | phoP12 purB1744::Tn10 | Gift of E. Eisenstadt |
| CS031 | pho-24 purB1744::Tn10 | This work |
| IB001 | phoN2 zxx::6251Tn10d-Cm ΔphoP ΔpurB | This work |
| IB002 | CS030 with prgA1::TnphoA | This work |
| IB003 | IB002 with pho-24 purB1744::Tn10 | This work |
| IB004 | IB002 with phoP12 purB1744::Tn10 | This work |
| IB005 | CS019 with prgA1::TnphoA | This work |
| IB006 | CS015 with prgA1::TnphoA | This work |
| IB007 | CS030 with prgB1 ::TnphoA | This work |
| IB008 | IB007 with pho-24 purB1744::Tn10 | This work |
| IB009 | IB007 with phoP12 purB1744::Tn10 | This work |
| IB010 | CS019 with prgB1 ::TnphoA | This work |
| IB011 | CS015 with prgB1 ::TnphoA | This work |
| IB012 | CS030 with prgB2::TnphoA | This work |
| IB013 | IB012 with pho-24 purB1744::Tn10 | This work |
| 1B014 | IB012 with phoP12 purB1744::Tn10 | This work |
| IB015 | CS019 with prgB2::TnphoA | This work |
| IB016 | CS015 with prgB2::TnphoA | This work |
| IB017 | CS030 with prgC1::TnphoA | This work |
| IB018 | IB017 with pho-24 purB1744::Tn10 | This work |
| IB019 | IB017 with phoP12 purB1744::Tn10 | This work |
| IB020 | CS019 with prgC1::TnphoA | This work |
| IB021 | CS015 with prgC1::TnphoA | This work |
| IB022 | CS030 with prgE1::TnphoA | This work |
| IB023 | IB022 with pho-24 purB1744::Tn10 | This work |
| IB024 | IB022 with phoP12 purB1744::Tn10 | This work |
| IB025 | CS019 with prgE1::TnphoA | This work |
| IB026 | CS015 with prgE1::TnphoA | This work |
| IB027 | CS030 with prgE2::TnphoA | This work |
| IB028 | IB027 with pho-24 purB1744::Tn10 | This work |
| IB029 | IB027 with phoP12 purB1744::Tn10 | This work |
| IB030 | CS019 with prgE2::TnphoA | This work |
| IB031 | CS015 with prgE2::TnphoA | This work |
| IB032 | CS030 with prgE3::TnphoA | This work |
| IB033 | IB032 with pho-24 purB1744::Tn10 | This work |
| IB034 | IB032 with phoP12 purB1744::Tn10 | This work |
| IB035 | CS019 with prgE3::TnphoA | This work |
| IB036 | CS015 with prgE3::TnphoA | This work |
| IB037 | IB001 with prgH1::TnphoA | This work |
| IB038 | IB037 with pho-24 purB1744::Tn10 | This work |
| IB039 | IB037 with phoP12 purB1744::Tn10 | This work |
| IB040 | CS019 with prgH1::TnphoA | This work |
| IB041 | CS015 with prgH1::TnphoA | This work |
| IB042 | Tn5B50-380 in OB040 | This work |
| IB043 | pWKSH5 in IB040 | This work |
| IB044 | pWKSH5 in CS022 | This work |
| CS032 | oxiA1049::Mu d1–8 supD10 | This work |
| CS033 | oxiC1048::Mu d1–8 supD10 | This work |
| CS034 | oxiE4:: Mu d1 ΔnadA100 | This work |
| Other *S. typhimurium* derivatives | | |
| AK3011–AK3314 randomly spaced Tn10Δ16Δ17 insertions | | Collection of (19) |
| TT520 | sr1-202::Tn10 | (41) |

TABLE 5-continued

| Strain genotype or description | | Relevant Reference or source |
|---|---|---|
| TT2979 | sr1-211::Tn5 | (41) |
| TN3061 | zcf-845::Tn10 dcp-1 zhg-1635::Tn10dCm (41) | |
| SH7782 | ompD::Tn5 | (41) |
| x4115 | invA::cat | (13) |
| EE517 | Δhil-517 (Tn5B50-380) | Gift of C. Lee |
| JF897 | oxiA1049::Mu d1–8 supD10 | (2) |
| JF896 | oxiC1048::Mu d1–8 supD10 | (2) |
| JF739 | oxiE4::Mu d1 ΔnadA100 | (2) |
| *S. enteritidis* | | |
| CDC5 | clinical wild-type isolate | (45) |
| SM7 | Str$^r$ smb | (45) |
| *E. coli* | | |
| SM10 (pRT291) | contains plasmid pRT291 (TnphoA) derived from pRK290 selecting for Tc$^r$ and Km$^r$. | (49) |
| MM294 (pPH1JT) | contains Gm$^r$ plasmid pPH1JI, which is incompatible with pRK290 | (49) |
| VV42(pWKSH5) | contains plasmid pWKSH5, a derivative of pSC101 that contains a 5.1 kb HindIII fragment of hil DNA including prgH V. Bajaj and C. Lee | (51) |

(19) Kukral et al., Journal of Bacteriology, 169:1787–1793, 1987
(41) Sanderson et al., Microbiological Reviews, 52:485–532, 1988
(13) Galan et al., Infection and Immunity, 59:3116–3121, 1990
(2) Aliabadi et al., Journal of Bacteriology, 165:780–786, 1986
(45) Stone et al., Journal of Bacteriology, 174:3945–3952, 1992

Bacteria were grown as follows: Luria-Bertani (LB) broth was used as rich medium. Antibiotics were used in the following concentrations in growth media or agar: ampicillin 100 μg/ml (Ap), chloramphenicol 25 μg/ml (Cm), gentamicin 30 μg/ml (Gm), kanamycin 45 μg/ml (Km), and tetracycline 25 μg/ml (Tc). The chromogenic substrate 5-bromo-4-chloro-3-indolyl-phosphate (p-toluidine salt) (XP) was used to detect phosphatase activity on agar at a final concentration of 40 μg/ml. p-nitrophenyl phosphate (p-NPP) was used as a substrate for quantitative measurement of AP activity. Media was buffered to various pH ranges with 1M sodium citrate. E media (Vogel-Bonner minimal) was prepared as described by Davis et al., 1980, Advanced Bacterial Genetics: A Manual for Genetic Engineering. Cold Spring Harbor Laboratory, Cold Spring Harbor, N.Y. Nitrogen-, carbon-, and phosphate free medium (N$^-$C$^-$P$^-$) was prepared as described by Kier et. al., 1977, J. Bacteriol. 130:399, herein incorporated by reference.

This starvation medium was supplemented with 0.04% (wt/vol) glucose as the carbon source, 10 mM NH$_4$Cl as the nitrogen source, and 1 mM NaH$_2$PO$_4$.H$_2$O as the phosphate source. The carbon concentration is one log less than described by Kier et al., supra.

AP activity of strains isogenic except for mutations in the phoP locus was measured in cultures grown from a single colony inoculum under various oxygen tensions with or without shaking at 37° C. Anaerobic cultures were grown in an anaerobic chamber (Coy Laboratories Products, Inc.) with a gas mixture of 80% N$_2$, 10% O$_2$, and 10% CO$_2$ at 37° C. For acid regulation, aliquots of mid-logarithmic cultures were removed to measure initial pH and AP activity. 1M sodium citrate (pH>6.0) or 1M citric acid (pH 4.7) were added to equivalent amounts of culture to a final concentration of 50 mM citrate. Cultures were grown aerobically for two hours at 37° C. and then pH and AP measurements were taken. AP activity was measured as described previously (Michaelis et al., 1983, J. Bacteriol. 154:366–374, herein incorporated by reference). AP units were calculated by the following formula: units={OD$_{420}$/[time (minutes)× volume×OD$_{600}$]}×1000 as defined by Miller for β-galactosidase (Miller et al., 1972, Experiments in molecular genetics, p. 352–355. Cold Spring Harbor Laboratory, Cold Spring Harbor, N.Y.).

Standard bacterial genetic techniques were used to study prg loci. Bacteriophage P22HTint-mediated transduction was performed as according to methods known in the art. TnphoA mutagenesis was performed using a broad host range plasmid (pRT291) to deliver TnphoA (Taylor et al., 1989, J. Bacteriol. 171:1870, herein incorporated by reference). Transpositions of TnphoA into Salmonella DNA were identified by use of the incompatibility plasmid pPH1JI (Taylor et al., supra) . Screening for phoP-repressed genes was performed using CS031, the donor strain of the pho-24 allele. CS031 was constructed by a P22 bacteriophage transductional cross between strains AD154 and CS022 which contains the purB::Tn10 allele and the pho-24 allele, respectively. The linkage of pho-24 and purB::Tn10 was 70%, similar to the linkage of purB to other phoP alleles. Therefore, when P22 bacteriophage transductional crosses were performed between CS031 and the strains containing active gene fusions to phoA, strains could be screened for loss of fusion protein activity on acquisition of tetracycline resistance. Initial screening involved detection of loss of AP activity in approximately 70% of colonies that acquired tetracycline resistance, as they were presumed to contain the pho-24 allele. In addition, controls were performed using strain AD154 that contains the same purB::Tn10 allele linked to a phoP null allele, phoP12. Plasmid DNA was transformed into *S. typhimurium* strain LB5010 by the calcium chloride and heat shock procedure (Maclachlan et al., 1985, J. Bacteriol. 161:442).

Isolation of strains with TnphoA insertions in phoP-repressed genes

Constitutive mutations in the phoP locus (phenotype PhoP$^c$) that result in increased expression of pag in an unregulated fashion also markedly attenuate *S. typhimurium* virulence and survival within macrophages. The virulence defect of phoP$^c$ strains can be explained by their decreased expression of approximately 20 polypeptides encoded by phoP-repressed genes (prg).

A PhoP$^-$PhoN$^-$ strain (IB001) was constructed by a P22 transductional cross between CS019 and CS003. IB001 was then mutagenized with TnphoA (so that background acid phosphatase, encoded by phoN, would not interfere with the measurement of fusion protein activity on alteration of the phoP locus) and 1800 individual blue colonies with PhoA fusion protein activity were isolated on LB agar plates containing XP. These colonies were the result of 18 separate matings with approximately 20 pools in each. These strains were tested for reduction of fusion protein activity on acquisition of the pho-24 allele (CS031), which resulted in a PhoP$^c$ phenotype. AP assays were then performed on strains isogenic except for the phoP locus.

The PhoP$^c$ phenotype was confirmed in these strains by preparation of whole cell protein extracts and SDS-PAGE analysis. All strains with a PhoP$^c$ phenotype demonstrated the expected distinctive pattern of protein expression in phoP$^c$ strains, i.e. repressed protein species of specific sizes.

Eight strains were identified with gene fusions to phoP-repressed genes. As shown in Table 6, the synthesis of most Prg::TnphoA fusion proteins was fully repressed by the pho-24 allele. While two loci had complete repression of fusion protein activity, others demonstrated only partial repression. The expression of pag in PhoP$^c$ strains is 5–10 fold less than that observed after bacteria are phagocytosed by macrophages suggesting that the degree of repression of some prg loci may be greater when pag are maximally activated within acidified macrophage phagosomes.

Lower values for prgB-phoA fusions in strains with a wildtype phoP locus (Table 7B) compared to PhoP$^-$ strains (Table 7) may represent some degree of repression in the presence of PhoP.

TABLE 6

| Allele | PhoP$^-$ | PhoP$^c$ | Fold Repression |
| --- | --- | --- | --- |
| prgA1::TnphoA | 29 | 7 | 4 |
| prgB1::TnphoA | 137 | 27 | 5 |
| prgB2::TnphoA | 77 | 19 | 4 |
| prgC1::TnphoA | 14 | 1 | 14 |
| prgE1::TnphoA | 21 | 5 | 4 |
| prgE2::TnphoA | 34 | 6 | 6 |
| prgE3::TnphoA | 25 | 6 | 4 |
| prgH1::TnphoA | 92 | 2 | 46 |

In Table 6, a comparison of the effect of phoP locus mutations on Prg-PhoA fusion protein activity is made. phoP$^-$ indicates that the strain assayed contains the phoP12 allele (CS030) and phoP$^c$ indicates the strain assayed contains the pho-24 allele (CS031). Values were calculated from stationary phase cultures. The numbers denote representative values of experiments performed on three separate occasions and represent activity in units of AP as defined above.

TABLE 7A

| Strain | Allele | Starvation Media | Rich Media |
| --- | --- | --- | --- |
| IB010 | prgB1::TnphoA | 21 | 26 |
| IB040 | prgH1::TnphoA | 7 | 181 |
| CS119 | pagC1::TnphoA | 1263 | 102 |

TABLE 7B

| Strain | Allele | Aerobic | Microaerophilic | Anaerobic |
| --- | --- | --- | --- | --- |
| IB010 | prgB1::TnphoA | 33 | 777 | 1521 |
| IB040 | prgH1::TnphoA | 142 | 85 | 41 |
| CS119 | pagC1::TnphoA | 431 | 173 | 81 |

TABLE 7C

| Strain | Allele | pH 4.5 | pH 7.0 |
| --- | --- | --- | --- |
| IB010 | prgB1::TnphoA | 332 | 26 |
| IB040 | prgH1::TnphoA | 8 | 18 |
| CS119 | pagC1::TnphoA | 145 | 27 |

Table 7 demonstrates the effects of environmental conditions on the in vitro regulation of prg loci.

Table 7A shows the effect of starvation on prg and pag expression. Starvation medium (N$^-$C$^-$P$^-$) (17) contained 0.04% glucose, 10 mM NH$_4$Cl, and 1 mM NaH$_2$PO$_4$.H$_2$O. The fusion protein activity for starvation media was measured after 48 hours of growth (OD$_{600}$=0.5) while that in rich media (LB) was measured in late-logarithmic growth (OD$_{600}$=1.0).* All cultures were grown aerobically.

Table 7B shows the effect of oxygen tension on expression of phoP-activated and phoP-repressed genes. Expression in rich medium is compared under aerobic conditions at stationary phase (OD$_{600}$>1.4), microaerophilic (OD$_{600}$=0.8), and strict anaerobic conditions with 80% N$_2$, 10% O$_2$, and 10% CO$_2$ (OD$_{600}$=0.6) after 24 hours of growth.* Table 7C shows the effect of pH on the expression of fusion protein activity of prg and pag loci. Expression was measured from cultures grown to logarithmic growth (OD$_{600}$=0.5) in LB media buffered to various pHs with sodium citrate. All the numbers represent activity in units of AP as defined above.

Chromosomal location of prg::TnphoA loci prg::TnphoA linkage analysis was performed to a bank of strains with randomly spaced Tn10Δ16Δ17 insertions to determine chromosomal locations and whether prg::TnphoA alleles were unlinked loci. The prg::TnphoA insertions were in five distinct linkage groups. Three alleles, prgE1-3::TnphoA were identically linked to the Tn10Δ16Δ17 insertion of AK3091(26%) and two other alleles, prgB1-2::TnphoA were similarly linked to the Tn10Δ16Δ17 insertion of AK3190 (94%), AK3249 (89%), and AK3186 (50%). Another allele, prgH1::TnphoA, was found to be 37% linked to the Tn10Δ16Δ17 insertion of strain AK3304. The other two prg alleles did not demonstrate linkage to the bank of strains tested. The chromosomal DNA of these two strains was analyzed by Southern hybridization analysis using a portion of TnphoA as a probe, and a rough physical map of the sites located adjacent to the TnphoA insertion was determined. These alleles, prgA and prgC, had different restriction endonuclease sites surrounding the TnphoA insertions. In addition, the repression of prgA and prgC fusion protein activity in strains with the pho-24 mutation was different; prgC was completely repressed, while prgA was only partially repressed indicating that these loci are different. Thus, five unlinked loci encoding envelope proteins repressed in the phoP$^c$ phenotype were identified.

Though three prg loci were identified that were linked to transposon insertions, none of the Tn10Δ16Δ17 insertions had a known map location. The physical map location of two of these transposon insertions, AK3249 and AK3304, was analyzed using XbaI restriction endonuclease digestion and pulse field gel electrophoresis (PFGE). Since Tn10Δ16Δ17 contains a single XbaI site, these Tn10Δ16Δ17 insertions can be assigned to a specific XbaI fragment of known map location (Liu et al., 1992, J. Bacteriol. 174:16622). AK3249 was assigned to 28–32 min, while AK3304 was assigned to either end of the 58–70 minute fragment. Further P22 transduction to known markers in those regions was performed. The Tn10Δ16Δ17 insertion of strain AK3249 and prgB1::TnphoA were found not to be linked to the Tn10 insertion of strain TN3061 (6% linked to dcp), which has a transposon insertion at 28 min, or to the ompD::Tn5 insertion of strain SH7782 at 32 min. prgH1::TnphoA was found to be very weakly linked to the srl202::Tn10 insertion of strain TT520 (<0.1%) at 59 minutes. These data indicate that prg are unlinked on the Salmonella chromosome, consistent with the function of phoP/phoQ as global regulators.

The chromosomal location of TnphoA insertions in phoP-repressed genes (prg::TnphoA) was determined by linkage analysis to a bank of strains with Tn10Δ16Δ17 insertions (Kukral et al., 1987, J. Bacteriol. 169:1787, herein incorporated by reference). Cells with TnphoA insertions were spread on LB agar plates containing 10 μg/ml tetracycline and 40 μg/ml XP. Then P22 lysates grown on strains with Tn10Δ16Δ17 insertions were spotted onto plates with a multiprong inoculator. After overnight inoculation, plates were reviewed for linkage by looking for mixed blue and white colonies. Linkage was confirmed and quantitated by carrying out individual transductional crosses between the Tn10Δ16Δ17 containing strains and the strain with the TnphoA insertion. After selection for the Tn10Δ16Δ17 encoded tetracycline resistance, strains were scored for loss of blue color and TnphoA encoded kanamycin resistance. Some TnphoA strains were found to be linked to Tn10Δ16Δ17 strains with no known map location. Two of these Tn10Δ16Δ17 insertions were physically mapped using PFGE following XbaI restriction endonuclease digestion. Based on physical mapping, linkage analysis to other transposon insertions by P22 bacteriophage transduction was determined as necessary.

Chromosomal DNA was prepared as described by Mekalanos, 1983, Cell 35:253, herein incorporated by reference, using Proteinase K instead of Pronase. Purification of plasmid DNA was performed by standard methods. Restriction endonuclease digestion was performed according to the recommendations of the manufacturer (New England Biolabs). DNA, size fractionated in agarose gels, was transferred to Genescreen Plus membranes (New England Nuclear/Dupont, Boston, Mass.) for blot hybridization by the method of Southern well known in the art. DNA probes were purified from agarose gels by the freeze-squeeze method (Tautz et al., 1983, Anal. Biochem. 132:14) and radiolabelled with [$^{32}$P]dCTP by the random primer method (Feinberg et al., 1983, Anal. Biochem. 132:6).

Cloning genes from Tnpho A fusions

The gene encoding prgH has been cloned using methods described below. The plasmid, pIB01, containing the prgH gene has been deposited with the American Type Culture Collection on Jul. 9, 1993 (Rockville, Md.) and has received ATCC designation ATCC 75496. FIG. 5 shows the partial DNA sequence of prgH (SEQ ID NO: 3). FIG. 9 shows the location and sequence of the entire prgH gene.

The genes described herein which have been identified by TnphoA insertion can be cloned using methods known in the art (Beattie et al., 1990, J. Bacteriol. 172:6997). Chromosomal For example, DNA of each strain containing a prg::T-nphoA gene fusion is digested with a restriction enzyme such as BamH1 which cuts at a single site in TnphoA maintaining the fusion junction, phoA sequences and the neo gene. Similarly, a plasmid such as pUC19 is digested with the same enzyme. Digested chromosomal and plasmid DNA are ligated overnight at 15° C. and transformed into competent E. coli. Transformations are plated on LB agar containing ampicillin and kanamycin to select for the bla gene of pUC19 and the neo gene of TnphoA. The chromosomal DNA containing the prg::TnphoA gene fusion can then be sequenced using standard methodology described above, such as the SEQUENASE (United States Biochemical) kit. Universal primer (United States Biochemical) corresponding to DNA sequences in the plasmid or TnphoA primer (5' -AATATCGCCCTGAGCA-3' ) (SEQ ID NO:4) corresponding to bases 71 to 86 of TnphoA can be used as primers.

To clone the wild type gene, a fragment of chromosomal DNA flanking TnphoA sequences can be used to screen a cosmid gene bank of wild type Salmonella strain ATCC 10428 using methods described above for cloning wild type pagC.

Environmental regulation of prg loci

Since phoP/phoQ are environmentally responsive regulators, the effects of different growth conditions on prg::TnphoA expression were tested. The growth rate of strains with prg::TnphoA insertions was comparable to wild-type organisms under all conditions. The expression of all prg loci was maximal in late logarithmic growth phase when bacteria were grown in rich (LB) media. An example of this is the comparison of values of prgH::TnphoA expression in Table 7A (rich media and stationary growth) and Table 7C (pH 7.0, log phase). Since the expression of pag loci was maximal in starvation (which only reaches a maximal $OD_{600}$=0.5) and stationary growth phase, this was consistent with a reciprocal relationship between the expression of pag and prg. Further analysis of prg loci expression under starvation conditions confirmed this reciprocal relationship (Table 7A). prgH expression was repressed (Table 7A) and other prg were minimally affected under starvation conditions, in contrast to the induction of pag expression when bacteria were starved (Table 7A).

Because of its role in bacterial-mediated endocytosis (BME), the effect of oxygen tension in rich medium on pag and prg expression was also tested (Table 7B). Different but not reciprocal regulation of pag and prg loci was found on growth at different oxygen tensions. Though pagA and pagB loci were minimally affected by growth at different oxygen tensions, the pagC virulence locus was approximately 5 fold repressed when bacteria were grown anaerobically as compared to aerobic growth (Table 7B). Variability was also noted in the expression of prg loci in response to growth conditions in the absence of oxygen. One loci, prgH, was repressed three-fold in anaerobic growth, while another locus, prgB, was induced almost 50-fold when grown anaerobically (Table 7B). Other prg loci had minimal change in fusion protein expression as a result of different oxygen tensions in the growth media.

Low pH conditions also had a variable effect on prg expression (Table 7C). The expression of pagC fusion protein activity was induced under acid conditions as previously known. When bacteria were grown to mid-logarithmic growth, no significant induction of the relative repression of prgH expression was noted in media of low pH, while prgB expression was induced on exposure of bacteria to low pH (Table 7C). Hence, loci maximally expressed under diverse environmental conditions can all be repressed by the PhoP$^c$ phenotype.

Acid sensitivity was tested by the method of Foster et. al., 1990, J. Bacteriol. 172:771, herein incorporated by reference. Strains were grown aerobically in E media and 0.4% glucose at 37° C. to an $OD_{600}$ of 0.5. The pH of the bacterial culture was decreased to near 3.3 by the addition of 1M hydrochloric acid. An aliquot was taken immediately ($t_o$), the remainder of the culture was incubated further at 37° C. with subsequent aliquots removed at 40 min ($t_{40}$) and 80 min ($t_{80}$) time points. The pH of the cultures remained near 3.3. The aliquots were diluted 1:10 in cold PBS, washed and resuspended in normal saline prior to plating serial dilutions for colony forming units.

prgH is a virulence locus for *S. typhimurium*

Since the PhoP$^c$ phenotype resulted in virulence attenuation and repressed the synthesis of approximately 20 proteins, the virulence of strains with single mutations in prg loci was tested (Table 8). Strains with prg::TnphoA insertions were screened for virulence defects by intraperitoneal injection of approximately 150 organisms into BALB/c mice. Controls were also performed with wild-type bacteria. A significantly longer time course of clinical disease progression was observed with a prg mutant strain compared to wild type bacteria. Mice injected intraperitoneally with strains containing the prgH1::TnphoA insertion developed clinical signs of typhoid fever, such as a "scruffy" phenotype (fever and piloerection) and hepatosplenomegaly in approximately 10–14 days, compared to approximately 24 hours for the wild type bacteria. Despite the extended time course of disease development, all the mice eventually died. Disease progression of mice injected with other strains containing prg::TnphoA insertions showed a similar pattern of illness to that of wild type bacteria.

TABLE 8

|  |  | $LD_{50}$ |
|---|---|---|
| Intraperitoneal injection | | |
| 14028s | Wild type | <10 |
| IB040 | prgH1 | $5.6 \times 10^1$ |
| CS015 | phoP-102 | $6.7 \times 10^5$ |
| IB041 | prgH phoP-102 | $1.2 \times 10^7$ |
| Oral inoculation | | |
| 14028s | Wild type | $6.5 \times 10^4$ |
| IB040 | prgH1 | $6.5 \times 10^5$ |

Table 8 shows the effect of the prgH1::TnphoA mutation on Salmonella mouse virulence. Strains were isogenic and administered by intraperitoneal injection and oral inoculation in 35 day old BALB/c mice. The number of animals used at bacterial dilutions near the $LD_{50}$ for each allele is listed in parentheses. The $LD_{50}$ determinations were repeated on three separate occasions.

Further testing of the $LD_{50}$ of strains containing prgH mutations was performed. prgH mutants were determined to have an $LD_{50}$ of approximately 60 organisms compared to a value of <10 for wild type bacteria. Due to the difficulty in accurately delivering organisms in small doses to mice, a strain with a mutation in both prgH and phoP was constructed. The PrgH$^-$PhoP$^-$ strain had greater than a 10 fold increase in $LD_{50}$ compared to CS015, an isogenic PhoP$^-$ strain (Table 8). The combined effect of the two mutations further documented that the prgH1::TnphoA mutation attenuated *S. typhimurium* virulence and indicated that mutations which affected two phases of phoP/phoQ regulated gene expression were additive in their effect on virulence. Strains with prgH1::TnphoA insertions were also tested for virulence when administered by the oral route. A 10 fold decrease in virulence (increase in $LD_{50}$) was observed (Table 8).

Further analysis of the efficiency of strains with prgH1::TnphoA insertions in crossing the mucosal barrier was tested by competition experiments with wild-type bacteria. During the first 72 hours after oral inoculation with mutant bacteria, no prgH1::TnphoA mutants were recovered from the bloodstream of mice compared to control experiments in which organisms were routinely isolated from the blood of mice inoculated with wild type bacteria. Other strains with prg mutations were also tested for virulence defects by the oral route, but no significant change in virulence was observed.

Mouse virulence studies were carried out as follows. Bacteria were grown aerobically at 37°0C. to stationary phase, washed with LB, and diluted in normal saline. 35 days old (16–18 g) female BALB/c mice were purchased from the Charles River Breeding Laboratories, Inc. (Wilmington, Mass.). Diluted bacterial samples in saline were injected intraperitoneally with an inoculum of 0.1–0.15 ml. Bacteria were administered orally as a 0.5 ml bolus to mice fasted for 2 hours, via a 2 inch straight, 18 gauge stainless steel animal oral feeding needle (Harvard Apparatus, Inc., South Natick, Mass.) under mild 2-bromo-2-chloro-1,1,1-trifluoroethane (Halothane) anesthesia. The number of organisms administered was quantitated by plating for cfu/ml on LB agar. Mouse 50% lethal dose ($LD_{50}$) values were determined by standard methods (Reed and Muench, 1938, Amer. J. Hygiene 27:493). The $LD_{50}$ determinations were repeated on three separate occasions. Competition assays were performed after bacteria were administered orally to mice as above. Bacteremia was assessed on days 1–4 from tail bleeds or intracardiac punctures with 50 $\mu$l of blood plated immediately and after growth in LB broth at 37° C. overnight. Spleen and intestinal harvests were performed on days 1–6 with organs homogenized in 3 mls of 0.9% sodium chloride. Samples and cultures were plated in serial dilutions. *S. typhimurium* was confirmed by characteristic growth (black colonies) on Hektoen-enteric agar (Difco Laboratories) and by the macroscopic slide agglutination test with Salmonella rabbit serum Group B (Antigens 4, 5, 12) (Fisher Scientific).

Mutations in oxygen-induced genes do not affect mouse virulence

Both prgH and pagC loci were shown to be repressed by anaerobic growth and required for full virulence, thus suggesting that a shift from anaerobic to aerobic conditions might serve as a general signal for induction of virulence genes. Strains with mutations in oxygen-inducible loci (Aliabadi et al., 1986, J. Bacteriol. 165:780) were constructed. ATCC14028s derivatives with oxiA, oxiC, and oxiE mutations were made (termed CS032, CS033, CS034, respectively). These strains were as virulent as wild type bacteria. Though these gene fusions could still mark operons containing virulence genes, this data suggests that these loci are not essential to full virulence and that oxygen induction is not always correlated with virulence function.

prgH mutants have normal survival within macrophages

Since the PhoP$^c$ phenotype resulted in a defect in bacterial survival within macrophages, the effect of this mutation on the synthesis of a prgH-encoded protein was tested. A strain with the prgH1::TnphoA insertion was tested for intracellular survival within bone marrow-derived macrophages from BALB/c mice and J774.2 cells, a macrophage derived cell line. No defect in intracellular survival was observed. A strain with a prgB1::TnphoA insertion was also tested and found not to have a defect in survival within macrophages.

Assays to determine bacterial survival within macrophages were performed as described by Buchmeier al., 1989, Infect. Immun. 57:1, herein incorporated by reference. Bacteria grown to stationary-phase were opsonized for 30 minutes in normal mouse serum before exposure to cultured bone marrow-derived macrophages harvested from BALB/c mice. One hour after infection, gentamicin 10 μg/ml was added to kill extracellular bacteria. All time points (1, 4, and 24 hr) were done in triplicate and repeated on three separate occasions.

Cultured bone marrow macrophages were harvested from BALB/c mice purchased from the Charles River Breeding Laboratories. J774.2 macrophages were cultured in Dulbecco's minimal essential medium with 10% fetal bovine serum (DMEM/10% FBS).

prg::TnphoA insertions do not suppress the phenotypes of PhoP mutants

Several phenotypes of phoP mutants, including defensin and acid sensitivity as well as mouse virulence attenuation, were tested for suppression on addition of a prg::TnphoA mutation. To test the ability of a phoP mutation to suppress the synthesis of prg products, phoP mutant strains isogenic except for prg::TnphoA mutations were constructed and tested for mouse virulence, where suppression would involve an increase in virulence, or decreased acid and defensin sensitivity. prg::TnphoA insertions had no effect on the virulence phenotypes of PhoP⁻ bacteria. These results indicate that the prg::TnphoA mutations tested did not suppress the PhoP null phenotype as single mutations.

prgH and phoP^c mutants are defective in bacterial-mediated endocytosis by cultured epithelial cells The BME of prg::TnphoA and phoP^c S. typhimurium strains was tested. The following observations (described herein) suggested that prg genes may be involved in bacterial-mediated uptake by eucaryotic cells: prgH1::TnphoA was shown to be located at 59' on the bacterial chromosome, a location where other genes essential to invasion are clustered; prgH mutants were shown to be defective in competition with wild type organisms on reaching the bloodstream of mice in the first 72 hours after oral ingestion; and the expression of one prg locus, prgB, was dramatically induced under anaerobic growth conditions. Strains with prgH and pho-24 mutations had a significant reduction (p-value<0.01) in their ability to induce uptake by Madin-Darby canine kidney (MDCK) polarized epithelial cells compared to wild-type bacteria. Other prg strains with TnphoA insertions did not demonstrate a statistically significant defect in BME by epithelial cells (Table 9). The adherence of strains defective in BME was unaffected by the prgH::TnphoA insertion when determined by cell-associated cfu/ml before the administration of gentamicin (Table 9) and by microscopy.

To assay bacterial adherence and uptake of bacteria by epithelial cells, bacterial strains were grown at 37° C. without shaking (microaerophilic) to a final density of approximately 2×10⁸ colony forming units (cfu)/ml. Assays were performed by seeding 10⁵ MDCK cells/well in 24-multiwell tissue culture plates. Cells were incubated overnight at 37° C in 5% CO₂/95% air atmosphere in DMEM/10% FBS without antibiotics until >80% confluent. The adherence and invasion assays were carried out according to the protocol of Lee and Falkow, 1990, Proc. Natl. Acad. Sci. USA 87:4304, herein incorporated by reference.

TABLE 9

| Strain | Genotype | Adherence | Invasion |
|--------|----------|-----------|----------|
| 14028s | Wild type | 4.2% | 3.8% |
| SM7 | Str^r smb | — | 0.6%* |
| CS119 | pagC1::TnphoA | — | 1.9% |
| IB005 | prgA1::TnphoA | — | 7.6% |
| IB010 | prgB1::TnphoA | — | 2.9% |
| IB020 | prgC1::TnphoA | — | 1.5% |
| IB025 | prgE1::TnphoA | — | 1.9% |
| IB040 | prgH1::TnphoA | 5.7% | 0.1%* |
| CS022 | pho-24 | 1.9% | 0.06%* |
| IB043 | pWKSH5 in IB040 | — | 17.5%* |
| IB044 | pWKSH5 in CS022 | — | 0.09%* |

In Table 9, the effect of prg::TnphoA insertions on Salmonella-mediated endocytosis by MDCK epithelial cells is shown. Microaerophilically grown bacterial strains were assessed for changes in adherence and invasion. Adherence was determined as the percentage of bacteria adhered to the cells after centrifugation and 30 minute 4° C. incubation/ total number of bacteria added to each well. Invasion was determined as the percentage of bacteria that had invaded after a two hour incubation with gentamicin/total number of bacteria added to each well. There was no difference between S. typhimurium wildtype and S. enteritidis CDC5 wildtype strains with respect to adherence and invasion frequency. The asterisk (*) represents statistical significance by variance analysis of the invasion data done in triplicate compared to wild-type (p-value <0.01 ).

The confluent MDCK monolayers were washed three times with PBS, then 0.9 ml of cold DMEM/10% FBS was added to each well. Bacteria were washed in LB and resuspended in an equivalent volume of DMEM/10% FBS. Approximately 5×10⁷ bacteria were added/well. The plates were spun at 500 rpm at 4° C. for 10 minutes, then incubated at 4° C. for 30 minutes. Adherent bacteria were recovered by washing the plates three times with phosphate-buffered saline (PBS), lysing the epithelial cells in 0.5 ml of 1% Triton-X-100/PBS, and plating for cfu/ml on LB agar. A morphologic assessment of adherence was also performed by staining bacterially infected epithelial cell monolayers grown overnight on coverslips for 7 minutes in 1 μg/ml 4' 6-diamidino-2-phenylindole (DAPI). These DAPI stained coverslips were examined by both fluorescent and phase contrast microscopy using a Leitz Laborlux 12 microscope.

Invasion or bacterial-mediated endocytosis (BME) was assessed by allowing bacteria to adhere as described above. Plates containing bacteria and epithelial cells were incubated for two hours at 37° C. in a 5% CO₂/95% air atmosphere. Each well was washed three times with PBS to remove bacteria not associated with cells. DMEM/10% FBS supplemented with 10 μg/ml gentamicin was then added to kill extracellular bacteria. After 90 minutes of incubation, the cell monolayers were washed three times with PBS and the viable intracellular bacteria were released by vigorously pipetting with 0.5 ml of 1% Triton X-100/PBS. An invasion deficient Salmonella enteritidis mutant and an invasive clinical wild-type isolate of S. enteritidis were used as controls for BME. Viable bacteria were quantitated by plating for cfu/ml on LB agar medium. All assays were done in triplicate and repeated at least three times.

MDCK epithelial cells were used between passage 40–58 to maximize bacterial adherence and invasion. Epithelial cell lines were cultured in DMEM/10% FBS and 1% penicillin/streptomycin solution at 37° C. in a 5% CO₂ atmosphere.

To assay bacterial defensin sensitivity, NP-1 defensin was purified from rabbit peritoneal neutrophils according to methods known in the art (Selsted et al., 1985, J. Biol. Chem. 260:4579; Selsted et al., 1984, Infect. Immun. 45:655). Typically, $10^5$ bacteria in 0.5% tryptone in 100 μl volume were exposed to 50–100 μg of defensin/ml at 37° C. for 2 hours. The reactions were stopped by diluting the reaction in 0.9% NaCl. Appropriate dilutions were plated to determine the cfu/ml of surviving bacteria. Assays were performed in duplicate at least twice for each strain. Appropriate assays with sensitive (PhoP$^-$) and resistant (wild-type) strains were performed as controls.

Mapping of prgH

The location of prgH relative to other invasion loci at 59 minutes was determined using linkage analysis. P22 transduction linkage analysis indicated that the Tn10Δ16Δ17 of strain AK3304 had similar linkage to invA (40%) and prgH (37%); however, invA was not linked to sorbital. The prgH1::TnphoA insertion was found to be linked (99.6%) to the transposon insertion of EE517, a strain with a 8.5 kilobase deletion adjacent to the Tn5B50-378 insertion of hil.

Figure 4:
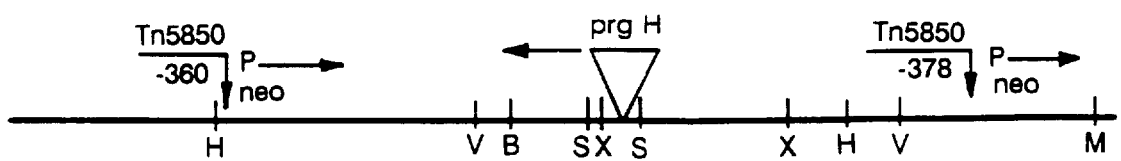

A physical map of the restriction endonuclease sites surrounding the TnphoA insertion of strain IB037 was made (FIG. 4) revealing no similarities to the known restriction endonuclease map of the invA-E region. Plasmids containing the cloned inv and hil DNA were then used as probes in Southern hybridization analysis of chromosomal DNA from wild type ATCC10428s and IB040 bacteria containing the prgH1::TnphoA insertion. When a plasmid which contains other invasion loci highly linked to invA-E (invH, invF, and part of invG) was used as a probe, no differences in hybridization pattern was found between wild type bacteria and strain IB040 indicating that prgH was not located within the inv region. However, when a plasmid containing a 5 kb region immediately downstream of the Tn5B50-380 insertion of hil was used as a probe, the prgH1::TnphoA insertion was demonstrated to be located within this region. By use of the known restriction map of the hil locus (Lee et al., 1992, Proc. Natl. Acad. Sci. USA 89:1847) and the known restriction endonuclease sites of TnphoA, the physical map of this area and the relationship of prgH1::TnphoA within it were further defined (FIG. 4). The prgH1::TnphoA insertion was oriented so that the direction of transcription of the phoA fusion protein was opposite to that of the Tn5B50 insertions that confer the hil phenotype and contain a constitutive neomycin promoter that is transcribed out of the transposon (FIG. 4). Although prgH was found to be located within the hil locus, this gene is unique in that it is oppositely transcribed and unlike any other genes identified within the hil locus, prgH is regulated by the phoP regulon.

Since it was possible that a protein whose expression was altered by the Tn5B50-380 insertion might alter the expression of prgH, strains containing both insertions were constructed and the PrgH-PhoA fusion protein activity compared under different environmental conditions. When bacteria were starved or grown anaerobically, derepression of fusion protein activity was observed. Table 11 shows the effect of the Tn5B50-380 insertion on expression of PrgH fusion protein activity.

TABLE 11

| Strain | Allele | Starvation | LB (aerobic) | LB (anaerobic) |
|---|---|---|---|---|
| IB040 | prgH1::TnphoA | 5 | 142 | 41 |
| IB042 | Tn5B50-380 prgH1::TnphoA | 46 | 248 | 227 |

This data demonstrates that the Tn 5B50–380 insertion increased prgH expression, even though prgH transcription was opposite to that of the Tn5B50-380 encoded neomycin promoter. Starvation (repressing conditions for prg) indicates that bacteria were grown aerobically for 48 hours in starvation medium (N$^-$C$^-$P$^-$) containing 0.04% glucose, 10 mM NH$_4$Cl, and 1 mM NaH$_2$PO$_4$.H$_2$O. LB (aerobic) indicates that bacteria were grown in Luria-Bertani broth (rich media) to late logarithmic growth (nonrepressing conditions) (OD$_{600}$>1.0 ). LB (anaerobic) indicates that bacteria were grown under strict anaerobic conditions for 24 hours (OD$_{600}$=0.6). All the numbers represent activity in units of AP as described above.

To rule out the possibility that the BME defect of the prgH mutant was an artifact of the PhoA fusion protein produced, complementation analysis was performed with a plasmid (pWKSH5) containing a 5.1 kb HindIII fragment which included the hil and prgH loci. The plasmid was crossed into prgH (IB040) and phoP$^c$ (CS022) mutant bacteria to create strains IB043 and IB044, respectively. The BME phenotype of the prgH mutant was similar to wild-type with the same plasmid insertion. The BME phenotype of the phoP$^c$ mutant was not complemented by this plasmid. These results indicate that a gene product altered in synthesis as a result of the prgH::TnphoA insertion was necessary for BME.

Using a strain with a phoP/phoQ locus mutation that constitutively simulates the environmental activation of pag (phenotype PhoP$^c$ ), five unique phoP-repressed loci encoding envelope proteins were defined. phoP-repressed genes (prg) were found to be widely spaced on the chromosome and the expression of prg loci was repressed under starvation conditions, when pag loci were induced (Table 10).

TABLE 10

| Environment | pag | prg |
|---|---|---|
| media | starvation | rich |
| O$_2$ | aerobic - pagC | aerobic -prgH anaerobic - prgBpH |
| 3.3–5.5 | 3.3–5.5 - prgB | >6.0 - prgH |
| mammalian cell | macrophage | epithelial |

PrgH was shown to lie between two Tn5B50 insertions that confer the Hil phenotype. Since deletion mutants in this region have been demonstrated to also have defects of BME, and the BME defect of prgH mutants can be complemented with a plasmid containing this locus, it is possible that a protein not synthesized as a result of the prgH1::TnphoA insertion promotes BME (FIG. 4).

Contrary to the expectation that genes essential to the Hil phenotype would be induced under microaerophilic conditions similar to what was found for prgB, prgH expression was maximal during aerobic growth and the Tn5B50-380 insertion, which results in a Hil phenotype, derepressed expression of prgH. In addition, the direction of transcription predicted by the prgH1::TnphoA insertion is opposite to that of the Tn5B50-380 encoded neomycin promoter associated with the Hil phenotype suggesting that a regulatory protein interrupted by or transcribed from the Tn5B50-380 insertion affects the expression of prgH.

In view of the observation that pWKSH5, a plasmid containing prgH (hil), did not complement PhoP$^c$ bacteria for BME, it is possible that other invasion genes may also be regulated by phoP/phoQ. If prgH was expressed from pWKSH5, despite the presence of the pho-24 mutation, this suggest that other genes repressed as part of the phoP$^c$ phenotype are necessary for BME.

The identification and characterization of prgH has shown that PhoP/PhoQ oppositely regulate factors necessary for bacteria to enter or to survive within mammalian cells, further documenting the importance of gene regulation to bacterial virulence. The identification of prg loci can be used to study the regulation of bacterial genes after infection of mammalian cells. Understanding the regulation of virulence genes, such as prgH can also be used to attenuated pathogenic bacteria for the development of new live vaccines for typhoid fever.

Role of prg genes in virulence

The prg locus, prgH, was found to contribute to mouse virulence when S. typhimurium was administered by both the oral and intraperitoneal routes. prgH as well as phoP$^c$ mutants were further found to be defective in bacterial-mediated uptake by epithelial cells suggesting that an inability to cross epithelial barriers might contribute to the attenuation of virulence observed. Competition studies in mice after oral ingestion of bacteria further supported that prgH mutants were defective in transcytosis across the intestinal epithelial barrier. Therefore, at least two phases of PhoP/PhoQ regulated protein expression essential to bacterial virulence have been defined. In one phase, prg expression promotes bacterial mediated endocytosis by epithelial cells (Table 10), while in another phase, pag expression promotes survival within macrophages.

Systemic pathogens, such as Salmonella, may encounter more complex and varied environments than may be encountered by mucosal pathogens. The achievement of intermediate states of pag and prg expression could be essential to virulence at some stage of the infectious cycle. Consistent with this concept was the lack of uniformity observed in the expression of pag and prg on growth at different oxygen tensions and pH conditions. These data may also indicate that not all regulation of pag and prg is mediated directly through PhoP and PhoQ. Given the function of PhoP as a transcriptional regulator, it is likely that prg loci repression occurs at the level of transcription.

The approach of defining genes repressed by the pho-24 mutation has led to the discovery of at least one virulence locus, prgH, which can be mutated to attenuate the bacteria for vaccine purposes.

Attenuation of Bacterial Virulence by Constitutive Expression of Two-component Regulatory Systems The virulence of a bacterium can be attenuated by inducing a mutation which results in the constitutive expression of genes under the control of a two-component regulatory system or by inducing a mutation that inactivates a gene under the control of the two-component systems. A balance between the expression of the genes under the control of the two-component system, e.g., between pag and prg gene expression, and possibly between two-component system regulated genes and other genes, is necessary for full virulence. Mutations that disrupt this balance, e.g., mutations that cause the constitutive expression of a gene under the control of the two-component system, or a mutation that inactivates a gene under the control of the two-component system, e.g., the pag gene, reduce virulence.

Constitutive mutations in two-component regulators can be identified by the use of a strain containing a recorder gene fusion to a gene regulated by the two-component system. Such gene fusions would most typically include DNA encoding the lacZ gene or AP fused to a gene under the control of the two-component system. Strains containing fusions that are (as compared to wild type or parental strains) highly expressed in an unregulated fashion, i.e., constitutive, can be detected by increased color on chromogenic substrates for the enzymes. To detect constitutive mutations a cloned virulence regulator could be mutagenized e.g., by passage through an E. coli strain defective in DNA repair or by chemical mutagenesis. The mutated DNA for the regulator would then be transferred to the strain containing the gene fusion and constitutive mutations identified by the high gene fusion expression (blue color in the case of a lacZ fusion grown on media containing X-gal). Constitutive mutations in a component of a two-component regulatory system could also be made by in vitro mutagenesis after other constitutive mutations have been sequenced and a specific amino acid change responsible for the constitutive phenotype identified. Putting several amino acid changes that all result in a PhoP constitutive phenotype would result in a decreased frequency of reversion by spontaneous base changes. A constitutive mutation could also be constructed by deletion of the portion of the amino terminus of the phospho-accepting regulator which contains the phosphoacceptor domain e.g., deletion of sequences encoding amino acids amino terminal to amino acid 119 in the phoP gene or deletion of analogous phospho accepting sequences in genes of other two-component regulatory systems. This could result in a conformational change similar to that induced by phosphorylation and result in increased DNA binding and transcriptional activation.

Attenuation of virulence: deletion in the phoP/phoQ regulon

As discussed above, the PhoP regulon is essential to full virulence of Salmonella. This regulon is composed of two genes, phoP and phoQ located in an operon, and over 40 genes they positively and negatively regulate (pag and prg, respectively).

phoP null S. typhimurium mutants have been demonstrated to be markedly attenuated and also effective vaccine strains when studied in the BALB/c mouse model of typhoid fever. This phenotype is likely the result of multiple, phoP-activated virulence genes, as transposon insertions in multiple different phoP-activated genes have been independently demonstrated to decrease S. typhimurium virulence. S. typhimurium mutants deleted for genes essential to aromatic amino acids (aroA null or aroC/aroD null mutants) are also markedly attenuated in the mouse model. However, testing of aroC/aroD mutants in humans has shown that although these strains are immunogenic, bacteremias and side effects such as fever have been noted at doses as low as $10^5$ to $10^7$ organisms administered as a single oral dose (Hone et al., J. Clin. Invest. 90:412–420).

It has now been found that a large deletion in a global regulator of Salmonella virulence, i.e., the phoP/phoQ operon, significantly decreases the virulence of the bacteria. This mutation, the result of a 1 kB deletion of DNA within the phoP/phoQ locus, was initially made in S. typhimurium and subsequently transferred via homologous recombination to *S. typhi*. In order to confer an even greater margin of safety in construction of this vaccine, it was created in a strain background deleted for genes essential to aromatic amino acids and carrying the histidine G46 mutation, a mutation rendering the organism auxotrophic for histidine. The resulting strain, *S. typhi* TyLH445, offers several advantages over existing vaccine candidates, most notably, immunogenicity without transient bactermia.

Use

The Salmonella cells of the invention are useful as sources of immunological protection against diseases, e.g., typhoid fever and related diseases, in an animal, e.g., a mammal, e.g., a human, in particular as the basis of a live-cell vaccine capable of colonizing the inoculated animal's intestine and provoking a strong immune reaction. Appropriate dosages and conditions of administration of such a live, attenuated vaccine are known in the art, e.g., as described in Holem et al., *Acute Enteric Infections in Children, New Prospects for Treatment and Prevention*, (1981) Elsevier/North-Holland biomedical Press, Ch. 26, pp. 443 et seq. (Levine et al.), hereby incorporated by reference, and are described in the examples below.

Advantages

One advantage of the invention is that the bacterial cells are attenuated as a result of a mutation(s), i.e., the phoP/phoQ operon, that directly affect a virulence pathway. Another advantage is that the bacterial cells have mutations in two completely different attenuating genes, i.e., the aromatic amino acid synthesis pathway (aro), and in an operon important to *Salmonella virulence* (phoP/Q). As a result, the bacteria appear to be extremely attenuated; doses as high as $1\times10^9$ cfu appear to be very safe. Other vaccines under development, such as CVD 908, have caused some systemic symptoms, e.g., fever or bacteremia, at doses as low as $1\times10^7$ cfu.

In addition to the phoP/phoQ deletion and the AroA- mutation, the bacterial cells of the invention may also contain a histidine mutation to further alternate virulence, although absence of the histidine mutation may improve immunogenicity. The bacterial cells of the invention are the most promising vaccine candidates to date because they are strongly immunogenic and safe, i.e., extremely attenuated.

Construction of vaccine strain

The bacterial cells of the invention were made by deleting approximately 1 kb of DNA in the phoP/phoQ regulon.

PhoP/phoQ deleted suicide vectors were constructed using methods known in the art. A DNA fragment containing the phoP/phoQ locus was obtained by PCR using wild type *S. typhimurium* chromosomal DNA as a template. PCR primers flanking the phoP/phoQ locus were engineered to contain terminal restriction enzyme recognition sites, e.g., recognition site for EcoRI, to facilitate subsequent cloning. Following amplification, the PCR product was digested with EcoRI and cloned into the EcoRI site in the polylinker of a high copy vector. The plasmid containing the phoP/phoQ DNA fragment was named pLH356.

Sequence analysis and restriction mapping of the phoP/phoQ locus revealed four HpaI sites within the locus; no HpaI sites were found in the vector. To create an internal deletion within the phoP/phoQ locus, pLH356 DNA was cut to completion with HpaI, and religated, to yield with an internal deletion from nucleotides 376–1322 (pLH418). This deletion was confirmed by restriction digestion of the plasmid.

A DNA fragment containing the internally deleted phoP/phoQ locus was excised from pLH418 using the SacI/SphI restriction sites within the polylinker region of the vector. This fragment was cloned into compatible sites in the plasmid CVD442, which carries the sacB gene to allow positive selection for allelic exchange. The resulting suicide vector was called pLH423.

pLH423 was transformed into *E. coli* lambda pir SY327, and subsequently into *E. coli* lambda pir SM10 (strain LH425). *E. coli* strain LH425 was mated with *S. typhimurium* strain CS019. Single recombinants carrying plasmid sequences integrated onto the *S. typhimurium* chromosome were selected by plating on agar containing ampicillin and chloramphenicol (Strain LH428). These strains were confirmed to be ampicillin resistant and sucrose sensitive, i.e., death on 20% sucrose plates containing no NaCl when incubated at 30° C. These data confirm the integration of plasmid sequences into the Salmonella chromosome.

A P22 bacteriophage lysate was made from strain LH428; phage particles were concentrated 20× by high speed centrifugation and transduced into *S. typhi* strain 522Ty2 (a strain with a deletion in the aroA gene, and the G646 mutation which renders the organism auxotrophic for histidine). Single recombinant *S. typhi* organisms were selected by plating on LB plates supplemented with aromatic amino acids, cystine, histidine, and ampicillin (strain LH453).

Strain LH453 was grown with aromatic amino acids, cystine, and histidine (but without ampicillin) to mid logarithmic growth phase. Serial dilutions were plated on LB 20% sucrose plates lacking NaCl, and on LB plates lacking NaCl. The number of bacteria that grew on plates without sucrose was greater than the number that grew on sucrose-supplemented plates by a factor of three logs. These data suggest that many colonies lost plasmid sequences containing the sacB gene.

Multiple colonies from the sucrose selection were picked and confirmed to be ampicillin sensitive and sucrose resistant. Chromosomal DNA from approximately 10 colonies was purified and subjected to Southern blot analysis, utilizing the 2.3 kb fragment of wild type phoP/phoQ as a probe.

Southern blotting revealed the loss of two HpaI sites and an XmnI site known to be within the 1 kb deleted fragment of phoP/phoQ in several strains. One of these strains was designated TyLH445.

In vitro evaluation of TyLH445

TyLH445 was extensively characterized in vitro using standard clinical microbiological tests. The nutritional requirements of TyLH445 were evaluated. TyLH445 did not grow on M-9 plates unless supplemented with aromatic amino acid mix, cystine (*S. typhi* grows better with cystine), and histidine. These data confirmed that TyLH445 was AroA-, His-.

TyLH445 was found to agglutinate with polyclonal serum against Salmonella and polyclonal serum against *S. typhi* Vi antigen. Group D agglutination was found to be variable, perhaps due to excess Vi antigen. TyLH445 was also found to be indole negative (as are all Salmonellae), and to produce very little hydrogen sulfide (as do many *S. typhi*). Biochemical testing utilizing both the VITEK system as well as the BBL Crystal Enteric organism identification system was also carried out. These data indicated that the TyLH445 strain was *S. typhi*.

Figure 10:
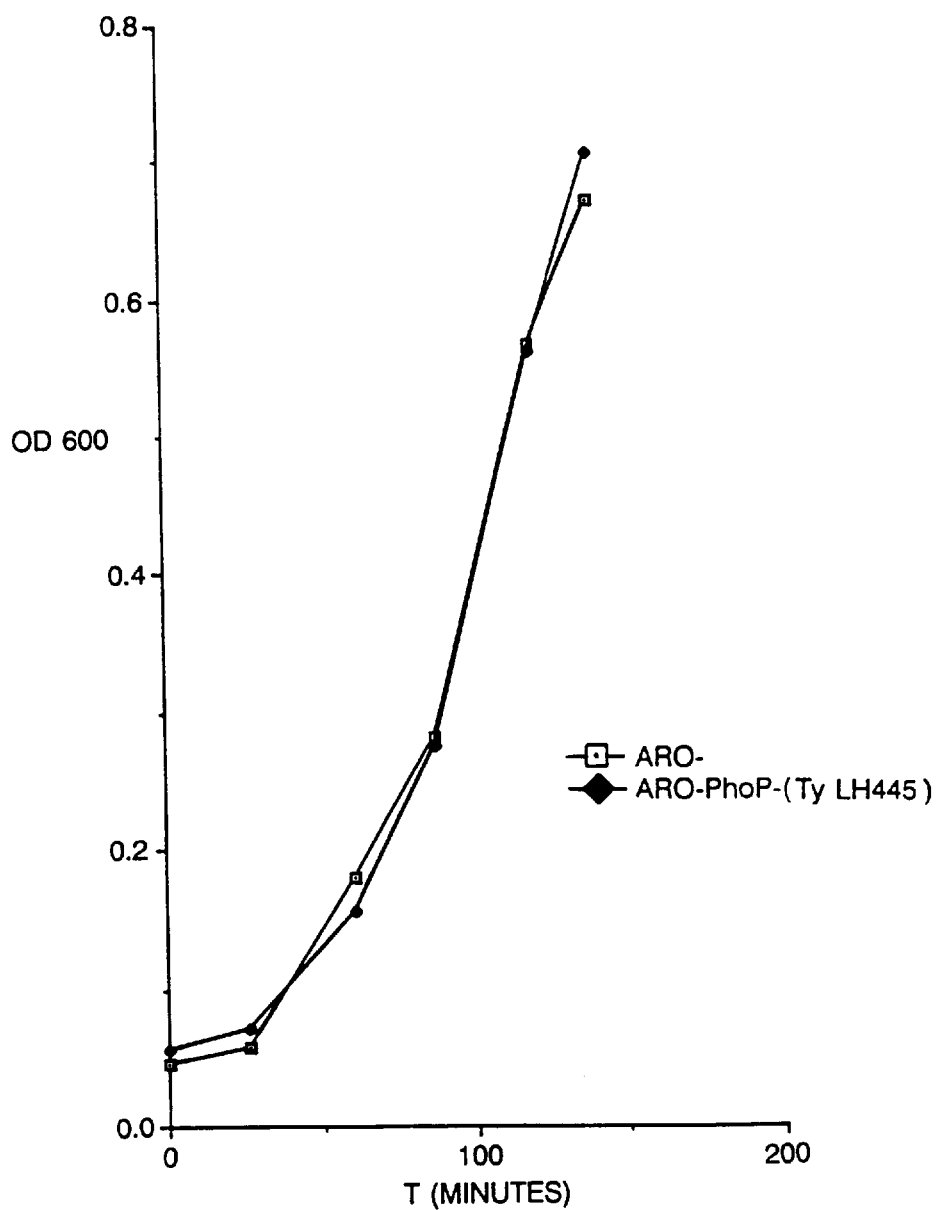
FIG. 10 is a line graph showing the growth rates of the parent Salmonella strain (AroA⁻) and the vaccine strain (AroA⁻, PhoP⁻).
Figure 11:
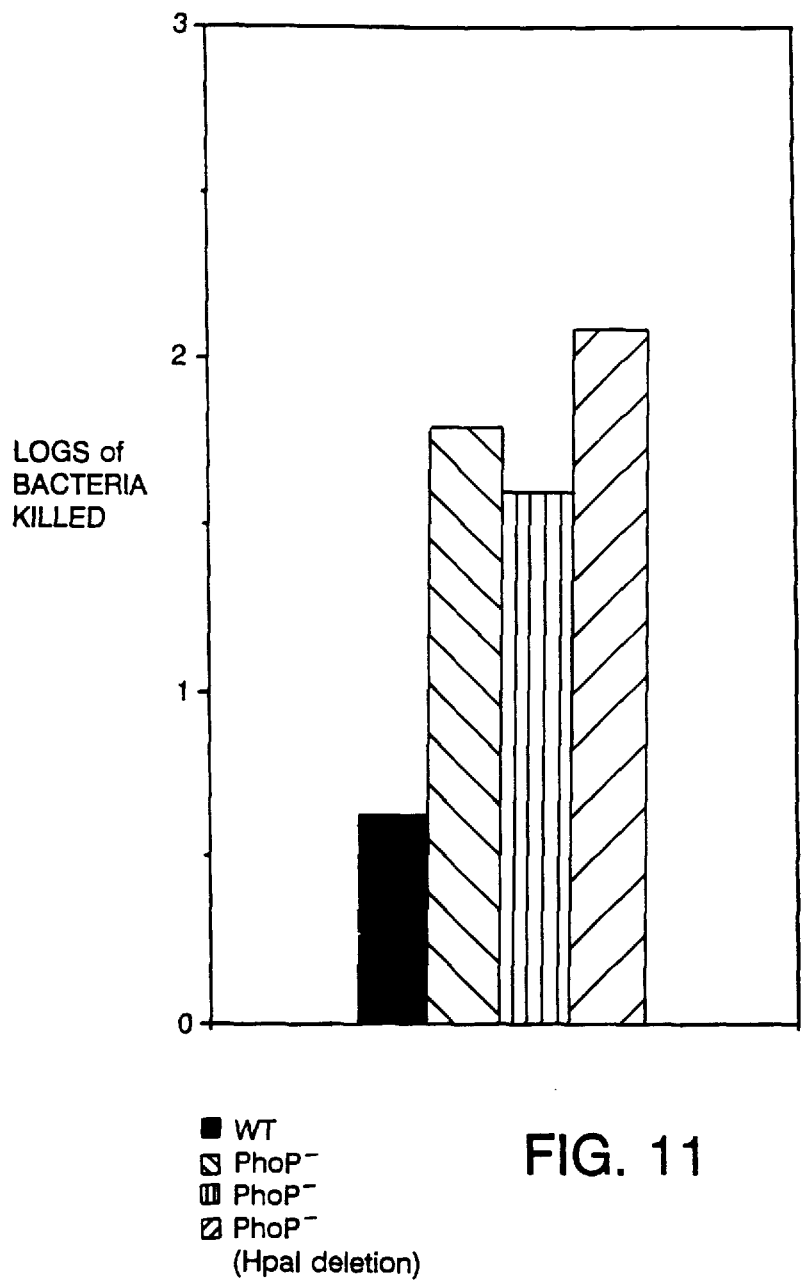
FIG. 11 is a bar graph showing defensin sensitivity of mouse vaccine strains (S. typhimurium).
Figure 12:
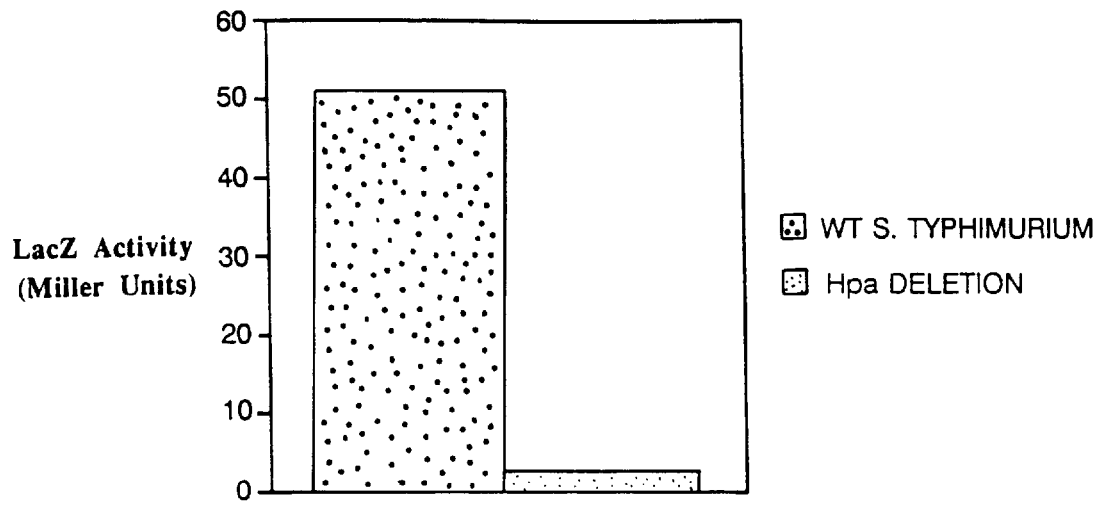
FIG. 12 is a bar graph showing phoP activation as measured by LacZ activity using the pagB:lacZ recorder fusion construct.
Figure 13:
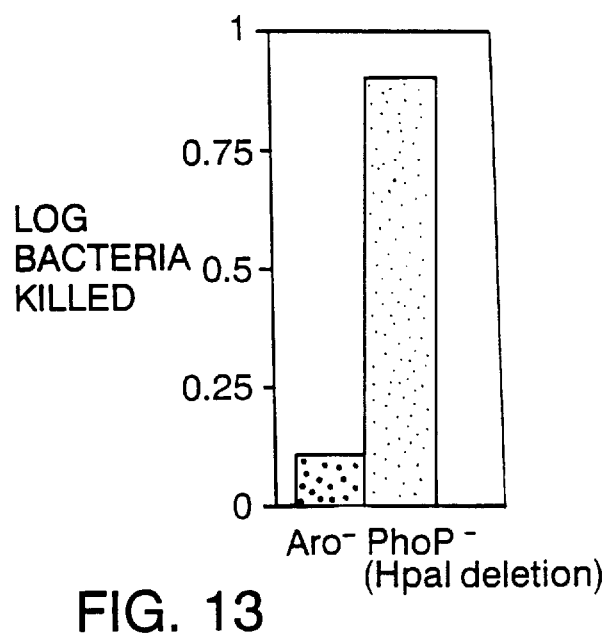
FIG. 13 is a bar graph showing defensin sensitivity of S. typhi vaccine strain TyLH445 compared to the AroA⁻ parent strain.
Figure 14C:
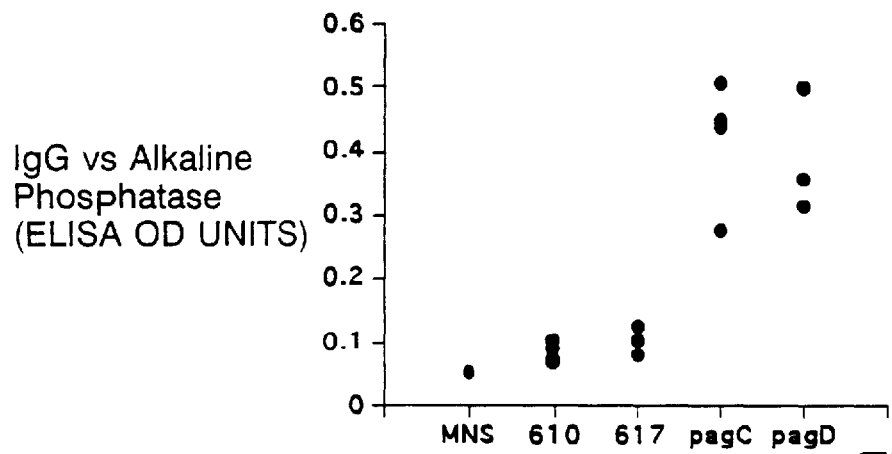
FIG. 14C is a graph showing the immune response to the model heterologous antigen, AP.
Figure 14B:
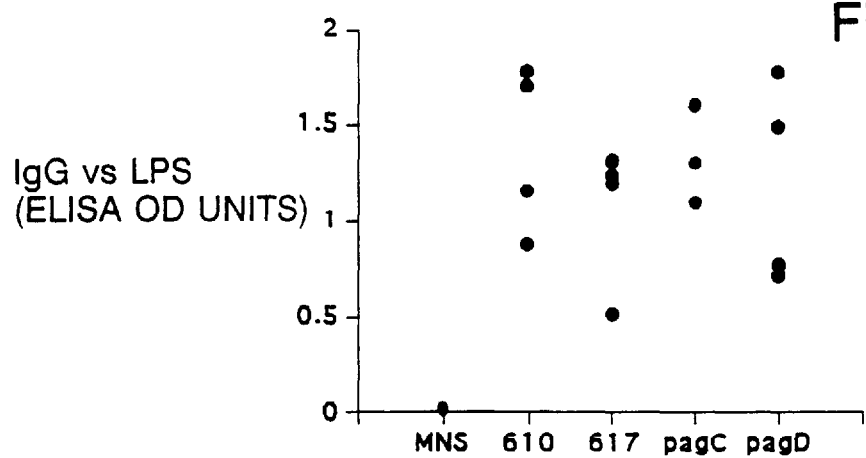
FIG. 14B is a graph showing the immune response to lipopolysaccharide (LPS).
Figure 14A:
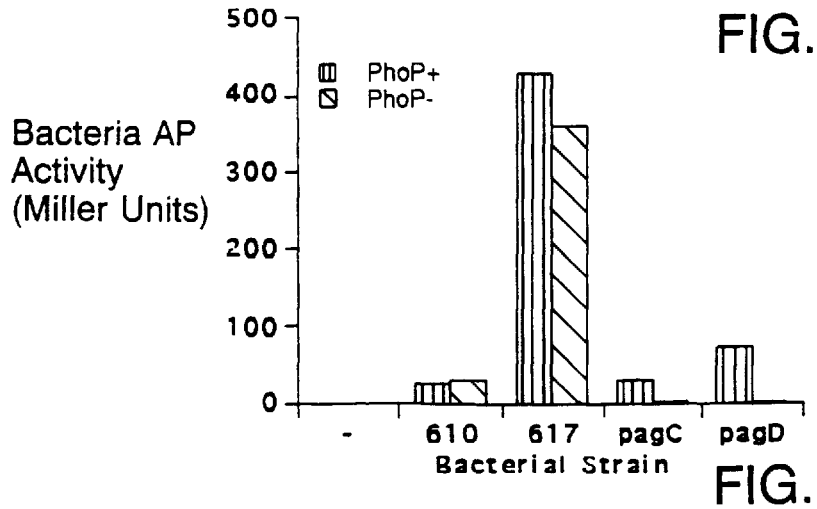
FIG. 14A is a graph showing the relative expression of constitutive expression (610 and 617) and phoP regulated (PagC and pagD) expression of AP fusion proteins.

Growth characteristics of TyLH445 were also evaluated. TyLH445 was found to grow just as quickly as its parent, 522Ty2, (phoP/phoQ locus intact). Growth in vitro was measured in aromatic amino acid/histidine/cystine-supplemented Luria broth at 37° C. Growth curves of the parent and vaccine strain were found to be essentially identical (see FIG. 10).

Standardized clinical testing methods were use to determine antibiotic sensitivity. TyLH445 and the parent strain, 522Ty2, were found to be sensitive to ampicillin, trimethoprim-sulfamethoxazole, ciprofloxacin, aminoglycosides, and third generation cephalosporins. No difference in zone sizes was detected between the parent and vaccine strains, suggesting that no other antibiotic resistance mechanisms, e.g., modification of antibiotic transport systems, or modification of the cell wall of the bacterium, were affected by introduction of the mutated phoP/phoQ locus into *S. typhi*.

The phoP/phoQ HpaI deletion mutants were tested for defensin sensitivity, a phenotype of phoP null mutants. Defensin sensitivity assays were performed as follows.

Liquid cultures of strains to be tested were grown overnight. Cultures were then diluted 1:200, and grown to an optical density ($OD_{600}$) of approximately 0.2, after which the cells were diluted to concentration of approximately $1\times10^5$ organisms per 0.05 ml.

Two reactions were carried out for each strain: (1) vehicle alone (0.01% acetic acid in sterile water) and (2) defensin NP-1 solution (70 ug/ml in 0.01% acetic acid). An equal volume of bacterial suspension in tryptone was added and the test tubes were incubated on a roller at 37° C. for 2 hours. The final volume in each reaction tube was 0.1 ml, making the final concentration of defensin 35 ug/ml.

Defensin is inactivated by the high salt and high protein concentration present in bacterial growth media, e.g. LB broth. Thus, defensin activity was stopped by adding 900 ul of Luria broth to each tube. Serial dilutions of each tube were plated and cfu/ml was determined for both the control tube and treatment tube for each strain. Results were expressed as log of bacteria killed for each strain. Typically, 1.0–1.5 log of wild type bacteria were killed. phoP null mutants generally exhibit 2–4 logs of killing. Since strains with slower growth rates appear less susceptible to defensin killing, the growth rate of each strain tested in the defensin sensitivity assay was measured. Strains with similar growth rates were compared in the defensin sensitivity assay.

The HpaI deletion was evaluated both in an *S. typhimurium* background and in the *S. typhi* background. In both backgrounds, the deletion mutation conferred sensitivity to rabbit defensin NP-1 at a concentration of 35 ug/ml. See FIG. 11 and FIG. 13. The difference between $phoP^+$ and HpaI deleted phoP null mutants was less pronounced in the *S. typhi* strain, an effect that may reflect the slower growth rate of the less hardy *S. typhi* strain compared to the *S. typhimurium* strain which lacks the additional auxotrophies.

The state of phoP activation in bacteria with the HpaI phoP/phoQ deletion was tested utilizing a LacZ recorder gene fused to phoP-activated gene B (pagB). Since the efficiency of transduction utilizing P22 in *S. typhi* is low, these studies were performed in *S. typhimurium* rather than *S. typhi*. PhoP activation was found to be 40–60 Miller units (Miller et al., 1972, *Experiments in Molecular Genetics*, Cold Spring Harbor Laboratory, Cold Spring Harbor, N.Y., pp. 352–355) in the presence of an intact phoP/phoQ locus, and just barely detectable in strains with the HpaI deletion (3 cfu see FIG. 12).

In vivo evaluation of *S. typhimurium* HpaI deleted strain

As *S. typhi* strains are not pathogenic for mice, the HpaI phoP/phoQ deletion mutation was evaluated in both wild type and aroA- *S. typhimurium*. Female BALB/c mice were injected intraperitoneally with various dilutions of *S. typhimurium* LH430, a wild type *S. typhimurium* carrying the HpaI deletion. The $LD_{50}$ of this strain was determined to be between $8.2\times10^5$ and $8.2\times10^6$. (All mice receiving $8.2\times10^5$ cfu survived, and all receiving $8.2\times10^6$ died.) These data are consistent with the $LD_{50}$ data obtained with strains harboring transposon insertions at the phoP/phoQ locus.

Immunogenicity of the HpaI phoP/phoQ deletion was evaluated in *S. typhimurium* aroA::tet (LH481), a strain comparable to the human vaccine strain. Mice were inoculated intraperitoneally with $2.3\times10^5$ and $2.3\times10^6$ cfu of LH481 (4 mice per vaccine dose), and challenged 30 days later with 30×the $LD_{50}$ of wild type organisms. All mice but one mouse survived. The mouse that died was in the group that received the lower vaccine dose. No animal receiving the higher vaccine dose became ill.

EXAMPLE 4

Phase I study human studies

The vaccine strain was administered to human volunteers at doses of $1\times10^5$ to $1\times10^{10}$ cfu/single oral dose. Two volunteers received each dose; 3 volunteers were given a dose of $1\times10^8$ cfu/ml. Volunteers were evaluated at various time points following administration of the vaccine.

Safety

To detect the presence of the vaccine strain in patient blood, Bactec blood cultures were performed in duplicate on days 4, 6, 8, 10, 12 after taking vaccine. Bacteremia was not detected in any of the volunteers.

Thirteen adult human volunteers have received escalating single oral doses of this new attenuated typhoid fever vaccine. No individuals have had side effects of any sort. Specifically, there have been no fevers, no gastrointestinal symptoms, and no constitutional symptoms. Volunteers have been subjected to serial blood cultures on a preset schedule after receiving the oral vaccine 2 sets of BACTEC blood cultures performed on each of days 4, 6, 8, 10 and 12 after receiving the vaccine, and no positive blood cultures have been noted. Volunteers have been followed up at 2 months after receiving the vaccine, and no late symptoms have been reported.

Colonization

Stool samples were tested for the presence of the vaccine strain TyLH455 using methods known in the art. Primary stool was evaluated for the presence of the vaccine strain on culture plates. In some cases, it was necessary to enrich stool samples for the vaccine strain by incubating the stool overnight in BBL Selenite F broth supplemented with Aro/His/Cystine in order to detect the bacteria. This medium is somewhat inhibitory for *E. coli* and but promotes Salmonella growth.

Volunteers have been colonized for various time periods from 1–6 days after receiving the vaccine. With the highest doses ($10^9$ or $10^{10}$) volunteers have had positive primary culture plates in the initial 1–3 days post vaccination, whereas at lower doses, only selenite enrichment broth cultures (selective medium for Salmonella which inhibits other enterics) have been positive for the vaccine organism. No volunteer studied thus far has had prolonged carriage of the vaccine organism at 2 months of followup.

TABLE 17

| Dose | Number | Colonization |
|---|---|---|
| $10^5$ | 2 | NO |
| $10^6$ | 2 | 2/2 for 1–2 days |
| $10^7$ | 2 | 1/2 for 3 days |
| $10^8$ | 3 | 1/3 for 6 days |
| $10^9$ | 2 | 2/2 for 4–6 days both had positive primary plates day 1 |
| $10^{10**}$ | 2 | 2/2 for 3–6 days both had positive primary plates on days 1 and 2 |

*Measured by whole cell and LPS ELISAs and Widal test vs. H flagellar antigen. Sera analyzed at 1:40 and higher dilutions in all tests.
**One of these volunteers has received a booster dose of $10^{10}$ organisms, given one month after the primary inoculation (serologies pending).

Immunogenicity

Induction of an immune response to the vaccine strain was measured by standard ELISA assays. Sera was collected from volunteers 0, 7, 14, 21, and 28 days after receiving a single oral dose of the vaccine. ELISA assays were carried out using whole bacteria TyLH445 and *S. typhi* LPS (SIGMA, St. Louis, Mo.) as antigens. Day 0 serum from each volunteer was used as an internal negative control. Convalescent sera from patients previously infected with wild type *S. typhi* (most from Mexico) were used as positive controls.

Several volunteers had documented seroconversion at 21 days after receiving the vaccine, as measured by ELISA in which IgG antibodies directed against whole vaccine organisms or against *S. typhi* LPS were detected. Sera taken from patients prior to administration of the vaccine (pre-immune sera) were tested and the data used to establish a baseline. Patient sera taken at various time points after vaccination were considered positive if the test results were 0.2 ELISA OD units greater than that of the preimmune serum.

OTHER EMBODIMENTS

Other embodiments, e.g., strains of Salmonella which contain only a deletion in the phoP/phoQ regulatory locus to attenuate virulence, and strains which, in addition to a phoP related mutation or genetic alteration, also contain an attenuating mutation in another gene, e.g., cya gene (adenylate cyclase) or crp gene (adenylate cyclase receptor), are also within the claims.

TABLE 1A

Immunological Responses to Ty800 and Ty21a.

| Vaccine/Dose | Volunteer | IgA ASC | Widal tube test titers vs. H Agn Pre | Peak | IgG Endpoint titer vs. LPS Pre | Peak | Serum IgA vs. LPS |
|---|---|---|---|---|---|---|---|
| TY800/1 dose | | | | | | | |
| $7 \times 10^7$ | 1 | 0 | <1:20 | <1:20 | 1:40 | 1:40 | 0.01 |
| | 2 | 400* | <1:20 | 1:640* | 1:80 | 1:640* | 0.20* |
| $6 \times 10^8$ | 3 | 300* | <1:20 | 1:160* | <1:40 | 1:80 | 0.04 |
| | 4 | 1,725* | <1:20 | 1:320* | 1:40 | 1:320* | 0.35* |
| | 5 | 475* | <1:20 | 1:40 | 1:80 | 1:640* | 0.17* |
| $8 \times 10^9$ | 6 | 1,075* | <1:20 | <1:20 | 1:640 | 1:640 | 0.14* |
| | 7 | 90* | <1:20 | <1:20 | 1:40 | 1:40 | 0.01 |
| | 8 | 1,250* | <1:20 | <1:20 | 1:160 | 1:320 | 0.41* |
| $4 \times 10^{10}$ | 9 | 2,400* | <1:20 | 1:80* | 1:40 | 1:160* | 0.47* |
| | 10 | 2,388* | <1:20 | 1:1280* | 1:40 | 1:80 | 0.18* |
| | 11 | 2,950* | <1:20 | 1:160* | 1:40 | 1:640* | 0.60* |
| Ty21a/4 doses | | | | | | | |
| | 12 | ND | <1:20 | <1:20 | 1:80 | 1:640* | 0.17* |
| | 13 | ND | <1:20 | <1:20 | 1:640 | 1:640 | 0.26* |
| | 14 | ND | <1:20 | <1:20 | 1:640 | 1:640 | 0.04 |
| | 15 | ND | <1:20 | <1:20 | <1:40 | 1:40 | 0.02 |
| | 16 | ND | <1:20 | <1:20 | 1:160 | 1:640* | 0.06 |
| | 17 | ND | <1:20 | <1:20 | 1:40 | 1:80 | 0.22* |
| | 18 | ND | <1:20 | <1:20 | 1:80 | 1:1280* | 0.10* |
| | 19 | ND | <1:20 | <1:20 | <1:40 | <1:40 | 0.06 |

IgA-antibody-secreting cells (IgA-ASC) directed against against *S. typhi* lipopolysaccharide (LPS) in ELISPOT assay ia reported as spots per $10^6$ mononuclear cells, >6 is significant (*).
Widal tube test titers vs. H Agn reported as the dilution of serum giving a 2+ positive reaction; preimmine (pre) vs. peak; >4-fold increase is signficant (*).
Endpoint titer vs. LPS is the dilution of serum at which the specific optical density exceeded 0.15 OD units in ELISA against *S. typhi* LPS; greater than 4-fold increase is significant(*).
Serum IgA vs. LPS is reported as optical density units for 1:80 dilutions of serum in ELISA detecting IgA directed against *S. typhi* LPS; >0.07 OD units is a significant rise(*). Volunteer 13 previously received parenteral typhoid vaccination more than 30 years prior to the study.
ND: not done.

We claim:

1. A vaccine comprising a *Salmonella typhi* Ty800 cell, said cell comprising a mutation in the phoQ gene, wherein said mutation attenuates virulence and does not result in the insertion of an antibiotic resistance gene into said phoQ gene.

* * * * *

SEQUENCE LISTING ( 1 ) GENERAL INFORMATION:

( i i i ) NUMBER OF SEQUENCES: 15

( 2 ) INFORMATION FOR SEQ ID NO: 1:

( i ) SEQUENCE CHARACTERISTICS:
        ( A ) LENGTH: 2320
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO: 1:

```
GTTAACCACT  CTTAATAATA  ATGGGTTTTA  TAGCGAAATA  CACTTTTTTA  TCGCGTGTTC    60

AATATTTGCG  TTAGTTATTA  TTTTTTTGGA  ATGTAAATTC  TCTCTAAACA  CAGGTGATAT   120

TTATGTTGGA  ATTGTGGTGT  TGATTCTATT  CTTATAATAT  AACAAGAAAT  GTTGTAACTG   180

ATAGATATAT  TAAAAGATTA  AATCGGAGGG  GGAATAAAGC  GTGCTAAGCA  TCATCGTGAA   240

TATGATTACA  GCGCCTGCGA  TGGCATATAA  CCGTATTGCG  GATGGAGCGT  CACGTGAGGA   300

CTGTGAAGCA  CAATGCGATA  TGTTCTGATT  ATATGGCGAG  TTTGCTTAAT  GACATGTTTT   360

TAGCCGAACG  GTGTCAAGTT  TCTTAATGTG  GTTGTGAGAT  TTTCTCTTTA  AATATCAAAA   420

TGTTGCATGG  GTGATTTGTT  GTTCTATAGT  GGCTAAAGAC  TTTATGGTTT  CTGTTAAATA   480

TATATGCGTG  AGAAAAATTA  GCATTCAAAT  CTATAAAGT   TAGATGACAT  TGTAGAACCG   540

GTTACCTAAA  TGAGCGATAG  AGTGCTTCGG  TAGTAAAAAT  ATCTTTCAGG  AAGTAAACAC   600

ATCAGGAGCG  ATAGCGGTGA  ATTATTCGTG  GTTTTGTCGA  TTCGGCATAG  TGGCGATAAC   660

TGAATGCCGG  ATCGGTACTG  CAGGTGTTTA  AACACACCGT  AAATAATAAG  TAGTATTAAG   720

GAGTTGTT                                                                728
```

| | | | | | | | | | | | | | | | | |
|---|---|---|---|---|---|---|---|---|---|---|---|---|---|---|---|---|
| ATG | AAA | AAT | ATT | ATT | TTA | TCC | ACT | TTA | GTT | ATT | ACT | ACA | AGC | GTT | TTG | 776 |
| Met | Lys | Asn | Ile | Ile | Leu | Ser | Thr | Leu | Val | Ile | Thr | Thr | Ser | Val | Leu | |
| | | | | 5 | | | | 10 | | | | | | 15 | | |
| GTT | GTA | AAT | GTT | GCA | CAG | GCC | GAT | ACT | AAC | GCC | TTT | TCC | GTG | GGG | TAT | 824 |
| Val | Val | Asn | Val | Ala | Gln | Ala | Asp | Thr | Asn | Ala | Phe | Ser | Val | Gly | Tyr | |
| | | | 20 | | | | | 25 | | | | | 30 | | | |
| GCA | CGG | TAT | GCA | CAA | AGT | AAA | GTT | CAG | GAT | TTC | AAA | AAT | ATC | CGA | GGG | 872 |
| Ala | Arg | Tyr | Ala | Gln | Ser | Lys | Val | Gln | Asp | Phe | Lys | Asn | Ile | Arg | Gly | |
| | | 35 | | | | | 40 | | | | | 45 | | | | |
| GTA | AAT | GTG | AAA | TAC | CGT | TAT | GAG | GAT | GAC | TCT | CCG | GTA | AGT | TTT | ATT | 920 |
| Val | Asn | Val | Lys | Tyr | Arg | Tyr | Glu | Asp | Asp | Ser | Pro | Val | Ser | Phe | Ile | |
| | 50 | | | | | 55 | | | | | 60 | | | | | |
| TCC | TCG | CTA | AGT | TAC | TTA | TAT | GGA | GAC | AGA | CAG | GCT | TCC | GGG | TCT | GTT | 968 |
| Ser | Ser | Leu | Ser | Tyr | Leu | Tyr | Gly | Asp | Arg | Gln | Ala | Ser | Gly | Ser | Val | |
| 65 | | | | | 70 | | | | | 75 | | | | | 80 | |
| GAG | CCT | GAA | GGT | ATT | CAT | TAC | CAT | GAC | AAG | TTT | GAG | GTG | AAG | TAC | GGT | 1016 |
| Glu | Pro | Glu | Gly | Ile | His | Tyr | His | Asp | Lys | Phe | Glu | Val | Lys | Try | Gly | |
| | | | | 85 | | | | 90 | | | | | 95 | | | |
| TCT | TTA | ATG | GTT | GGG | CCA | GCC | TAT | CGA | TTG | TCT | GAC | AAT | TTT | TCG | TTA | 1064 |
| Ser | Leu | Met | Val | Gly | Pro | Ala | Tyr | Arg | Leu | Ser | Asp | Asn | Phe | Ser | Leu | |
| | | | 100 | | | | 105 | | | | 110 | | | | | |
| TAC | GCG | CTG | GCG | GGT | GTC | GGC | ACG | GTA | AAG | GCG | ACA | TTT | AAA | GAA | CAT | 1112 |
| Tyr | Ala | Leu | Ala | Gly | Val | Gly | Thr | Val | Lys | Ala | Thr | Phe | Lys | Glu | His | |
| | | 115 | | | | | 120 | | | | 125 | | | | | |
| TCC | ACT | CAG | GAT | GGC | GAT | TCT | TTT | TCT | AAC | AAA | ATT | TCC | TCA | AGG | AAA | 1160 |
| Ser | Thr | Gln | Asp | Gly | Asp | Ser | Phe | Ser | Asn | Lys | Ile | Ser | Ser | Arg | Lys | |

```
                130                           135                           140
ACG  GGA  TTT  GCC  TGG  GGC  GCG  GGT  GTA  CAG  ATG  AAT  CCG  CTG  GAG  AAT        1208
Thr  Gly  Phe  Ala  Trp  Gly  Ala  Gly  Val  Gln  Met  Asn  Pro  Leu  Glu  Asn
145                           150                           155                 160

ATC  GTC  GTC  GAT  GTT  GGG  TAT  GAA  GGA  AGC  AAC  ATC  TCC  TCT  ACA  AAA        1256
Ile  Val  Val  Asp  Val  Gly  Tyr  Glu  Gly  Ser  Asn  Ile  Ser  Ser  Thr  Lys
                    165                           170                      175

ATA  AAC  GGC  TTC  AAC  GTC  GGG  GTT  GGA  TAC  CGT  TTC  TGA  AAAGC               1300
Ile  Asn  Gly  Phe  Asn  Val  Gly  Val  Gly  Tyr  Arg  Phe
                180                      185

ATAAGCTATG   CGGAAGGTTC   GCCTTCCGCA   CCGCCAGTCA   ATAAACAGG   GCTTCTTTAC            1360

CAGTGACACG   TACCTGCCTG   TCTTTTCTCT   CTTCGTCATA   CTCTCTTCGT   CATAGTGACG           1420

CTGTACATAA   CATCTCACTA   GCATAAGCAC   AGATAAAGGA   TTGTGGTAAG   CAATCAAGGT           1480

TGCTCAGGTA   GGTGATAAGC   AGGAAGGAAA   ATCTGGTGTA   AATAACGCCA   GATCTCACAA           1540

GATTCACTCT   GAAAAATTTT   CCTGGAATTA   ATCACAATGT   CATCAAGATT   TTGTGACCGC           1600

CTTCGCATAT   TGTACCTGCC   GCTGAACGAC   TACTGAAAAG   TAGCAAGGTA   TGTATTTTAT           1660

CCAGGAGAGC   ACCTTTTTTG   CGCCTGGCAG   AAGTCCCCAG   CCGCCACTAG   CTCAGCTGGA           1720

TAGAGCATCA   ACCTCCTAAG   TTGATGGTGC   GAGGTTCGAG   GCCTCGGTGG   CGGTCCAATG           1780

TGGTTATCGT   ATAATGTTAT   TACCTCAGTG   TCAGGCTGAT   GATGTGGGTT   CGACTCCCAC           1840

TGACCACTTC   AGTTTTGAAT   AAGTATTGTC   TCGCAACCCT   GTTACAGAAT   AATTTCATTT           1900

ATTACGTGAC   AAGATAGTCA   TTTATAAAAA   ATGCACAAAA   ATGTTATTGT   CTTTTATTAC           1960

TTGTGAGTTG   TAGATTTTTC   TTATGCGGTG   AATCCCCTT   TGCGGCGGGG   CGTCCAGTCA            2020

AATAGTTAAT   GTTCCTCGCG   AACCATATTG   ACTGTGGTAT   GGTTCACCGG   GAGGCACCCG           2080

GCACCGCAAT   TTTTTATAAA   ATGAAATTCA   CACCCTATGG   TTCAGAGCGG   TGTCTTTTA            2140

CATCAGGTGG   GCAAGCATAA   TGCAGGTTAA   CTTGAAAGAT   ACGATCAATA   GCAGAAACCA           2200

GTGATTTCGT   TTATGGCCTG   GGGATTTAAC   CGCGCCAGAG   CGTATGCAAG   ACCCTGGCGC           2260

GGTTGGCCGG   TGATCGTTCA   ATAGTGCGAA   TATGAATGGT   TACCAGCCGC   CTGCGAATTC           2320
```

( 2 ) INFORMATION FOR SEQ ID NO: 2:

( i ) SEQUENCE CHARACTERISTICS:
    ( A ) LENGTH: 53
    ( B ) TYPE: nucleic acid
    ( C ) STRANDEDNESS: single
    ( D ) TOPOLOGY: linear ( x i ) SEQUENCE DESCRIPTION: SEQ ID NO: 2:

```
CATTTCTCAT   TGATAATGAG   AATCATTATT   GACATAATTG   TTATTATTTT   ACG                  53
```

( 2 ) INFORMATION FOR SEQ ID NO: 3:

( i ) SEQUENCE CHARACTERISTICS:
    ( A ) LENGTH: 688
    ( B ) TYPE: nucleic acid
    ( C ) STRANDEDNESS: double
    ( D ) TOPOLOGY: linear ( x i ) SEQUENCE DESCRIPTION: SEQ ID NO: 3:

```
GAGCGCATTA   TCAGATAAAT   TGATTTATTT   CTCACTTTCA   TTCTATTTTC   ATCAGGAATC           60

CCTGTGTCCT   GTGCGGTAAT   CTGCTGCTAT   CGAGAACGAC   AGACATCGCT   AACAGTATAT          120

ATGGAAACAT   CAAAAGAGAA   GACGATAACA   AGCCCAGGGC   CATACATAGT   TCGATTACTT          180

AACAGCTCAC   TGAACGGCTG   TGAGTTTCCA   TTGCTGACAG   GCCGAACACT   CTTTGTGGTA          240
```

-continued

| | | | | | | |
|---|---|---|---|---|---|---|
| GGTCAGAGTG | ATGCGCTCAC | TGCTTCAGGT | CAACTCCCTG | ATATACCTGC | CGATAGCTTT | 300 |
| TTTATCCCGC | TGGACCATGG | CGGAGTAAAT | TTTGAAATCC | AGGTGGATAC | GGATGCGACC | 360 |
| GAAATTATAC | TCCATGAGCT | GAAAGAAGGA | AATTCTGAAT | CTCGTTCGGT | GCAATTAAAT | 420 |
| ACGCCAATAC | AGGTCGGTGA | ATTGCTTATC | CTGATTCGCC | CGGAAAGCGA | GCCGTGGGTG | 480 |
| CCCGAGCAGC | CTGAGAAGTT | AGAAACGTCT | GCAAAAAGA | ACGAGCCGCG | TTTTAAAAAC | 540 |
| GGAATTGTAG | CAGCACTGGC | CGGGTTTTTT | ATATTGGGAA | TTGGGACTGT | GGGGACGTTA | 600 |
| TGGATACTTA | ACTCGCCGCA | GCGGCAGGCC | CGAGAGCTCG | ATTCGTTATT | GGGGCAGGAG | 660 |
| AAGGAGCGTT | TTCAGGTGTT | GCCAGGCC | | | | 688 |

( 2 ) INFORMATION FOR SEQ ID NO: 4:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 4:

| | | |
|---|---|---|
| AATATCGCCC | TGAGCA | 16 |

( 2 ) INFORMATION FOR SEQ ID NO: 5:

( i ) SEQUENCE CHARACTERISTICS:
        ( A ) LENGTH: 4044
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO: 5:

| | | | | | | |
|---|---|---|---|---|---|---|
| GGTTAACTCT | TCGTTGAATA | AAAAATGTCA | ATGACGTTCC | ATAATTCAGG | AGATGAACTT | 60 |
| CACAAGTCAT | TATATATAAC | AGGAGGTGCT | ATGAAACATC | ATGCTTTAT | GCTTTGGTCA | 120 |
| TTACTTATTT | TTTCATTCCA | TGTTTTGGCC | AGTTCAGGCC | ATTGTTCTGG | TTTACAACAG | 180 |
| GCATCATGGG | ATATTTTTAT | CTACGATTTT | GGTAGTAAAA | CCCCGCAACC | ACCTACAAAT | 240 |
| ACTGATAAAA | AGCAAGCCAG | GCAGATTAGT | TCACCGTCCT | GCCCGACGAC | AAAACCCATG | 300 |
| ATGTCCGCAC | CAGTCAATGA | CGCCAGGAAA | GGGAATACTT | TCTCCAGAAC | ATAATGTTAT | 360 |
| TTATCTACAA | TGGTGCCGAC | GACTACTTTT | AGCCACCCGG | AAATCTTGAT | TGCCATCAAA | 420 |
| TATAGCTGGC | ATTATTTTC | CTGACGTGTA | TAGTGCGCCT | CGTTATCCCC | ATTAAGGAAT | 480 |
| TTGTTTGTCT | CGTAAAATGA | CAGGAATTGT | CAAAACCTTT | GATTGTAAGA | GCGGTAAAGG | 540 |
| TCTCATCACC | CCCTCCGATG | ACGCAAAGAT | GTTCAGGTCC | ACATTTCAGC | ATGTCGCCAA | 600 |
| CACGAAACAG | AAGCGCTTAT | CCCCGGTATA | CGCGTTGAGT | TTTATCGTAT | TAATGGCCTC | 660 |
| CGCGGACCTA | CCGCCGCCAA | CGTTTATCTT | TCATAATTCG | TCACCCGGCA | TTTTTCAGAA | 720 |
| AAATTTAGCG | AGTACGTCTA | CCTCCGCAGC | CTGCTATGAG | GCTTTGCCTG | AAAGGCTGCA | 780 |
| GAATGTTTTC | AGTGGCGAAA | ATCTAAAAGA | TTTATTTTGC | TAATCAGTCC | TGTGACCTCT | 840 |
| TTTATCATAT | ATCGGGTGCC | CCCCCTTCTC | ACTTTGTTTA | ACGTGAAGAA | ATGTACAGCC | 900 |
| GTTTTTCACT | GTGATAGCAT | CTAATATTGC | AAAAGTATTT | AACGCTATAT | ACCCATTGTC | 960 |
| ACAGGAGTGG | CTGCGTGCGA | GCTGAGCTAT | TTAACCGAAG | TATTTATGTG | ATCATTGGAA | 1020 |
| TTATCTCTAT | TGCCGCTCAA | TGCTACGTCA | TATTCAGTGG | GTATAAATCG | CCAATATAGT | 1080 |

| | | | | | | |
|---|---|---|---|---|---|---|
| TGTAACGCTA | TTTATTTTTA | GGGTAATAAT | TGAATGACTT | TGCTTTCAGG | AAAAACCACA | 1140 |
| CTGGTTCTCT | GCCTCTCCTC | TATTTTATGT | GGATGTACGA | CGAACGGCTT | ACCCACACCT | 1200 |
| TATAGTATTA | ATTTGTCGTT | CCCGGTCATT | ACACAAAACC | AGATTAATTC | CGGTGGTTAT | 1260 |
| TACATAAATG | ACGCGGAACA | AATTCGGACA | ACTGATGGTC | TGTGCCTTGA | TGCAGGCCCA | 1320 |
| GATCAACAGA | ATCGTTTGAC | GCTGCGGGAG | TGTAAGCATG | TGCAATCTCA | GCTTTTCTCA | 1380 |
| TTTCACCGAG | ACAGAATCAC | GCAGGGTGAG | AAATGTCTGG | ATGCCGCAGA | CAAGGTACAA | 1440 |
| AAGAAGGCAC | ACCAATCATT | CTTTATTCAT | GCACGGGTAA | TGATAACCAG | CGCTGGCTCA | 1500 |
| CTGATCATAA | CAAAATTAAG | GGGAAACAGA | GCCGAAAATG | CCTGGGCACA | AATAGCATTA | 1560 |
| TTGTCAGAAA | AGGCGACCCT | GTTGTGTTGG | CCGATTGCGA | TTTTAGTCGC | GCCCTGGAAT | 1620 |
| TTACCATCAG | GTAGCAGGAC | ACCGCTGTGA | AGAGAGTGCC | GCTAACCTCT | TGACACGACA | 1680 |
| ACAGGTTAGC | GACCTTTACT | TCCACGTGCG | ATCAATTTAC | TTTACGTCCG | CAACGTCAGG | 1740 |
| ATGACAAAAC | GGCGGCTAAA | CCTTGACACC | AGTTATATAC | CCAGCTTAAA | TACTGGTCAT | 1800 |
| CCAACCAGTA | AAAAGGAAAT | GGCGATGTTC | GTCGAACTCG | TTTATGACAA | GCGAAATGTT | 1860 |
| GAAGGTTTGC | CAGGCGCACG | CGAAATCATC | CTCAATGAAC | TCACAAAACG | CGTACATCAA | 1920 |
| CTTTTTCCCG | ATGCGCAAGT | GAAAGTTAAG | CCAATGCAGG | CGAACGCATT | AAACAGTGAC | 1980 |
| TGTACAAAAA | CCGAGAAAGA | ACGGCTGCAC | CGTATGCTGG | AAGAGATGTT | TGAAGAGGCT | 2040 |
| GATATGTGGC | TGGTCGCCGA | ATAACGTCCC | CTCCTGCGAA | AGCCAACATG | TCCGATCGAA | 2100 |
| AACAGCGCCC | TGAGGCGCTG | TCTGTGACGA | TATAACGCAA | ACGCTACCAC | TCAGAACATG | 2160 |
| TTGTTGTTGA | TACCTCAGAC | CGGTATGTGG | AACCGACATT | CATCGCTTCA | CTGGCCTGTC | 2220 |
| GGTATGAGTA | GCCCTTATCA | ACAATCAGCT | GTGCGCATTC | CAGCCTGAAA | TCTGAAAGTA | 2280 |
| CGTTTGGTTT | TGTTGTTTAT | TAAGAGCCTA | TCCATTAGA | CTCTTTTATT | CGCCAAACTG | 2340 |
| GCTTTAACGA | TTACGCCTAC | TGGGATAGGT | TCTAAACTTA | TCATCAATAC | GTAAAATACC | 2400 |
| TATTTACGAA | CAAAAAGTAA | CAGGTAAAAA | TCCGAAATAA | AACCAGCATA | ACTAAAACTT | 2460 |
| ACTGCAGATA | TGCACACGCA | TTATTACTAT | GTTCCAGGA | TAGTCTCGAC | CAGTCAAGAC | 2520 |
| TATCTATTTT | ATATAAAAG | GGAAATACTT | CACATGAATA | AAATACATGT | TACATATAAA | 2580 |
| AATCTCTTAC | TTCCGATTAC | CTTCATCGCG | GCAACTCTAA | TTAGCGCCTG | TGATAACGAT | 2640 |
| AAAGATGCCA | TGGCGGAAGC | TGAAAAAAAT | CAAGAGAAAT | ACATGCAAAA | AATCCAGCAA | 2700 |
| AAAGAGCACC | AGCAATCAAT | GTTCTTTTAC | GACAAAGCCG | AAATGCAAAA | AGCTATTGCC | 2760 |
| AATATCAACG | CAAAAGGTGG | AGCCAATCTT | GCGATTATTG | AAGTCCGTTT | CTTCAAGGGC | 2820 |
| GGGTATTCAT | TCATTCGACA | AAGCGTTAAC | ACCCCTGCTA | AGTAGAGGT | GTTTAAATTT | 2880 |
| AACAACGGCT | ACTGGGGGGG | ACCTTCGCCT | GTCAATTTAA | CCATCTTTGG | CACTATAACA | 2940 |
| GAGGAGCAAA | AACAAGAAGC | ACTAAAAGAG | GCTTTATTCA | AATTCGACTC | GATCAATTTC | 3000 |
| AGCATTATAC | CAGAGCGTAT | TCAGGAAACA | ATTAAACGCG | CTAACGCCAG | TGGCATCATT | 3060 |
| TCCGTTACGG | AAGATAGCGA | TATCGTTGTA | CGAGCAGAGA | TAGCTCATAA | TGGCGAATTC | 3120 |
| GTCTATGACA | TTACCATCAC | TGCTAAAAAT | ACAGCACGTG | CGGTAATGAC | CTTAAATAAG | 3180 |
| GATGGTTCTA | TTGCCGGATA | TGAGATCAAA | GAACCTTTCG | CCCCAAAAAA | AGAAGCCGAA | 3240 |
| AAAGCACAGC | AACTTGTTGA | ACAATCGAGA | AAAGACATTG | AAAGTCCAGC | GTAAAAAAGC | 3300 |
| AGCTGGAAAG | ATGAACGAAA | TACAGCAGAC | ATTTAAAAAT | AGCAGGCGAT | ACAAACATTG | 3360 |
| ATAAAAATTA | TAGCGCGAAA | GAGCGCGTGC | CAGGTACTAA | GGCACTGCTT | GAAGACAGCG | 3420 |
| AATCGCTATT | TCATTCTCTG | ACACTGTAAT | TTTTCGTACT | CAAGATGTTT | ATTTATTGAG | 3480 |

| | | | | | |
|---|---|---|---|---|---|
| TCTTTTGTGG | ATAACCAGGT | GAAGTTATGT | GACGCCAGGA | ATCTATTCCA | GCGGGCGTAC | 3540 |
| TTGTTGGAGC | CAGTGTGAAG | CCGGGCAGCG | CGCAGAAACC | GGAGCGTATA | CGTTGTACGT | 3600 |
| AAGAATTTCG | AGCACTGCCC | GACCTAAAAA | TGATGAATAA | AATAGATATT | TTAAAGAGGT | 3660 |
| AATATGAAGA | ATTTTTTCAA | AATAATTACT | GATTTCATCG | CGGATATTTC | CCTTGATCTA | 3720 |
| TTTGCTATAT | TTTTATGCAT | GTTATTCGTA | TACAAAACAG | GACCATCAAT | TGGTGTGATA | 3780 |
| TCATTTTTTA | TTGCATTAAT | TATTTATATC | ATTCTTCATT | TTTTTTACT | CATTTCTTGA | 3840 |
| AAAAATCATA | AAAAAAATAT | TCAAATAAGT | ATTTAAAATT | ATTGTTTTGT | GGTACAAATT | 3900 |
| CAGCGCAATA | AAACAGAGCA | ACTAAAAAAA | ATTAGGCGTA | GCGAAGTGGA | AAAGGACTGT | 3960 |
| CATGTACTGG | ACCGTGAGCT | GGTCGGGAGA | GCAATGTACG | GGAAAGAGCG | AAATACTGTC | 4020 |
| ATTGATATGA | GCAGGAATAT | CGAT | | | | 4044 |

( 2 ) INFORMATION FOR SEQ ID NO: 6:

( i ) SEQUENCE CHARACTERISTICS:

( i ) SEQUENCE CHARACTERISTICS:
        ( A ) LENGTH: 87 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 6:

```
Met  Lys  His  His  Ala  Phe  Met  Leu  Trp  Ser  Leu  Leu  Ile  Phe  Ser  Phe
 1                    5                        10                       15

His  Val  Leu  Ala  Ser  Ser  Gly  His  Cys  Ser  Gly  Leu  Gln  Gln  Ala  Ser
                   20                       25                       30

Trp  Asp  Ile  Phe  Ile  Tyr  Asp  Phe  Gly  Ser  Lys  Thr  Pro  Gln  Pro  Pro
              35                       40                       45

Thr  Asn  Thr  Asp  Lys  Lys  Gln  Ala  Arg  Gln  Ile  Ser  Ser  Pro  Ser  Cys
         50                       55                       60

Pro  Thr  Thr  Lys  Pro  Met  Met  Ser  Ala  Pro  Val  Asn  Asp  Ala  Arg  Lys
65                       70                       75                       80

Gly  Asn  Thr  Phe  Ser  Arg  Thr
                   85
```

( 2 ) INFORMATION FOR SEQ ID NO: 7:

( i ) SEQUENCE CHARACTERISTICS:
        ( A ) LENGTH: 178 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 7:

```
Met  Thr  Leu  Leu  Ser  Gly  Lys  Thr  Thr  Leu  Val  Leu  Cys  Leu  Ser  Ser
 1                    5                        10                       15

Ile  Leu  Cys  Gly  Cys  Thr  Thr  Asn  Gly  Leu  Pro  Thr  Pro  Tyr  Ser  Ile
                   20                       25                       30

Asn  Leu  Ser  Phe  Pro  Val  Ile  Thr  Gln  Asn  Gln  Ile  Asn  Ser  Gly  Gly
              35                       40                       45

Tyr  Tyr  Ile  Asn  Asp  Ala  Glu  Gln  Ile  Arg  Thr  Thr  Asp  Gly  Leu  Cys
         50                       55                       60

Leu  Asp  Ala  Gly  Pro  Asp  Gln  Gln  Asn  Arg  Leu  Thr  Leu  Arg  Glu  Cys
65                       70                       75                       80

Lys  His  Val  Gln  Ser  Gln  Leu  Phe  Ser  Phe  His  Arg  Asp  Arg  Ile  Thr
```

|   |   |   |   |   | 85 |   |   |   |   | 90 |   |   |   |   | 95 |   |   |
|---|---|---|---|---|---|---|---|---|---|---|---|---|---|---|---|---|---|
| Gln | Gly | Glu | Lys<br>100 | Cys | Leu | Asp | Ala | Ala<br>105 | Asp | Lys | Val | Gln | Lys<br>110 | Lys | Ala |
| His | Gln | Ser<br>115 | Phe | Phe | Ile | His | Ala<br>120 | Arg | Val | Met | Ile | Thr<br>125 | Ser | Ala | Gly |
| Ser | Leu<br>130 | Ile | Ile | Thr | Lys | Leu<br>135 | Arg | Gly | Asn | Arg | Ala<br>140 | Glu | Asn | Ala | Trp |
| Ala<br>145 | Gln | Ile | Ala | Leu | Leu<br>150 | Ser | Glu | Lys | Ala | Thr<br>155 | Leu | Leu | Cys | Trp | Pro<br>160 |
| Ile | Ala | Ile | Leu | Val<br>165 | Ala | Pro | Trp | Asn | Leu<br>170 | Pro | Ser | Gly | Ser | Arg<br>175 | Thr |
| Pro | Leu |

( 2 ) INFORMATION FOR SEQ ID NO: 8:

( i ) SEQUENCE CHARACTERISTICS:
        ( A ) LENGTH: 79 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 8:

| Met<br>1 | Phe | Val | Glu | Leu<br>5 | Val | Tyr | Asp | Lys | Arg<br>10 | Asn | Val | Glu | Gly | Leu<br>15 | Pro |
|---|---|---|---|---|---|---|---|---|---|---|---|---|---|---|---|
| Gly | Ala | Arg | Glu<br>20 | Ile | Ile | Leu | Asn | Glu<br>25 | Leu | Thr | Lys | Arg | Val<br>30 | His | Gln |
| Leu | Phe | Pro<br>35 | Asp | Ala | Gln | Val | Lys<br>40 | Val | Lys | Pro | Met | Gln<br>45 | Ala | Asn | Ala |
| Leu | Asn<br>50 | Ser | Asp | Cys | Thr | Lys<br>55 | Thr | Glu | Lys | Glu | Arg<br>60 | Leu | His | Arg | Met |
| Leu<br>65 | Glu | Glu | Met | Phe | Glu<br>70 | Glu | Ala | Asp | Met | Trp<br>75 | Leu | Val | Ala | Glu |

( 2 ) INFORMATION FOR SEQ ID NO: 9:

( i ) SEQUENCE CHARACTERISTICS:
        ( A ) LENGTH: 246 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 9:

| Met<br>1 | Asn | Lys | Ile | His<br>5 | Val | Thr | Tyr | Lys | Asn<br>10 | Leu | Leu | Leu | Pro | Ile<br>15 | Thr |
|---|---|---|---|---|---|---|---|---|---|---|---|---|---|---|---|
| Phe | Ile | Ala | Ala<br>20 | Thr | Leu | Ile | Ser | Ala<br>25 | Cys | Asp | Asn | Asp | Lys<br>30 | Asp | Ala |
| Met | Ala | Glu<br>35 | Ala | Glu | Lys | Asn | Gln<br>40 | Glu | Lys | Tyr | Met | Gln<br>45 | Lys | Ile | Gln |
| Gln | Lys<br>50 | Glu | His | Gln | Gln | Ser<br>55 | Met | Phe | Phe | Tyr | Asp<br>60 | Lys | Ala | Glu | Met |
| Gln<br>65 | Lys | Ala | Ile | Ala | Asn<br>70 | Ile | Asn | Ala | Lys | Gly<br>75 | Gly | Ala | Asn | Leu | Ala<br>80 |
| Ile | Ile | Glu | Val | Arg<br>85 | Phe | Phe | Lys | Gly | Gly<br>90 | Tyr | Ser | Phe | Ile | Arg<br>95 | Gln |
| Ser | Val | Asn | Thr<br>100 | Pro | Ala | Lys | Val | Glu<br>105 | Val | Phe | Lys | Phe | Asn<br>110 | Asn | Gly |
| Tyr | Trp | Gly | Gly | Pro | Ser | Pro | Val | Asn | Leu | Thr | Ile | Phe | Gly | Thr | Ile |

|     |     |     |     | 115 |     |     |     | 120 |     |     |     | 125 |     |     |
| --- | --- | --- | --- | --- | --- | --- | --- | --- | --- | --- | --- | --- | --- | --- |
| Thr | Glu | Gln | Lys | Gln | Glu | Ala | Leu | Lys | Glu | Ala | Leu | Phe | Lys | Phe |
|     |     | 130 |     |     |     | 135 |     |     |     | 140 |     |     |     |     |
| Asp | Ser | Ile | Asn | Phe | Ser | Ile | Ile | Pro | Glu | Arg | Ile | Gln | Glu | Thr | Ile |
| 145 |     |     |     |     | 150 |     |     |     |     | 155 |     |     |     |     | 160 |
| Lys | Arg | Ala | Asn | Ala | Ser | Gly | Ile | Ile | Ser | Val | Thr | Glu | Asp | Ser | Asp |
|     |     |     |     | 165 |     |     |     |     | 170 |     |     |     |     | 175 |     |
| Ile | Val | Val | Arg | Ala | Glu | Ile | Ala | His | Asn | Gly | Glu | Phe | Val | Tyr | Asp |
|     |     |     | 180 |     |     |     |     | 185 |     |     |     |     | 190 |     |     |
| Ile | Thr | Ile | Thr | Ala | Lys | Asn | Thr | Ala | Arg | Ala | Val | Met | Thr | Leu | Asn |
|     |     | 195 |     |     |     |     | 200 |     |     |     |     | 205 |     |     |     |
| Lys | Asp | Gly | Ser | Ile | Ala | Gly | Tyr | Glu | Ile | Lys | Glu | Pro | Phe | Ala | Pro |
|     | 210 |     |     |     |     | 215 |     |     |     |     | 220 |     |     |     |     |
| Lys | Lys | Glu | Ala | Glu | Lys | Ala | Gln | Gln | Leu | Val | Glu | Gln | Ser | Arg | Lys |
| 225 |     |     |     |     | 230 |     |     |     |     | 235 |     |     |     |     | 240 |
| Asp | Ile | Glu | Ser | Pro | Ala |
|     |     |     |     | 245 |     |

( 2 ) INFORMATION FOR SEQ ID NO: 10:

( i ) SEQUENCE CHARACTERISTICS:
    ( A ) LENGTH: 3700
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO: 10:

| | | | | | |
|---|---|---|---|---|---|
| TTTTGGTTTG | CTGCCGTTTG | GGATAACTGC | ATAGAGAGCG | GCCAAGTCGC | TTGCGGTCGG | 60 |
| TATCTCGAGT | ATATCGAAAT | CCATGTGGCC | ATTGACCTCT | TCAAGCGCTC | ACGTTAACTA | 120 |
| CCTGCTCTTT | TTTGAGCACC | AACATCCCAG | GTTCGTCACA | GTAAATCGTA | TCGTGATTAT | 180 |
| TGCTAATCGT | CAGTTTACCG | CTCCGAAAGC | AAACTAAAGT | GAAACTGCTT | ACATAAAGAT | 240 |
| TTTTGATGGT | AACCTGCTGA | GTCTGACTTT | TAATTTGCTG | CCGGGTATTT | GTCAAAAGTG | 300 |
| ATTTTAATTT | CTGTAAGTTA | TCTGCGGCAG | GACGCTGATG | ACTATTACTT | ACAAAGGTTA | 360 |
| CATTTTCCAT | ATTATCCCTT | TGTTGAACTT | ATTTTAATGT | TCCTTACTGG | TATCCTACTG | 420 |
| AAAAAATCTG | AGTTGTAAAT | GCTCTTTATT | AGCGTGTGTT | GGCAATGGTC | TGATTGTTAC | 480 |
| ACCAAAAGAA | CCCAAATTTG | GGTAATTTAT | CTACAGTAGT | TTAAGCCCCA | ATGGGGATGA | 540 |
| TGGTTCTTTT | AATATGTGTT | GAGACGCATT | ATACAGAATA | AATTGATTTT | ATTTCTCACT | 600 |
| TTTCATTCTA | TTTTCATCAG | GAATCCCTGT | GTCCTGTGCG | GTAATCTGCT | GCTATCGAGG | 660 |
| AACGACAGAC | ATCGCTAACA | GTATATATGG | AAACATCAAA | AGAGAAGACG | ATAACAAGCT | 720 |
| TTCCAGGGCC | ATACATAGTT | CGATTACTTA | ACAGCTCACT | GAACGGCTGT | GAGTTTCCAT | 780 |
| TGGGCCTGAC | AGGCCGAACA | CTCTTTGTGG | TAGGTCAGAG | TGATGCGCTC | ACTGCTTCAG | 840 |
| GTCAATGTGA | TAGCTCCCTG | ATATACCTGC | CGATAGCTTT | TTTATCCCGC | TGGACCATGG | 900 |
| CGGAGTAAAT | TTTAGGGAAA | TCCAGGTGGA | TACGGATGCG | ACCGAAATTA | TACTCCATGA | 960 |
| GCTGAAAGAA | GGAAATTATG | TCTGAATCTC | GTTCGGTGCA | ATTAAATACG | CCAATACAGG | 1020 |
| TCGGTGAATT | GCTTATCCTG | TGATTCGCCC | GGAAAGCGAG | CCGTGGGTGC | CCGAGCAGCC | 1080 |
| TGAGAAGTTA | GAAACGTCTG | CATAAAAAAG | AACGAGCCGC | GTTTTAAAAA | CGGAATTGTA | 1140 |
| GCAGCACTGG | CCGGGTTTTT | TATAGAAAGT | TGGGAATTGG | GACTGTGGGG | ACGTTATGGA | 1200 |
| TACTTAACTC | GCCGCAGCGG | CAGGCCGCAG | GTGTAAGAGC | TCGATTCGTT | ATTGGGGCAG | 1260 |

```
GAGAAGGAGC  GTTTTCAGGT  GTTGCCAGGC  CGGGACGGAA  AATGCTCTAT  GTCGCTGCGC  1320

AAAATGAAAG  AGATACGTTG  TGGGCTCGTC  AGGTTTTAAA  TAGCGAGGGG  CGATTATGAT  1380

AAAAATGCGC  GAGTGATTAA  CGAAAACGAA  GAAAATAAGC  GTAGAATCTC  TATCTGGCTG  1440

GATACCTATT  ATCCGCAGCT  GGCTTATTAT  CGGATTCATT  TCGATTAGAG  CCGCGTAAAC  1500

CCGTTTTCTG  GCTAAGCCGC  CAGCGAAACA  CGATGAGCAA  GAAAGAGTCT  CGAGGTGTTA  1560

AGTCAAAAGC  TGAGAGCGCT  AATGCCTTAC  GCGGATTCGG  TTAACATCAA  ACGTTGATGG  1620

ACGATGTTAC  CGCAGCAGGC  CAGGCGGAAG  CGGGGCTAAA  ACAGCAGGCG  TTAAGAAGAT  1680

TACCTTATTC  CCGCAGGAAT  CATAAGGGGG  GCGTAACGTT  TGTTATTCAG  GGGGCGCTCG  1740

GTGAGATGAT  GTAGAAATAC  TCAGAGCCCG  TCAATTTGTC  GATAGCTATT  ACCGCACATG  1800

GGGAATGGGA  CGCTATGTGC  AGTTTGCGAT  CGAATTAAAA  GATGACTGGC  TCAAGGGGCG  1860

CTCATTTGAG  CAGTACGGGG  CGGAAGGTTA  TATCAAAATG  AGCCCAGGCC  ATTGGTATTT  1920

CCCAAGCCCA  GAGGGCTTTA  ATTAACGTA  AATAAGGAAG  TCATTATGGC  AACACCTTGG  1980

TCAGGCTATC  TGGATATGGA  CGTCTCAGCA  AAATTTGATA  CGGGCGTTGA  TAATCTACAA  2040

ACGCAGGTAA  CAGAGGCGAT  GTTACTGGAT  AAATTAGCAG  CAAAACCCTC  CGATCCGGCG  2100

CTACTGGCGG  CGTATCAGAG  TAAGAAAAC  TCTCGGAATA  TAACTTGTAC  CGTAACGCGC  2160

AATCGAACAC  GGTAAAAGTC  TTTAAGGATA  TGATTGATGC  TGCCATTATT  CAGAACTTCC  2220

GTTAATCAGT  TATAAGGTGG  ATTATGTCGA  TTAAGCAACT  ATTGTCCCTG  AGAATGCCGT  2280

TATAGGGCAG  GCGGTCAATA  TCAGGTCTAT  GGAAATAGAA  CGGACATTGT  CTCGCTGGAT  2340

GACCGGCTAC  TCCAGGCTTT  TTCTGGTTCG  GCGATTGCCT  AGAAACGGCT  GTGGATAAAC  2400

AGACGATTAC  CAACAGGATT  GAGGACCCTA  ATCTGGTGAC  GGATTATTTC  CTAAAGAGCT  2460

GGCTATTTCG  CAAGAGATGA  TTTCAGATTA  TAACCTGTAT  GTTTCTATGA  GGTCAGTACC  2520

CTTACTCGTA  AAGGAGTCGG  GGCTGTTGAA  ACGCTATTAC  GCTCATGATT  CTTGGATGTC  2580

GATATCTATA  TACTTTTCTG  CTGGTAATGA  CCCTTGCCGG  CTGTAAGGAT  AAGGATCTTA  2640

GCTTTTAAAA  GGACTGGACC  AGGAACAGGC  TAATGAGGTC  ATTGCCGTTC  TGCAAATGCA  2700

CAGAAATATA  GAGGCGAATA  AAATTGATAG  CGGAAAATTG  GGCTATAGCA  TTACCGTTGC  2760

TGAGCAGGTA  CTGATTTTAC  CGCTGCGGTG  TACTGGATTA  AAACTTATCA  GCTTCCTCCC  2820

CGGCCACGGG  TAATTGGAAA  TAGCGCAGAT  GTTCCCGGCG  GATTCGCTGG  TATCGTCTCC  2880

GCGAGCTGAA  AAGGAAAACC  AGGTTATATT  CGGCTATTGA  ACAGCGACTG  GAACAGTCAT  2940

TACAGACGAT  GGAGGGCGAT  GTGCTCTCCG  CCAGGGTCCA  TATTAGTTAT  GATATTGATG  3000

CTGGTGAAAA  TGGCCGCCCG  CAAGGCAAAA  CCTGTTCATC  TGTCGGCATT  AGCCGTATAT  3060

GAACGAGGTT  CGCCGCTTGC  GCATCAAGAA  GATCAGCGAT  ATCAAGCGTT  TCTTAAAGAA  3120

TAGTTTTGCC  GATGTGGATT  ATGACAACAA  TTTCTGTTGT  GTTGTCAGAA  CGTTCTGATG  3180

CCCAATTACA  GGCTCCCGGC  ACACCAGTAA  AAGTAACGTA  ATTCTTTTGC  AACCAGTTGG  3240

ATTGTTTTGA  TTATTTTGTT  ATCCGTGATG  TCAGATACAG  GCTTTGGCGT  CTGGTATTAC  3300

AAAAACCATT  ATGCCCGCAA  TAAGAAAGGC  ATAACGGGGA  GTACTGATGA  TAAGGCGAAA  3360

TCGTCAAATG  AATAGGCAGC  CATTACCCAT  TATCTGGCAA  AGAATCATTT  TTGATCCGTT  3420

ATCGTATATC  CATCCTCAGC  GGTTGCAGAT  AGCGCCGGAA  ATGATTGTCA  GACCGCGCCA  3480

CGCGAAATGA  GTTAATACTG  GCGGCATGGC  GGCGGCTTAA  GAACGGAGAA  AAGGAGTGTA  3540

TTCAAAACTC  ACTGACGCAG  CTGTGGCTGC  TCAGTGGCGC  CGACTGCCGC  AAGTAGCGTA  3600

TTTACTAAAC  TGAGAGCCGA  TCTGGCAAGG  CAGGGAGCCT  TGCTTGGCCT  AGCCGGATTG  3660
```

GGCGAAATGA GTTAATACTG GCGGCATGGC GGCTTGCCAT 3700

( 2 ) INFORMATION FOR SEQ ID NO: 11:

( i ) SEQUENCE CHARACTERISTICS:
        ( A ) LENGTH: 392 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 11:

```
Met  Glu  Thr  Ser  Lys  Glu  Lys  Thr  Ile  Thr  Ser  Pro  Gly  Pro  Tyr  Ile
 1             5                        10                          15

Val  Arg  Leu  Leu  Asn  Ser  Ser  Leu  Asn  Gly  Cys  Glu  Phe  Pro  Leu  Leu
          20                       25                       30

Thr  Gly  Arg  Thr  Leu  Phe  Val  Val  Gly  Gln  Ser  Asp  Ala  Leu  Thr  Ala
          35                  40                       45

Ser  Gly  Gln  Leu  Pro  Asp  Ile  Pro  Ala  Asp  Ser  Phe  Phe  Ile  Pro  Leu
 50                       55                       60

Asp  His  Gly  Gly  Val  Asn  Phe  Glu  Ile  Gln  Val  Asp  Thr  Asp  Ala  Thr
 65                  70                       75                            80

Glu  Ile  Ile  Leu  His  Glu  Leu  Lys  Glu  Gly  Asn  Ser  Glu  Ser  Arg  Ser
                    85                       90                            95

Val  Gln  Leu  Asn  Thr  Pro  Ile  Gln  Val  Gly  Glu  Leu  Leu  Ile  Leu  Ile
               100                      105                      110

Arg  Pro  Glu  Ser  Glu  Pro  Trp  Val  Pro  Glu  Gln  Pro  Glu  Lys  Leu  Glu
          115                      120                      125

Thr  Ser  Ala  Lys  Lys  Asn  Glu  Pro  Arg  Phe  Lys  Asn  Gly  Ile  Val  Ala
     130                      135                      140

Ala  Leu  Ala  Gly  Phe  Phe  Ile  Leu  Gly  Ile  Gly  Thr  Val  Gly  Thr  Leu
145                      150                      155                      160

Trp  Ile  Leu  Asn  Ser  Pro  Gln  Arg  Gln  Ala  Ala  Glu  Leu  Asp  Ser  Leu
                    165                      170                      175

Leu  Gly  Gln  Glu  Lys  Glu  Arg  Phe  Gln  Val  Leu  Pro  Gly  Arg  Asp  Lys
               180                      185                      190

Met  Leu  Tyr  Val  Ala  Ala  Gln  Asn  Glu  Arg  Asp  Thr  Leu  Trp  Ala  Arg
          195                      200                      205

Gln  Val  Leu  Ala  Arg  Gly  Asp  Tyr  Asp  Lys  Asn  Ala  Arg  Val  Ile  Asn
     210                      215                      220

Glu  Asn  Glu  Glu  Asn  Lys  Arg  Ile  Ser  Ile  Trp  Leu  Asp  Thr  Tyr  Tyr
225                      230                      235                      240

Pro  Gln  Leu  Ala  Tyr  Tyr  Arg  Ile  His  Phe  Asp  Glu  Pro  Arg  Lys  Pro
               245                      250                      255

Val  Phe  Trp  Leu  Ser  Arg  Gln  Arg  Asn  Thr  Met  Ser  Lys  Lys  Glu  Leu
          260                      265                      270

Glu  Val  Leu  Ser  Gln  Lys  Leu  Arg  Ala  Leu  Met  Pro  Tyr  Ala  Asp  Ser
     275                      280                      285

Val  Asn  Ile  Thr  Leu  Met  Asp  Asp  Val  Thr  Ala  Ala  Gly  Gln  Ala  Glu
     290                      295                      300

Ala  Gly  Leu  Lys  Gln  Gln  Ala  Leu  Pro  Tyr  Ser  Arg  Arg  Asn  His  Lys
305                      310                      315                      320

Gly  Gly  Val  Thr  Phe  Val  Ile  Gln  Gly  Ala  Leu  Asp  Asp  Val  Glu  Ile
                    325                      330                      335

Leu  Arg  Ala  Arg  Gln  Phe  Val  Asp  Ser  Tyr  Tyr  Arg  Thr  Trp  Gly  Gly
               340                      345                      350
```

-continued

Arg Tyr Val Gln Phe Ala Ile Glu Leu Lys Asp Asp Trp Leu Lys Gly
          355                 360                 365

Arg Ser Phe Gln Tyr Gly Ala Glu Gly Tyr Ile Lys Met Ser Pro Gly
          370                 375                 380

His Trp Tyr Phe Pro Ser Pro Leu
385                 390

(2) INFORMATION FOR SEQ ID NO: 12:

(i) SEQUENCE CHARACTERISTICS:
      (A) LENGTH: 80 amino acids
      (B) TYPE: amino acid
      (D) TOPOLOGY: linear (ii) MOLECULE TYPE: peptide (xi) SEQUENCE DESCRIPTION: SEQ ID NO: 12:

Met Ala Thr Pro Trp Ser Gly Tyr Leu Asp Asp Val Ser Ala Lys Phe
 1               5                   10                  15

Asp Thr Gly Val Asp Asn Leu Gln Thr Gln Val Thr Glu Ala Leu Asp
              20                  25                  30

Lys Leu Ala Ala Lys Pro Ser Asp Pro Ala Leu Leu Ala Ala Tyr Gln
          35                  40                  45

Ser Lys Leu Ser Glu Tyr Asn Leu Tyr Arg Asn Ala Gln Ser Asn Thr
      50                  55                  60

Val Lys Val Phe Lys Asp Ile Asp Ala Ala Ile Ile Gln Asn Phe Arg
65                  70                  75                  80

(2) INFORMATION FOR SEQ ID NO: 13:

(i) SEQUENCE CHARACTERISTICS:
      (A) LENGTH: 101 amino acids
      (B) TYPE: amino acid
      (D) TOPOLOGY: linear (ii) MOLECULE TYPE: peptide (xi) SEQUENCE DESCRIPTION: SEQ ID NO: 13:

Met Ser Ile Ala Thr Ile Val Pro Glu Asn Ala Val Ile Gly Gln Ala
 1               5                   10                  15

Val Asn Ile Arg Ser Met Glu Thr Asp Ile Val Ser Leu Asp Asp Arg
              20                  25                  30

Leu Leu Gln Ala Phe Ser Gly Ser Ala Ile Ala Thr Ala Val Asp Lys
          35                  40                  45

Gln Thr Ile Thr Asn Arg Ile Glu Asp Pro Asn Leu Val Thr Asp Pro
      50                  55                  60

Lys Glu Leu Ala Ile Ser Gln Glu Met Ile Ser Asp Tyr Asn Leu Tyr
65                  70                  75                  80

Val Ser Met Val Ser Thr Leu Thr Arg Lys Gly Val Gly Ala Val Glu
              85                  90                  95

Thr Leu Leu Arg Ser
              100

(2) INFORMATION FOR SEQ ID NO: 14:

(i) SEQUENCE CHARACTERISTICS:
      (A) LENGTH: 252 amino acids
      (B) TYPE: amino acid
      (D) TOPOLOGY: linear (ii) MOLECULE TYPE: peptide ( x i ) SEQUENCE DESCRIPTION: SEQ ID NO: 14:

| | | | | | | | | | | | | | | |
|---|---|---|---|---|---|---|---|---|---|---|---|---|---|---|
| Met | Ile | Arg | Arg | Tyr | Leu | Tyr | Thr | Phe | Leu | Leu | Val | Met | Thr | Leu | Ala |
| 1 | | | | 5 | | | | | 10 | | | | | 15 | |
| Gly | Cys | Lys | Asp | Lys | Asp | Leu | Leu | Lys | Gly | Leu | Asp | Gln | Gln | Ala | |
| | | | 20 | | | | | 25 | | | | | 30 | | |
| Asn | Glu | Val | Ile | Ala | Val | Leu | Gln | Met | His | Asn | Ile | Glu | Ala | Asn | Lys |
| | | 35 | | | | | 40 | | | | | 45 | | | |
| Ile | Asp | Ser | Gly | Lys | Leu | Gly | Tyr | Ser | Ile | Thr | Val | Ala | Glu | Pro | Asp |
| | 50 | | | | | 55 | | | | | 60 | | | | |
| Phe | Thr | Ala | Ala | Val | Tyr | Trp | Ile | Lys | Thr | Tyr | Gln | Leu | Pro | Pro | Arg |
| 65 | | | | | 70 | | | | 75 | | | | | 80 | |
| Pro | Arg | Val | Glu | Ile | Ala | Gln | Met | Phe | Pro | Ala | Asp | Ser | Leu | Val | Ser |
| | | | | 85 | | | | | 90 | | | | | 95 | |
| Ser | Pro | Arg | Ala | Glu | Lys | Ala | Arg | Leu | Tyr | Ser | Ala | Ile | Glu | Gln | Arg |
| | | | 100 | | | | | 105 | | | | | 110 | | |
| Leu | Glu | Gln | Ser | Leu | Gln | Thr | Met | Glu | Gly | Val | Leu | Ser | Ala | Arg | Val |
| | | 115 | | | | | 120 | | | | | 125 | | | |
| His | Ile | Ser | Tyr | Asp | Ile | Asp | Ala | Gly | Glu | Asn | Gly | Arg | Pro | Pro | Lys |
| | 130 | | | | | 135 | | | | | 140 | | | | |
| Pro | Val | His | Leu | Ser | Ala | Leu | Ala | Val | Tyr | Glu | Arg | Gly | Ser | Pro | Leu |
| 145 | | | | | 150 | | | | | 155 | | | | | 160 |
| Ala | His | Gln | Ile | Ser | Asp | Ile | Lys | Arg | Phe | Leu | Lys | Asn | Ser | Phe | Ala |
| | | | | 165 | | | | | 170 | | | | | 175 | |
| Asp | Val | Asp | Tyr | Asp | Asn | Ile | Ser | Val | Val | Leu | Ser | Glu | Arg | Ser | Asp |
| | | | 180 | | | | | 185 | | | | | 190 | | |
| Ala | Gln | Leu | Gln | Ala | Pro | Gly | Thr | Pro | Val | Lys | Arg | Asn | Ser | Phe | Ala |
| | | 195 | | | | | 200 | | | | | 205 | | | |
| Thr | Ser | Trp | Ile | Val | Leu | Ile | Ile | Leu | Leu | Ser | Val | Met | Ser | Ala | Gly |
| | 210 | | | | | 215 | | | | | 220 | | | | |
| Phe | Gly | Val | Trp | Tyr | Tyr | Lys | Asn | His | Tyr | Ala | Arg | Asn | Lys | Lys | Gly |
| 225 | | | | | 230 | | | | | 235 | | | | | 240 |
| Ile | Thr | Ala | Asp | Asp | Lys | Ala | Lys | Ser | Ser | Asn | Glu | | | | |
| | | | | 245 | | | | | 250 | | | | | | |

( 2 ) INFORMATION FOR SEQ ID NO: 15:

( i ) SEQUENCE CHARACTERISTICS:
        ( A ) LENGTH: 818
        ( B ) TYPE: nucleic acid
        ( C ) STRANDEDNESS: double
        ( D ) TOPOLOGY: linear ( x i ) SEQUENCE DESCRIPTION: SEQ ID NO: 15:

| | | | | | |
|---|---|---|---|---|---|
| CATAACAACT | CCTTAATACT | ACTTATTATT | TACGGTGTGT | TTAAACACCT | GCAGTACCGA | 60 |
| TCCGGCATTC | AGTTATCGCC | ACTATGCCGA | ATCGACAAAA | CCACGAATAA | TTCACCGCTA | 120 |
| TCGCTCCTGA | TGTGTTTACT | TCCTGAAAGA | TATTTTTACT | ACCGAAGCAC | TCTATCGCTC | 180 |
| ATTTAGGTAA | CCGGTTCTAC | AATGTCATCT | AACTTTTATA | GATTTGAATG | CTAATTTTTC | 240 |
| TCACGCATAT | ATATTTAACA | GAAACCATAA | AGTGTTTAGC | CACTATAGAA | CAACAAATCA | 300 |
| CCCATGCAAC | ATTTTGATAT | TTAAAGAGAA | AATCTCACAA | CCACATTAAG | AAACTTGACA | 360 |
| CCGTTCGGCT | AAAAAACATG | TCATTAAGCA | AACTCGCCAT | ATAATCAGAA | CATATCGCAT | 420 |
| TGTGCTTCAC | AGTCCTCACG | TGACGCTCCA | TCCGCAATAC | GGTTATATGC | CATCGCAGGC | 480 |
| GCTGTAATCA | TATTCACGAT | GATGCTTAGC | ACGCTTTATT | CCCGCTCCGA | TTTAATCTTT | 540 |
| TAATATATCT | ATCAGTTACA | ACATTTCTTG | TTATATTATA | AGAATAGAAT | CAACACCACA | 600 |

-continued

| | | | | | | |
|---|---|---|---|---|---|---|
| ATTCCAACAT | AAATATCACC | TGTGTTTAGA | GAGAATTTAC | ATTCCAAAAA | AATAATAACT | 660 |
| AACGCAAATA | TTGAACACGC | GATAAAAAAG | TCTATTTCGC | TATAAAACCC | ATTATTATTA | 720 |
| AGAGTGGTTA | ACTCTTCGTT | GAATAAAAAA | TGTCAATGAC | GTTCCATAAT | TCAGGAGATG | 780 |
| AACTTCACAA | GTCATTATAT | ATAACAGGAG | GTGCTATG | | | 818 |